(12) United States Patent
Garcia Lara et al.

(10) Patent No.: US 9,610,341 B2
(45) Date of Patent: Apr. 4, 2017

(54) BACTERIAL VACCINE

(71) Applicant: Absynth Biologics Limited, Sheffield South Yorkshire (GB)

(72) Inventors: Jorge Garcia Lara, Sheffield (GB); Simon Foster, Hathersage (GB)

(73) Assignee: Absynth Biologics Limited, Sheffield (GB)

( * ) Notice: Subject to any disclaimer, the term of this patent is extended or adjusted under 35 U.S.C. 154(b) by 0 days.

(21) Appl. No.: 14/384,682

(22) PCT Filed: Apr. 9, 2013

(86) PCT No.: PCT/GB2013/050910
§ 371 (c)(1),
(2) Date: Sep. 11, 2014

(87) PCT Pub. No.: WO2013/153372
PCT Pub. Date: Oct. 17, 2013

(65) Prior Publication Data
US 2015/0050312 A1    Feb. 19, 2015

(30) Foreign Application Priority Data
Apr. 11, 2012 (GB) .................................. 1206366.5

(51) Int. Cl.
| | | |
|---|---|---|
| *A61K 39/02* | (2006.01) | |
| *A61K 39/118* | (2006.01) | |
| *A61K 39/09* | (2006.01) | |
| *A61K 39/108* | (2006.01) | |
| *A61K 39/112* | (2006.01) | |
| *A61K 39/04* | (2006.01) | |
| *A61K 39/07* | (2006.01) | |
| *A61K 39/08* | (2006.01) | |
| *A61K 39/095* | (2006.01) | |
| *A61K 39/102* | (2006.01) | |
| *A61K 39/104* | (2006.01) | |
| *A61K 39/00* | (2006.01) | |

(52) U.S. Cl.
CPC ........ *A61K 39/092* (2013.01); *A61K 39/0208* (2013.01); *A61K 39/0258* (2013.01); *A61K 39/0283* (2013.01); *A61K 39/0291* (2013.01); *A61K 39/04* (2013.01); *A61K 39/07* (2013.01); *A61K 39/08* (2013.01); *A61K 39/09* (2013.01); *A61K 39/095* (2013.01); *A61K 39/102* (2013.01); *A61K 39/104* (2013.01); *A61K 39/105* (2013.01); *A61K 39/118* (2013.01); *A61K 2039/70* (2013.01)

(58) Field of Classification Search
None
See application file for complete search history.

(56) References Cited

U.S. PATENT DOCUMENTS

2004/0029129 A1* 2/2004 Wang .................. C07K 14/195
                                                                435/6.18

FOREIGN PATENT DOCUMENTS

| WO | 02/34771 A2 | 5/2002 |
|---|---|---|
| WO | 2005/105845 A2 | 11/2005 |
| WO | 2006/100430 A2 | 9/2006 |
| WO | 2010/076618 A1 | 7/2010 |
| WO | 2011/042681 A2 | 4/2011 |

OTHER PUBLICATIONS

Baillie, Leslie W., "Is new always better than old? The development of human vaccines for anthrax," Human Vaccines, vol. 5, No. 12, pp. 806-816 (Dec. 2009).
Scorpio, A. et al., "Anthrax vaccines: Pasteur to the prsent," Cell, Mol. Life. Sci., vol. 63, pp. 2237-2248 (2006).
UNIPROT Accession No. Q5XA26, dated Nov. 23, 2004; URL: http://www.uniprot.org/uniprot/Q5XA.txt?version=59, cited in International Search Report dated Jun. 24, 2013 for PCT Appl. No. PCT/GB2013/050910.

* cited by examiner

*Primary Examiner* — Oluwatosin Ogunbiyi
(74) *Attorney, Agent, or Firm* — Seed IP Law Group LLP

(57) ABSTRACT

The disclosure relates to a composition comprising one, two or more immunogenic bacterial polypeptides and multivalent and monovalent vaccine compositions comprising the immunogenic bacterial polypeptides.

20 Claims, 16 Drawing Sheets

PheP PROTEIN SEQUENCES

SEQ ID NO: 1 >YP_019717 [Bacillus anthracis str. 'Ames Ancestor']
MNSATNQTTSQTETTKGKGELRRGLKSKHLTMISLGGTIGTGLFLASGGVIHSAGPGGALIAYAA
IGIMVYFLMTSLAELAAYMPVTGSFSTYATKFVDPSLGFALGWNYWYNWAITIAAELAAVTLIMK
FWFPDTPSLIWSGLCLAIIFLLNYLSVKGFGESEYWFALIKVATIIIFLIVGFMMIFGIMGGETV
GFKNFTVADAPFNGGIMAIIGVFMAAGFSFQGTELLGVAAGETSDPERNIPKAIRSIFWRILLFY
ILAILVIGLLIPYTTESLAASDVTVSPFTLIFEKAGVAFAASVMNAVILTAVLSAGNSGMYASTR
MLWDLARQGKAPKFLGKLDSRGVPVNALIVTSIVGSIAFIASLFGDGVVYIWLLNASGMSGFIAW
VGIAISHYRFRKAYIAQGKDLNDLPYRAKWFPFGPIFAFALCVIVILGQNYGAFMGESIDWNGVL
VSYIGLPLFLVLWLGYKFTKKTKVIPLDKCELK

SEQ ID NO: 2 GVIHSAGPGGAL

SEQ ID NO: 3 LAAVTLIMKFWFPDTPSL

SEQ ID NO: 4 MMIFGIMGGETVGFKNFTVADAPFNGGIMAI

SEQ ID NO: 5 IPYTTESLAASDVTVSPFTLIFEKAGVA

SEQ ID NO: 6 ASLFGDGVVYIWL

SEQ ID NO: 7 GQNYGAFMGESIDWNG

SEQ ID No: 8 >YP_001078946 [Burkholderia mallei NCTC 10247]
MATDQDNDGLKRGLKNRHIQLIALGGAIGTGLFLGIAQTIRMAGPSVLLGYALAGVVAFFIMRQL
GEMVVDEPVAGSFSYFASKYCGHFTGFLSGWNYWVLYVLVSMAELSAVGIYVQYWWPGVPTWISA
LVFFVVINAVNLASVKSYGETEFWFSIVKVAAIIGMIGFGGYLLLSGHAGPDAGVANLWRHGGFF
PNGIGGLAMAMAVIMFSFGGLELVGITAAEADDPSHSIPRATNQVIYRILIFYIGALGVLLSLYP
WQKVVTGGSPFVLIFHALSSDIAANVLNLVVLTAALSVYNSCVYCNSRMLYGLAQQGNAPQALAR
VNRRGIPIAALGVSAFATALCVVINYFMPGKAFELLMGLVVSAIIINWAMISVIHLRFRQAKRAA
GETTRFRSLGYPLTNYFCLAFMAAILVVMFRTPELRLSVYLIPVWLVVLALGYRFRQRGAGYALG
GGVSAR

SEQ ID NO: 9 AQTIRMAGPSVLL

SEQ ID NO: 10 SMAELSAVGIYVQYWWPGVPTW

SEQ ID NO: 11 LLLSGHAGPDAGVANLWRHGGFFPNGIGGL

SEQ ID NO: 12 YPWQKVVTGGSPFVLIFHALSSDIAANV

SEQ ID NO: 13 INYFMPGKAFELL

SEQ ID NO: 14 MFRTPELRL

SEQ ID NO: 15 >YP_111919 [Burkholderia pseudomallei K96243]
MSPHPNSDNSTAQSNPPQLRRSLKARHLTMIAIGGSIGTGLFVASGASISQAGPGGAMLAYLLIG
LMVYCLMMSLGEMAAFMPVSGSFATYGAKYVEEGFGFALGWNYWYNWAVTIAVELVAAQLVMHYW
FPDVPGVWWSAAFLGVMFLLNVLTVRGFGEAEYWFALIKVVTVIAFIGVGLLMIFGILKGGPSNG
WSNFTIGDAPFAGGLPAMMGVAMIAGFSFQGTELIGVAAGESENPRTTIPRAVRQVFWRILLFYV
LAIFVIGVLIPYTDPNLLKSDVTDVGVSPFTLVFRHAGLAFAAGVMNAVILTAVLSAGNSGMYAS
TRMLHNLATEGRAPKLFAKLSAGGVPRNALYATTAVGALCFLSSLYGDKTVYLWLLNTSGMTGFI
AWLGIALSHYRFRKGYVRQGFSVDQLPYQSSLYPYGPIFAFALCIVIALGQDYQAFLANRIDWIG
VLATYVGIPLFLVVWLGYRLVHKTRVVRYEDMDIASWVAEHERAAAHEAREAAAVRVPSSPEAAS

FIG. 1 (continued)

SEQ ID NO: 16 ASISQAGPGGAMLAYL

SEQ ID NO: 17 AQLVMHYWFPDVPGVWW

SEQ ID NO: 18 IFGILKGGPSNGWSNFTIGDAPFAGGLPAMM

SEQ ID NO: 19 IPYTDPNLLKSDVTDVGVSPFTLVFRHAGLA

SEQ ID NO: 20 LSSLYGDKTVYLWL

SEQ ID NO: 21 GQDYQAFLANRIDWIGV

SEQ ID NO: 22 >YP_001252793 [Clostridium botulinum A str. ATCC 3502]
MSTTKEKDSNSHNLKRSLQARHLNMIAMGGAIGTGIFLALGATIKQAGPGGALTAYACIGVMVYF
LMTSLGEMATFMPVSGSFETYASRFIDPAFGFALGWNYWYNWAITVAAEMVAGALIMKFWFPNVP
AIIWSVLFLVLIVSLNLLSTKAYGESEYWFAGIKVFTVIVFLLIGIATILGILGGHTVGLQNFTI
KDAPFVGGVKSIFMVFLIAGFSFQGTELVGIAAGESENPKKTIPKAINTIFWRIIVFYLGTIFVV
SAIIPYTDAGVNTSPFTLVFERAGIAADASLMNAVILTSVISCGNSGMYASSRMLYAMAKEGKAP
SWLGKLNSRGVPVNALALTTLVASACFLTGLYAETTVYVWLVAASGLAGFIAWVGIALCHYRFRK
AYVAQGRDLNKLVYKAKLFPLGPIIALVLCIIVILGQGISYFEATKIDWNGIIASYIGLPIFFGL
WFSYKKKHKTKVVNLQEISFDVEDTHLKTEIV

SEQ ID NO: 23 GATIKQAGPGGALTAY

SEQ ID NO: 24 MVAGALIMKFWFPNVPAI

SEQ ID NO: 25 LGILGGHTVGLQNFTIKDAPFVGGVKSIFM

SEQ ID NO: 26 AIIPYTDAGVNTSPFTLVFERAGIAADAS

SEQ ID NO: 27 GLYAETTVYVWLV

SEQ ID NO: 28 GQGISYFEATKIDWN

SEQ ID NO: 29 >ZP_06893302 [Clostridium difficile NAP08]
MRRKKMESNELKKTLGVSAALSTVVGSVIGAGVFFKPQAVYTLTGGAPGLGILAWLIAGIITITA
GLTAAEVSVAIPKTGGMMVYIKEIYGEKLGFLTGWMQIVLFYPGMMAALGVIFGEQASALIGSPS
LLLPIAIGIIVIVAGLNMLGSKTGGVIQTVSTICKLIPLILIMIVGFIKGGGNNPILTPMVGEGL
SLGSVLGQVLIAILFAFDGWMNVGTLAGEMKNPGKDLPKAIIGGLSVVMAVYFIINLAYLWVLPA
SELANYASPASAVAEVIFGSMGGKIISVGILISVFGALNGFLLTGSRVAYTLATDKTLPKYSIFS
KLNSAQVPANAIALVSVIASIYALSGQFNLLTDLAVFATWIFYVLTFIGVMKLRKTHPNIPREYK
VPLYPIVPIIAIASGIFVVVNQLCFAGMKTTMISIGGLVITAIGLPVYAYMTRGIKR

SEQ ID NO: 30 VFFKPQAVYTLTGGAPGLGILAW

SEQ ID NO: 31 LGVIFGEQASALIGSPSL

SEQ ID No: 32 GFIKGGGNNPILTPMVGEGLSLGS

SEQ ID NO: 33 LWVLPASELANYASPASAVAEVIFGSMGGKIISVGI

SEQ ID NO: 34 ALSGQFNLLTD

FIG. 1 (continued)

SEQ ID NO: 35 NQLCFAGMKTTM

SEQ ID NO: 36 >EFT88633 [Enterococcus faecalis TX2141]
MSETQQTTLKKQLSSRHITMLALGGAIGAGLFKGSGEAIGIAGPSVLIAFLIGGAVLFIVMSGLG
KLVLDGGDTHHGLSGLVRPFLGAHSADFIDWVYYSMWTINIIAEAVAAASFLQLWFPNIPAWFFV
FILAILTTLINLYSVRLFAETEYWLAFAKISVIILLIIFGVYLVGQQMLGSGVFPTLQSITKHGG
FAPHGMKGIVNSLLVVIYSYGGSELIAITVSEADDPKKAIPKAIRGVMGRIISFYIIPLFLLLII
FPWNTLASTTVSPFVMVFEKMNIPFAADIVNFVIILALFSSINSGVYASSRLLYFRLKDKKGPMS
KLAVLNKHQVPQRSVFFCASVLYLGVILSYFVGDELFGYLAGSLSYTVLLIWILISAAAFVLSLK
RGSLFEKSINLLALIILGLIFIGILFTNSLGVTLLTGLLYFVIFFSYRKKNDSFLLSDES

SEQ ID NO: 37 FKGSGEAIGIAGPSVLIA

SEQ ID NO: 38 ASFLQLWFPNIPAWF

SEQ ID NO: 39 YLVGQQMLGSGVFPTLQSITKHGGFAPHGMKGIVNSL

SEQ ID NO: 40 PWNTLASTTVSPFVMVFEKMNIPFAADIVNFV

SEQ ID NO: 41 FVGDELFGYLAGSLS

SEQ ID No: 42 TNSLGVTLLTGLLYFVIFFSYRKKNDSFLLSDES

SEQ ID No: 43 >NP_416661 [Escherichia coli str. K-12 substr. MG1655]
MVSETKTTEAPGLRRELKARHLTMIAIGGSIGTGLFVASGATISQAGPGGALLSYMLIGLMVYFL
MTSLGELAAYMPVSGSFATYGQNYVEEGFGFALGWNYWYNWAVTIAVDLVAAQLVMSWWFPDTPG
WIWSALFLGVIFLLNYISVRGFGEAEYWFSLIKVTTVIVFIIVGVLMIIGIFKGAQPAGWSNWTI
GEAPFAGGFAAMIGVAMIVGFSFQGTELIGIAAGESEDPAKNIPRAVRQVFWRILLFYVFAILII
SLIIPYTDPSLLRNDVKDISVSPFTLVFQHAGLLSAAAVMNAVILTAVLSAGNSGMYASTRMLYT
LACDGKAPRIFAKLSRGGVPRNALYATTVIAGLCFLTSMFGNQTVYLWLLNTSGMTGFIAWLGIA
ISHYRFRRGYVLQGHDINDLPYRSGFFPLGPIFAFILCLIITLGQNYEAFLKDTIDWGGVAATYI
GIPLFLIIWFGYKLIKGTHFVRYSEMKFPQNDKK

SEQ ID NO: 44 GATISQAGPGGALLSYMLI
SEQ ID NO: 45 AAQLVMSWWFPDTPGWI

SEQ ID NO: 46 MIIGIFKGAQPAGWSNWTIGEAPFAGG

SEQ ID NO: 47 IIPYTDPSLLRNDVKDISVSPFTLVFQHAG

SEQ ID NO: 48 TSMFGNQTVYLWL

SEQ ID NO 49 TLGQNYEAFLKDTIDWGGVAA

FIG. 1 (continued)

SEQ ID NO: 50 >ZP_05851026 [Haemophilus influenzae NT127]
MSDKEVKKSLTLRHIQFLALGSAIGTGLFYGSYESIKLAGSSVIFGYLIIGFIIYIIMKSLGDLI
LNTPTGKTFGDYASIYLGKKWGFVTGWAYALEMIIVCIADLTAFGIYMKFWYPEVDSWIWITILI
FFIASINLINVRVFGELEFILTIIKVIAIGFMIVIGVILLFYTQLNKDSLEQIASINNLIKYGGF
FPNGLEGFIYSLSIIAFSFGGIEIIGISAGETLDPKKSIPIAIRSVPFRIIFFYIFTIFIILTIV
PWNNLDGSKSPFVIIFEYIGIPYSSDILNIVIISASISAINSDIFSASRIIYSMSKRNQAPIILS
RISKQGIPWVVVLLVSFLLCFGIFLNYLFPDKIFIFIASSASVITIFVWIIILFSNMFMNNNRLS
SFIGFLQKNKFILFSIFSLVFIVLFMLLNKETRWASLVGVSIILLIFIIGTKFNNIIFKENKDEC

SEQ ID NO: 51 FYGSYESIKLAGSSVIFGY

SEQ ID NO: 52 LTAFGIYMKFWYPEVDSWIW

SEQ ID NO: 53 LLFYTQLNKDSLEQIASINNLIKYGGFFPNGLEGFI

SEQ ID NO: 54 VPWNNLDGSKSPFVIIFEYIGIPYSSDILNIV

SEQ ID NO: 55 NYLFPDKIF

SEQ ID NO: 56 LNKETRWASL

SEQ ID NO: 57 >ACX99977 [Helicobacter pylori 52]
MKDNTTLSRDISFNQLMMIALGGTIGTGLFVGTGGNIASAGPLATLLAYLIGGIIVYSIVLSLGE
LASVYPTTGSFGDYASRFINPSTGYMVFWMYWLSWVLTVAVEYIAIGLLMQRWFPTIPVYVWVIV
CIALLFLLNFFSVKIFATGEFLLSTIKVLAVFVFIVLGCIGIVYSFYLHGFEGVFANFYFNGETQ
GLEKGFFPKGVGAFFGAILAVIFAYTGTEIIGVAAGETKDAKKVMPKAIKATLWRIVFFFLGAVF
VVSVFLPMTDSSLTQSPFVSALEKIPLPFWGVGIPYAADIMNFVIVTAILSTANSGLYASGRMIY
GLSQKKMFFPLFAKLNASGTPTYALYLSLGVTLIGMLTEAFAPEKIMASLINVVSFMVIIVWISI
SVAQYHFRKEYLALRKSLKDLPYKAPLNPLIQIIGISGCLVGLIGAYMDANERIGGYLTLVFMGL
CYGAYYLSKDKWGYQQEKGI

SEQ ID NO: 58 GTGGNIASAGPLATLLAY

SEQ ID NO: 59 AIGLLMQRWFPTIP

SEQ ID NO: 60 VYSFYLHGFEGVFANFYFNGETQGLEKGFFPKGVGAF

SEQ ID NO: 61 LPMTDSSLTQSPFVSALEKIPLPFWGVGIPYAADIMN

SEQ ID NO: 62 GVTLIGMLTEAFAPEKIMASLIN

SEQ ID NO: 63 GAYMDANERIG

SEQ ID NO: 64 >ZP_07663883 [Mycobacterium tuberculosis SUMu001]
MPPTDRKAGAIATTSGLRPGLSQRQLNMIAIGGVIGAGLFVGSGVVIRATGPAAFLTYALCGALI
VLVMRMLGEMAAANPSTGAFADYAAKALGGWAGFSVGWLYWYFWVIVVGFEAVAGGKVLTYWIDA
PLWLASLCLMMMMTATNLVSVSSFGEFEFWFAGVKVATIVGFLVLGTAFAFGLLPGHGMDFSNLS
AHGGFFPDGVGAVFAAIVVAIFSMTGTEVVTIAAAEAPDPQRAVQRAMSTVVARIVIFFVGSVFL
LTVILPWNSLELGASPYVAALRHMGIGGADQIMNAVVLTAVLSCLNSGLYTASRMLFVLAARQEA
PAQLVKVNRRGVPTFAIMGSSVVGFLCVIMAWVSPATVFVFLLNSSGAVILFVYLLIALSQIVLR
RQTSGQNLGVRMWLFPGLSIVTVTGIVAVLARMAFDYAARSQLWLSLLSWAVVVGCYLVTTLVRR
PLNRPW

FIG. 1 (continued)

SEQ ID NO: 65 GVVIRATGPA

SEQ ID NO: 66 VIVVGFEAVAGGKVLTYWIDAPLWL

SEQ ID NO: 67 AFGLLPGHGMDFSNLSAHGGFFPDGVGA

SEQ ID NO: 68 VILPWNSLELGASPYVAALRHMGIGGADQIMNAVV

SEQ ID NO: 69 WVSPATVFVF

SEQ ID NO: 70 RMAFDYAARSQLW

SEQ ID NO: 71 >NP_253318 [Pseudomonas aeruginosa PAO1]
MTDLNTSQGQQLRRVLKPRHLNMIAIGGSIGTGLFVASGATVATAGPGGALLSYALIGLMVYFLM
TSLGEMAAYMPVSGSFCTYGSRFVEDGFGFALGWNYWYNWAVTIAAELVAAQLVMSFWFPEVPGI
YWSAIFLGIMFGLNVISARGFGESEFWFALIKVVTVVIFIGVGLATIFGIMHGVESPGFSNFTMG
DAPFVGGFQAMVGVAMIAGFSFQGTELIGIAAGESENPRKNIPIAIRQVFWRILMFYILAIFVIG
MLIPYTDPNLLKNDASDISVSPFTLLFERAGFAAAAGVMNAVILSAILSAGNSGMYASTRMLYNL
ALEGKAPRLFSRVSRSGVPRNALYATTLVGALCFLTSAFGDSTVYTWLLNTSGMCGFIAWLGIAI
SHYRFRKGYLAQGGRLEDLPYRAKLFPFGPLFAFALCMVITLGQNYQALVGERIDWIGLLATYIS
LPLFLAIWLGYRWKKRARFVRYHEMDVSPTNT

SEQ ID NO: 72 ATVATAGPGGALLSYALI

SEQ ID NO: 73 AQLVMSFWFPEVPGI

SEQ ID NO: 74 IFGIMHGVESPGFSNFTMGDAPFVGGFQ

SEQ ID NO: 75 MLIPYTDPNLLKNDASDISVSPFTLLFERAGFAA

SEQ ID NO: 76 TSAFGDSTVYTWLL

SEQ ID NO: 77 GQNYQALVGERIDWIG

SEQ ID NO: 78 >NP_708053 [Shigella flexneri 2a str. 301]
MGSETKTTEAPGLRRELKARHLTMIAIGGSIGTGLFVASGATISQAGPGGALLSYMLIGLMVYFL
MTSLGELAAYMPVSGSFATYGQNYVEEGFGFALGWNYWYNWAVTIAVDLVAAQLVMSWWFPDTPG
WIWSALFLGVIFLLNYISVRGFGEAEYWFSLIKVTTVIVFIIVGVLMIIGIFKGAQPAGWSNWTI
GEAPFAGGFAAMIGVAMIVGFSFQGTELIGIAAGESEDPAKNIPRAVRQVFWRILLFYVFAILII
SLIIPYTDPSLLRNDVKDISVSPFTLVFQHAGLLSAAAVMNAVILTAVLSAGNSGMYASTRMLYT
LACDGKAPRIFAKLSRGGVPRNALYATTVIAGLCFLTSMFGNQTVYLWLLNTSGMTGFIAWLGIA
ISHYRFRRGYVLQGHDINDLPYRSGFFPLGPIFAFILCLIITLGQNYEAFLKDTIDWGGVAATYI
GIPLFLIIWFGYKLIKGTHFVRYSEMKFPQNDKK

SEQ ID NO: 79 GATISQAGPGGALLSYMLIG

SEQ ID NO: 80 AAQLVMSWWFPDTPGWIW

SEQ ID NO: 81 MIIGIFKGAQPAGWSNWTIGEAPFAGG

SEQ ID NO: 82 IPYTDPSLLRNDVKDISVSPFTLVFQHAG

SEQ ID NO: 83 TSMFGNQTVYLWL

FIG. 1 (continued)

SEQ ID NO: 84 TLGQNYEAFLKDTIDWGGVA

SEQ ID NO: 85 >YP_001835692 [Streptococcus pneumoniae CGSP14]
MESKMNIFRTKNVSLDKTEMHRHLKLWDLILLGIGAMVGTGVFTITGTAAATLAGPALVISIVIS
ALCVGLSALFFAEFASRVPATGGAYSYLYAILGEFPAWLAGWLTMMEFMTAISGVASGWAAYFKG
LLSQYGIAFPQALNGTFNPQAGTFVDLLPILVLVLVTSLVLLNAKAALRFNSILVILKFSALALF
VLVGIWNIKFDNWSNFAPYGFGQIYGASTGIMAGASLMFFGFLGFESISMAVDEVKTPQKNIPRG
IVLSLSIVTILYALVTLVLTGVVHYSHLNVDDAVAFALRSVGISWAANYVSLVAILTLITVCISM
TYALSRMIYSLARDGLVPAAFKELTKTSKIPKNATILTGLASAVAAGMFPLASIAAFLNICTLAY
LIMLAYGLIRLRKEKGMPKAGEFKTPLVPLLPILSIIICLSFMLQYNMNTWIAFLVALLVGSIIY
FTYGYKHSTIEE

SEQ ID NO: 86 TITGTAAATLAGPALV

SEQ ID NO: 87 TMMEFMTAISGVASGWAAYFKGLLSQYGIAFPQALNGTFNPQAGTF

SEQ ID NO: 88 IWNIKFDNWSNFAPYGFGQIYG

SEQ ID NO: 89 TGVVHYSHLNVDDAVAFALRSVGISWAANYV

SEQ ID NO: 90 MFPLASIAAF

SEQ ID NO: 91 >NP_670176 [Yersinia pestis KIM 10]
MTQQNTKIPAQQGAQRLRRELKSRHLAMIAIGGSIGTGLFVASGATVSQAGPGGALLSYALIGLM
VYFLMTSLGELAAFMPVSGSFSTYGSKYVEEGFGFALGWNYWYNWAVTIAVDLVAAQLVMNYWFP
DAPGWIWSALFLGLMFLLNYISVKGFGEAEYWFSLIKVTTVVIFIIVGVMMITGIMKGGETAGWH
NWTIGDAPFAGGFSAMIGVAMIVGFSFQGTELIGIAAGESKDPGKNIPKAIRKVFWRILLFYIFA
ILIISLIIPYTDPSLLRNDVKDISVSPFTLVFQNAGLLSAAAVMNAVILTAVLSAGNSGMYASTR
MLFTLASEGKAPRIFAKLSKGGVPRNALYATTVAGLCFLSSMFGNQTVYLWLLNTSGMTGFIAW
LGIAISHYRFRRGYMMQGRDLNDLPYQSGFFPLGPIFAFVLCLIITLGQNYQAFLQDRIDWYGVT
ATYIGIPLFLVIWFGYKLSRGTRVVKYQEMEFPKWRDESEEHQKPTSR

SEQ ID NO: 92 VASGATVSQAGPGGALLSYALIG

SEQ ID NO: 93 VAAQLVMNYWFPDAPGWI

SEQ ID NO: 94 MITGIMKGGETAGWHNWTIGDAPFAGGFSA

SEQ ID NO: 95 IPYTDPSLLRNDVKDISVSPFTLVFQNAGL

SEQ ID NO: 96 SSMFGNQTVYLWLLN

SEQ ID NO: 97 ITLGQNYQAFLQDRIDWYGV

SEQ ID NO: 98 >YP_001835692 [Streptococcus agalactiae A909]
MENHRYEDEGKFQRKMTSRHLFMLSLGGVIGTGLFLSSGYTIAQAGPLGAVLSYLIGAVVVYLVM
LSLGELAVAMPVTGSFHTYATKFISPGTGFTVAWLYWICWTVALGTEFLGAAMLQRWFPDVPAW
AFASFFALVIFGLNALSVRFFAEAESFFSSIKVIAIIFIILGLGAMFGLVSFEGQHKAILFTHL
TANGDFPNGIVAVVSVMLAVNYAFSGTELIGIAAGETDNPKEAVPRAIKTTIGRLVVFFVLTIVV
LASLLPMKEAGVSTAPFVDVFDKMGVPFAADIMNFVILTAILSAGNSGLYASSRMLWSLANEGML
SKSVVKINKHGVPMRALLLSMAGAVLSLFSSIYAADTVYLALVSIAGFAVVVVWLAIPVAQINFR
KEFLKENRLEDLSYKTPFTPVLPYITIVLLLISIVGIAWDSSQRAGLYFGVPFIILCYIYHKLRY

FIG. 1 (continued)

SEQ ID NO: 99   GYTIAQAGPLGAVLSYLIGA

SEQ ID NO: 100  ALGTEFLGAAMLMQRWFPDVPAWA

SEQ ID NO: 101  MFGLVSFEGQHKAILFTHLTANGDFPNGIVAVVS

SEQ ID NO: 102  LLPMKEAGVSTAPFVDVFDKMGVPFAADIMNF

SEQ ID NO: 103  SIYAADTVYLALVS

SEQ ID NO: 104  GIAWDSSQRAGL

SEQ ID NO: 105  KTW>NP_269699 [Streptococcus pyogenes M1 GAS]
MSIKEQTDNNELENGMVRGLENRHVQLIAIAGTIGTGLFLGAGRSIALTGPSIIFVYMITGAFMF
MMMRAIGEMLYYDPDQHTFINFISKYIGPGWGYFSGLSYWISLIFIGMAEITAVGAYVQFWFPSW
PAWLIQLVFLVLLSSINLIAVRVFGETEFWFAMIKILAILALIATAIFMVLTGFETHTGHASLSN
IFDHFSMFPNGKLKFFMAFQMVFFAYQAIEFVGITTSETANPRKVLPKAIQEIPTRIVIFYVGAL
VSIMAIVPWHQLPVDESPFVMVFKLIGIKWAAALINFVVLTSAASALNSTLYSTGRHLYQIANET
PNALTNRLKINTLSRQGVPSRAIIASAVVVGISALINILPGVADAFSLITASSSGVYIAIYALTM
IAHWKYRQSKDFMADGYLMPKYKVTTPLTLAFFAFVFISLFLQESTYIGAIGATIWIIIFGIYSN
VKFK

SEQ ID NO: 106  LGAGRSIALTGPSIIF

SEQ ID NO: 107  GMAEITAVGAYVQFWFPSWPAWL

SEQ ID NO: 108  MVLTGFETHTGHASLSNIFDHFSMFPNGKLKFF

SEQ ID NO: 109  WHQLPVDESPFVMVFKLIGIKWAA

SEQ ID NO: 110  INILPGVADAFSL

SEQ ID NO: 111  FLQESTYI

FIG. 2

| GCP PROTEIN SEQUENCES |
|---|

SEQ ID NO: 112 >YP_016869 [Bacillus anthracis str. 'Ames Ancestor']
MEKNTIILGIETSCDETAVAVVKNGTEIIANVVASQIESHKRFGGVVPEIASRHHVEEITVVLEE
ALKEANITFDDIDAIAVTEGPGLVGALLIGVNAAKAVAFAHDIPLVGVHHIAGHIYANRLVKEVQ
FPLLSLVVSGGHTELVYMKEHGSFEVIGETRDDAAGEAYDKVARTLSMPYPGGPHIDRLAHEGKP
TIDLPRAWLEPDSYDFSFSGLKSAVINTVHNAKQRGIEIAPEDLAASFQESVIDVLVTKASRAAD
AYNVKQVLLAGGVAANKGLRARLETEFAQKENVELIIPPLSLCTDNAAMIAAAGTIAYEQGKRAT
LALNANPGLDIEA SEQ ID NO: 113 >YP_001077571 [Burkholderia mallei NCTC 10247]
MRTRASMRPPHTIMLVLGIESSCDETGLALYDTERGLLAHALHSQIAMHREYGGVVPELASRDHI
RRALPLLEEVLAASGARRDDIDAIAFTQGPGLAGALLVGASIANALAFAWDKPTIGIHHLEGHLL
SPLLVAEPPPFPFVALLVSGGHTQLMRVSDVGVYETLGETLDDAAGEAFDKTAKLLGLGYPGGPE
VSRLAEAGTPGAVVLPRPMLHSGDLDFSFSGLKTAVLTQMKKLEAAHAGGAVLERAKADLARGFV
DAAVDVLVAKSLAALKATRLKRLVVAGGVGANRQLRAALSAAAQKRGFDVHYPDLALCTDNGAMI
ALAGALRLARWPSQASRDYAFTVKPRWDLASLAR SEQ ID NO: 114
IANALAFAWDKPTIGIHHLEGHLLSPLLVAEPPPFPFVALLVSGGHTQLMRVSDVGVYETLGETL
DDAAGEAFDKTAKLLGLGYPGGPEVSRLAEAGTPGAVVLPRPMLHSGDLDFSFSGLKTAVLTQMK
KLEAAHAGGAVLERAKADLARGFVDAAVDVLVAKSLAALKATRLKRLVVAGGVGANRQLRAALSA
AAQKRGFDVHYPDLALCTDNGAMIALAGALRLARWPSQASRDYAFTVKPRWDLASLAR SEQ ID NO: 115 >ZP_02494705 [Burkholderia pseudomallei NCTC 13177]
MRTRASMRPPHTIMLVLGIESSCDETGLALYDTERGLLAHALHSQIAMHREYGGVVPELASRDHI
RRALPLLEEVLAASGARRDDIDAIAFTQGPGLAGALLVGASIANALAFAWDKPTIGIHHLEGHLL
SPLLVAEPPPFPFVALLVSGGHTQLMRVSDVGVYETLGETLDDAAGEAFDKTAKLLGLGYPGGPE
VSRLAEAGTPGAVVLPRPMLHSGDLDFSFSGLKTAVLTQMKKLEAAHAGGAVLERAKADLARGFV
DAAVDVLVAKSLAALKTTRLKRLVVAGGVGANRQLRAALSAAAQKRGFDVHYPDLALCTDNGAMI
ALAGALRLTRWPSQASRDYAFTVKPRWDLASLAR SEQ ID NO: 116
PGLAGALLVGASIANALAFAWDKPTIGIHHLEGHLLSPLLVAEPPPFPFVALLVSGGHTQLMRVS
DVGVYETLGETLDDAAGEAFDKTAKLLGLGYPGGPEVSRLAEAGTPGAVVLPRPMLHSGDLDFSF
SGLKTAVLTQMKKLEAAHAGGAVLERAKADLARGFVDAAVDVLVAKSLAALKTTRLKRLVVAGGV
GANRQLRAALSAAAQKRGFDVHYPDLALCTDNGAMIALAGALRLTRWPSQASRDYAFTVKPRWDL
ASLAR SEQ ID NO: 117 >ADI50873 [Chlamydia trachomatis D-EC]
MFAMLTLGLESSCDETSCSLVQNGKILANKIASQDIHASYGGVIPELASRAHLQTFPELLTAATQ
SAGVSLEDIELISVANTPGLIGALSIGVNFAKGLASGLKRPLIGVNHVEAHLYAACMEAPATQFP
ALGLAISGAHTSLFLMPDATTFLLIGKTRDDAIGETFDKVARFLGLPYPGGQKLEELAREGDADA
FAFSPARVSGYDFSFSGLKTAVLYALKGNNSSAKAPFFEVSETQKRNIAASFQKAVFMTIAQKLP
DIVKTFSCESLIVGGGVANNSYFRRLLNQICSLPIYFPSSQLCSDNAAMIAGLGERLFCNRTHVS
KEVIPCARYQWESACS

FIG. 2 (continued)

SEQ ID NO: 118 >YP_002805829 [Clostridium botulinum A2 str. Kyoto]
MKESINILAIESSCDETSAAVVVNGREVLSNIIASQISTHEKFGGVVPEVASRKHIEVISAVVQE
ALDEANFTLDDIDAIGVTYGPGLVGALLVGLQYAKGLAFATGKPLIGVNHIEGHISANFIEYKDL
KPPFMCLVVSGGHTFIVYMKDYGEFEVLGETRDDAAGEAFDKVARAIGLGYPGGPKIDKISKEGN
EEAIKFPRANFHNDTLDFSFSGIKSAVLNYLNKKEMKGEEINKADVAASFQKSVVDVLVDNTIKA
CMSKKVDKIAVAGGVASNSCLRETLVRECKKKGIEVLIPPFILCTDNAAMIGSAAYFEYIKGRST
SLDINAVPNLKLGER SEQ ID NO: 119 >ZP_05328289 [Clostridium difficile QCD-63q42]
MSDIITLAIESSCDETAASVLKNGREILSNIISTQIETHKKFGGVVPEVASRKHVENIDIVVQEA
LDKANIGFNDIDHIAVTYGPGLVGALLVGLSYAKALAYTLNIPLVGVNHIEGHLSANYIEHKDLK
PPFITLIVSGGHTHLVEVKDYGKYEILGKTRDDASGEAFDKISRAMNLGYPGGPIIDNLAKNGNK
HAIEFPRAYLEEDSYDFSFSGLKSSVLNYLNGKRMKNEEIVVEDVAASFQEAVVEVLSTKALKAV
KDKGYNIITLSGGVASNSGLRAKITELAKDNGITVKYPPLILCTDNAAMIGCAGYYNFINGKTHD
MSLNAVPNLKINQ SEQ ID NO: 120 >ZP_05559193 [Enterococcus faecalis T8]
MTIFTKERKLLLAVESSCDETSVAVIEDGDKILSNIVASQIKSHQRFGGVVPEVASRHHVEQVTI
CIEEALTEAKVTPEELSGVAVTYGPGLVGALLIGLSAAKAFAWAHQLPLIPVNHMAGHIYAARFV
APLEFPLMALLVSGGHTELVYMKEDGSFEIVGETRDDAAGEAYDKVGRVLGLPYPSGKEIDALAH
EGTDTYQFPRAMLKEDNYDFSFSGLKSAFINTVHNAEQRGEALSTKDLAASFQASVVEVLVTKTI
RACQEYPVKQLLIAGGVAANQGLREAMRHAISEQLPEVTLLIPPLKLCGDNAAMIGAAAFIEAEK
NHFASYNLNAEPGVSFMTISEEG SEQ ID NO: 121 LIGLSAAKAFAWAHQLPLIPVNHMAGHIYAARFVAPLEFPLMALLVSGGH
SEQ ID NO: 122 >NP_417536 [Escherichia coli str. K-12 substr. MG1655]
MRVLGIETSCDETGIAIYDDEKGLLANQLYSQVKLHADYGGVVPELASRDHVRKTVPLIQAALKE
SGLTAKDIDAVAYTAGPGLVGALLVGATVGRSLAFAWDVPAIPVHHMEGHLLAPMLEDNPPEFPF
VALLVSGGHTQLISVTGIGQYELLGESIDDAAGEAFDKTAKLLGLDYPGGPLLSKMAAQGTAGRF
VFPRPMTDRPGLDFSFSGLKTFAANTIRDNGTDDQTRADIARAFEDAVVDTLMIKCKRALDQTGF
KRLVMAGGVSANRTLRAKLAEMMKKRRGEVFYARPEFCTDNGAMIAYAGMVRFKAGATADLGVSV
RPRWPLAELPAA SEQ ID NO: 123
ATVGRSLAFAWDVPAIPVHHMEGHLLAPMLEDNPPEFPFVALLVSGGHTQLISVTGIGQYELLGE
SIDDAAGEAFDKTAKLLGLDYPGGPLLSKMAAQGTAGRFVFPRPMTDRPGLDFSFSGLKTFAANT
IRDNGTDDQTRADIARAFEDAVVDTLMIKCKRALDQTGFKRLVMAGGVSANRTLRAKLAEMMKKR
RGEVFYARPEFCTDNGAMIAYAGMVRFKAGATADLGVSVRPRWPLAELPAA SEQ ID NO: 124 >ZP_01789247 [Haemophilus influenzae 3655]
MKILGIETSCDETGVAIYDEEKGLIANQLYTQIALHADYGGVVPELASRDHIRKTAPLIKAALEE
AKITASDIDGIAYTSGPGLVGALLVGATIARSLAYAWNVPAIGVHHMEGHLLAPMLDKNSPHFPF
VALLVSGGHTQLVRVDGVGKYEVIGESIDDAAGEAFDKTAKLLGLDYPGGAALSRLAEKGAPNRF
TFPRPMTDRAGLDFSFSGLKTFAANTINQAIKNEGKLTEQIKADIAYAFQDAVVDTLAIKCKRAL
KETGYKRLVIAGGVSANKKLRESLAHLMQNLGGEVFYPQPQFCTDNGAMIAYTGFLRLKQGQHSD
LAIDVKPRWAMTELEAI SEQ ID NO: 125
IARSLAYAWNVPAIGVHHMEGHLLAPMLDKNSPHFPFVALLVSGGHTQLVRVDGVGKYEVIGESI
DDAAGEAFDKTAKLLGLDYPGGAALSRLAEKGAPNRFTFPRPMTDRAGLDFSFSGLKTFAANTIN
QAIKNEGKLTEQIKADIAYAFQDAVVDTLAIKCKRALKETGYKRLVIAGGVSANKKLRESLAHLM
QNLGGEVFYPQPQFCTDNGAMIAYTGFLRLKQGQHSDLAIDVKPRWAMTELEAI

FIG. 2 (continued)

SEQ ID NO: 126 >AD006253 [Helicobacter pylori Sat464]
MILSIESSCDDSSLALTRIKDAKLIAHFKISQEKHHSSYGGVVPELASRLHAENLPLLLERIKIS
LNKDFSKLKAIAITNQPGLSVTLIEGLMMAKALSLSLNLPLILEDHLRGHVYSLFINEKQTCMPL
SALLVSGGHSLILEARDYEDIKIVATSLDDSFGESFDKVSKMLDLGYPGGPIVEKLALDYAHQNE
PLMFPVPLKNSQNLAFSFSGLKNAVRLEVEKNAPNLNEAIKQKISYHFQSAAIEHLIQQTKRYFK
IKRPKIFGIVGGASQNLALRKAFENLCDEFDCKLVLAPLEFCSDNAAMIGRSSLEAYQQKRFVSL
EKANISPRTLLKSFE SEQ ID NO: 127 >NP_217936 [Mycobacterium tuberculosis H37Rv]
MTTVLGIETSCDETGVGIARLDPDGTVTLLADEVASSVDEHVRFGGVVPEIASRAHLEALGPAMR
RALAAAGLKQPDIVAATIGPGLAGALLVGVAAAKAYSAAWGVPFYAVNHLGGHLAADVYEHGPLP
ECVALLVSGGHTHLLHVRSLGEPIIELGSTVDDAAGEAYDKVARLLGLGYPGGKALDDLARTGDR
DAIVFPRGMSGPADDRYAFSFSGLKTAVARYVESHAADPGFRTADIAAGFQEAVADVLTMKAVRA
ATALGVSTLLIAGGVAANSRLRELATQRCGEAGRTLRIPSPRLCTDNGAMIAAFAAQLVAAGAPP
SPLDVPSDPGLPVMQGQVR SEQ ID NO: 128
AAAKAYSAAWGVPFYAVNHLGGHLAADVYEHGPLPECVALLVSGGHTHLLHVRSLGEPIIELGST
VDDAAGEAYDKVARLLGLGYPGGKALDDLARTGDRDAIVFPRGMSGPADDRYAFSFSGLKTAVAR
YVESHAADPGFRTADIAAGFQEAVADVLTMKAVRAA

SEQ ID NO: 129 AGAPPSPLDVPSDPGLPVMQGQVR

SEQ ID NO: 130 >ZP_04740160 [Neisseria gonorrhoeae SK-93-1035]
MLVLGIESSCDETGVALYDTERGLRSHCLHTQMAMHAEYGGVVPELASRDHIRRLVPLTEGCLAQ
AGASYGDIDAVAFTQGPGLGGALLAGSSYANALALALDKPVIPVHHLEGHLLSPLLAEEKPDFPF
VALLVSGGHTQIMAVRDIGDYELLGESVDDAAGEAFDKTAKLLGLPYPGGAKLSELAESGRPEAF
VFPRPMIHSDDLQMSFSGLKTAVLTAVEKVREANGSETIPEQTRNNICRAFQDAVVEVLEAKVKK
ALLQTGFRTVVVAGGVGANRKLRETFGNMTVQIPTPKGKPKHPSEKVSVFFPPMAYCTDNGAMIA
FAGAMHLGKGREVGAFNVRPRWSLSEIVK SEQ ID NO: 131 >CBA05640 [Neisseria meningitidis alpha153]
MLVLGIESSCDETGVALYDTERGLRAHCLHTQMAMHAEYGGVVPELASRDHIRRLVPLTEGCLAQ
AGASYGDIDAVAFTQGPGLGGALLAGSSYANALAFALDKPVIPVHHLEGHLLSPLLAEEKPDFPF
VALLVSGGHTQIMAVKGIGDYELLGESVDDAAGEAFDKTAKLLGLPYPGGAKLSELAESGRPEAF
VFPRPMIHSDDLQMSFSGLKTAVLTAVEKVRAENGADDIPEQTRNDICRAFQDAVVDVLEAKVKK
ALLQTGFRTVVVAGGVGANRKLRETFGNMTVQIPTPKGKPKHPSEKVSVFFPPTAYCTDNGAMIA
FAGAMHLGKGREVGAFNVRPRWPLSEIVK SEQ ID NO: 132 >NP_249271 [Pseudomonas aeruginosa PA01]
MRVLGLETSCDETGVALYDSERGLLADALFSQIDLHRVYGGVVPELASRDHVKRMLPLIRQVLDE
SGCTPADIDAIAYTAGPGLVGALLVGASCAQAMAFAWGVPAVGVHHMEGHLLAPMLEEQPPRFPF
VALLVSGGHTQLVRVDGIGRYQLLGESVDDAAGEAFDKTAKLIGLYPGGPEIARLAERGTPGRF
VFPRPMTDRPGLDFSFSGLKTFTLNTWQRCVEAGDDSEQTRCDIALAFQTAVVETLLIKCRRALK
QTGLKNLVIAGGVSANQALRSGLEKMLGEMKGQVFYARPRFCTDNGAMIAYAGCQRLLAGQHDGP
AISVQPRWPMESLPAV SEQ ID NO: 133
FAWGVPAVGVHHMEGHLLAPMLEEQPPRFPFVALLVSGGHTQLVRVDGIGRYQLLGESVDDAAGE
AFDKTAKLIGLYPGGPEIARLAERGTPGRFVFPRPMTDRPGLDFSFSGLKTFTLNTWQRCVEAG
DDSEQTRCDIALAFQTAVVETLLIKCRRALKQTGLKNLVIAGGVSANQALRSGLEKMLGEMKGQV
FYARPRFCTDNGAMIAYAGCQRLLAGQHDGPAISVQPRWPMESLPAV

FIG. 2 (continued)

SEQ ID NO: 134 >NP_708874 [Shigella flexneri 2a str. 301]
MRVLGIETSCDETGIAIYDDEKGLLANQLYSQVKLHADYGGVVPELASRDHVRKTVPLIQAALKE
SGLTAKDIDAVAYTAGPGLVGALLVGATVGRSLAFAWNVPAIPVHHMEGHLLAPMLEDNPPEFPF
VALLVSGGHTQLISVTGIGQYELLGESIDDAAGEAFDKTAKLLGLDYPGGPLLSKMAAQGTAGRF
VFPRPMTDRPGLDFSFSGLKTFAANTIRDNGTDDQTRADIARAFEDAVVDTLMIKCKRALDQTGF
KRLVMAGGVSANRTLRAKLAEMMKKRRGEVFYARPEFCTDNGAMIAYAGMVRFKAGATADLGVSV
RPRWPLAELPAA SEQ ID NO: 135
VGRSLAFAWNVPAIPVHHMEGHLLAPMLEDNPPEFPFVALLVSGGHTQLISVTGIGQYELLGESI
DDAAGEAFDKTAKLLGLDYPGGPLLSKMAAQGTAGRFVFPRPMTDRPGLDFSFSGLKTFAANTIR
DNGTDDQTRADIARAFEDAVVDTLMIKCKRALDQTGFKRLVMAGGVSANRTLRAKLAEMMKKRRG
EVFYARPEFCTDNGAMIAYAGMVRFKAGATADLGVSVRPRWPLAELPAA SEQ ID NO: 136 >ZP_01816852 [Streptococcus pneumoniae SP3-BS71]
MKDRYILAFETSCDETSVAVLKNDDELLSNVIASQIESHKRFGGVVPEVASRHHVEVITACIEEA
LAEAGITEEDVTAVAVTYGPGLVGALLVGLSAAKAFAWAHGLPLIPVNHMAGHLMAAQSVEPLEF
PLLALLVSGGHTELVYVSEAGDYKIVGETRDDAVGEAYDKVGRVMGLTYPAGREIDELAHQGQDI
YDFPRAMIKEDNLEFSFSGLKSAFINLHHNAEQKGESLSTEDLCASFQAAVLDILMAKTKKALEK
YPVKTLVVAGGVAANKGLRERLAAEVTDVKVIIPPLRLCGDNAGMIAYASVSEWNKENFANLDLN
AKPSLAFDTME SEQ ID NO: 137
AAKAFAWAHGLPLIPVNHMAGHLMAAQSVEPLEFPLLALLVSGGHTELVYVSEAGDYKIVGETRD
DAVGEAYDKVGRVMGLTYPAGREIDELAHQGQDIYDFPRAMIKEDNLEFSFSGLKSAFINLHHNA
EQKGESLSTEDLCASFQAAVLDILMAKTKKALEKYPVKTLVVAGGVAANKGLRERLAAEVTDVKV
IIPPLRLCGDNAGMIAYASVSEWNKENFANLDLNAKPSLAFDTME SEQ ID NO: 138 >AE013956_7 [Yersinia pestis KIM 10]
MMGNVMRVLGIETSCDETGIAVYDDKAGLLANQLYSQVKLHADYGGVVPELASRDHVRKTVPLIQ
AALKEANLSAKDIDAVAYTAGPGLVGALLVGATIGRALAFAWGVPAVPVHHMEGHLLAPMLEENA
PEFPFVALLVSGGHTQLISVTGIGEYLLLGESVDDAAGEAFDKTAKLLGLDYPGGPMLSRMAQQG
TVGRFTFPRPMTDRPGLDFSFSGLKTFAANTIRANGDDDQTRADIARAFEDAVVDTLAIKSKRAL
DQTGFKRLVIAGGVSANQTLRLKLADMMQKRGGEVFYARPEFCTDNGAMIAYAGMVRLRSNLNSE
LSVSVRPRWPLSELPKV SEQ ID NO: 139
RALAFAWGVPAVPVHHMEGHLLAPMLEENAPEFPFVALLVSGGHTQLISVTGIGEYLLLGESVDD
AAGEAFDKTAKLLGLDYPGGPMLSRMAQQGTVGRFTFPRPMTDRPGLDFSFSGLKTFAANTIRAN
GDDDQTRADIARAFEDAVVDTLAIKSKRALDQTGFKRLVIAGGVSANQTLRLKLADMMQKRGGEV
FYARPEFCTDNGAMIAYAGMVRLRSNLNSELSVSVRPRWPLSELPKV SEQ ID NO: 140 >NP_688747 [Streptococcus agalactiae 2603V/R]
MKDRYILAVESSCDETSVAILKNDKELLANIIASQVESHKRFGGVVPEVASRHHVEVVTTCFEDA
LQEAGIVASDLDAVAVTYGPGLVGALLVGMAAAKAFAWANKLPLIPINHMAGHLMAARDVKELQY
PLLALLVSGGHTELVYVSEPGDYKIVGETRDDAVGEAYDKVGRVMGLTYPAGREIDQLAHKGQDT
YHFPRAMIKEDHLEFSFSGLKSAFINLHHNAEQKGEALVLEDLCASFQAAVLDILLAKTQKALLK
YPVKTLVVAGGVAANQGLRERLATDISPDIDVVIPPLRLCGDNAGMIALAAAIEFEKENFASLKL
NAKPSLAFESL

FIG. 2 (continued)

SEQ ID NO: 141
AAAKAFAWANKLPLIPINHMAGHLMAARDVKELQYPLLALLVSGGHTELVYVSEPGDYKIVGETR
DDAVGEAYDKVGRVMGLTYPAGREIDQLAHKGQDTYHFPRAMIKEDHLEFSFSGLKSAFINLHHN
AEQKGEALVLEDLCASFQAAVLDILLAKTQKALLKYPVKTLVVAGGVAANQGLRERLATDISPDI
DVVIPPLRLCGDNAGMIALAAAIEFEKENFASLKLNAKPSLAFESL

SEQ ID NO: 142 >YP_060920 [Streptococcus pyogenes MGAS10394]
MTDRYILAVESSCDETSVAILKNESTLLSNVIASQVESHKRFGGVVPEVASRHHVEVITTCFEDA
LQEAGISASDLSAVAVTYGPGLVGALLVGLAAAKAFAWANHLPLIPVNHMAGHLMAAREQEPLVY
PLIALLVSGGHTELVYVPEPGDYHIIGETRDDAVGEAYDKVGRVMGLTYPAGREIDQLAHKGQDT
YHFPRAMITEDHLEFSFSGLKSAFINLHHNAKQKGNELILEDLCASFQAAVLDILLAKTKKALSR
YPAKMLVVAGGVAANQGLRDRLAQEITHIEVVIPKLRLCGDNAGMIALAAAIEYDKQHFANMSLN
AKPSLAFDQFPDSFVIN SEQ ID NO: 143
AAAKAFAWANHLPLIPVNHMAGHLMAAREQEPLVYPLIALLVSGGHTELVYVPEPGDYHIIGETR
DDAVGEAYDKVGRVMGLTYPAGREIDQLAHKGQDTYHFPRAMITEDHLEFSFSGLKSAFINLHHN
AKQKGNELILEDLCASFQAAVLDILLAKTKKALSRYPAKMLVVAGGVAANQGLRDRLAQEITHIE
VVIPKLRLCGDNAGMIALAAAIEYDKQHFANMSLNAKPSLAFDQFPDSFVIN

FIG. 3

DivIB HOMOLOG PROTEIN SEQUENCES

SEQ ID NO: 144 >YP_020689 [Bacillus anthracis str. 'Ames Ancestor']
MKNSKVIKLQDRVPKLKNQQKKKKKNVNHRLILYISILFLLVLFLIYFRSPLSNIKKISVFGNHY
MTDEQVMKESGVTYDTSYFRVTAHKAEENLTKRKEIKAVNVKKRFPNKIDVHIEEYLTIGYINKD
GKLQPLLENGKTLDVLPNGKLPVAAPIFEPFKEEKMKELIAELEKLTPTILRSISEIRYSPTNAN
EDHLTLYMNEGYEVSTTIQNFAKRMETYPLILKTIEPGKKVLIDLEVGAYTKELGAEEKKNRMIV
FNTLS SEQ ID NO: 145
IYFRSPLSNIKKISVFGNHYMTDEQVMKESGVTYDTSYFRVTAHKAEENLTKRKEIKAVNVKKRF
PNKIDVHIEEYLTIGYINKDGKLQPLLENGKTLDVLPNGKLPVAAPIFEPFKEEKMKELIAELEK
LTPTILRSISEIRYSPTNANEDHLTLYMNEGYEVSTTIQNFAKRMETYPLILKTIEPGKKVLIDL
EVGAYTKELGAEEKKNRMIVFNTLS SEQ ID NO: 146 >YP_001786884 [Clostridium botulinum A3 str. Loch Maree]
MSKDLISTDEYIKIKKKRKRIKKIVVLFIFLISILVTLCLKIPYFNIESIEIKGNVNIPKEIIKD
SSTIKTGNNIFYTNKKDAIENISLNPYIEEVKITKKLPNKLEIYVKEREALFYNKVDKDFFIISK
NGCLLEKRKEIKNMKLINLQGFEFNESKIGSALKAKDERGVKILNDFGVLLKNNASDVIFTQLDL
RNLLDIRIYSNGICVKIGTSDQIEKKLNTAINILKRDELKKAKKGYVDVSYEGNPVFYIEK SEQ ID NO: 147
CLKIPYFNIESIEIKGNVNIPKEIIKDSSTIKTGNNIFYTNKKDAIENISLNPYIEEVKITKKLP
NKLEIYVKEREALFYNKVDKDFFIISKNGCLLEKRKEIKNMKLINLQGFEFNESKIGSALKAKDE
RGVKILNDFGVLLKNNASDVIFTQLDLRNLLDIRIYSNGICVKIGTSDQIEKKLNTAINILKRDE
LKKAKKGYVDVSYEGNPVFYIEK SEQ ID NO: 148 >YP_001089161 [Clostridium difficile 630]
MKKRRKLNTNNVMIILVFILMLSFCICIIVKSDLFDVKKIDVIGNKRVTKSNIMKELNVNLNENI
FAYNFKDMKNKLIKNPYIENVEIKRKLPNKIIISLKEKEIFAVLKDEDNYCYIDKKGNLLEELRG
SNESKKDLIVDVDYSIDDNKSIKFKNYKTKENVFKTLNYLKEEGIYRKINYVNLKKESNIEMLTR
SNIKILLSNDDNLDYNISRVSKILIDLQNKNTNGGTINLNYGKLAVYSPEG SEQ ID NO: 149
IIVKSDLFDVKKIDVIGNKRVTKSNIMKELNVNLNENIFAYNFKDMKNKLIKNPYIENVEIKRKL
PNKIIISLKEKEIFAVLKDEDNYCYIDKKGNLLEELRGSNESKKDLIVDVDYSIDDNKSIKFKNY
KTKENVFKTLNYLKEEGIYRKINYVNLKKESNIEMLTRSNIKILLSNDDNLDYNISRVSKILIDL
QNKNTNGGTINLNYGKLAVYSPEG SEQ ID NO: 150 >ZP_05474765 [Enterococcus faecalis ATCC 4200]
MWKISNENDIFKKRKPLPPKKSEESQPELTPWQKQNQEYLKKQAEEAASKGENEQAEVTITLQEQ
SQEEPQQHLPQETVEEEEHFADRLPNVKKTRNKRLYRRLAFILTCLGTAILVALYFVSPLSRLSE
VTVSGNKSVESQAIIQQSKLETGSGLWEQYSNRNYFSANIQKKFPIIKKANIKLNGINSFKIDIQ
EYQIVALAATKGGYHPILENGKTLAETTKAAESGKPIFENFKEDKLIPELMASYNKLPQEIKQGI
SEIKYAPSKTNKDLINVYMNDGNRVIVNISDLSEKMAYYSQVAEQMDKPGIVDMEVGIFSYPYEK
ESEETGSEVSEDSAAENQEVVDPNAGVATDEANNGTPTNGENQEVQQAE

FIG. 3 (continued)

SEQ ID NO: 151
FVSPLSRLSEVTVSGNKSVESQAIIQQSKLETGSGLWEQYSNRNYFSANIQKKFPIIKKANIKLN
GINSFKIDIQEYQIVALAATKGGYHPILENGKTLAETTKAAESGKPIFENFKEDKLIPELMASYN
KLPQEIKQGISEIKYAPSKTNKDLINVYMNDGNRVIVNISDLSEKMAYYSQVAEQMDKPGIVDME
VGIFSYPYEKESEETGSEVSEDSAAENQEVVDPNAGVATDEANNGTPTNGENQEVQQAE

SEQ ID NO: 152 >ZP_02707868 [Streptococcus pneumoniae CDC1873-00]
MSKDKKNEDKETLEELKELSEWQKRNQEYLKKKAEEEAALAEEKEKERQARMGEESEKSEDKQDQ
ESETDQEDSESAKEESEEKVASSEADKEKEEKEESESKEKEEQDKKLAKKATKEKPAKAKIPGIH
ILRAFTILFPSLLLLIVSAYLLSPYATMKDIRVEGTVQTTADDIRQVSGIQDSDYTINLLLDKAK
YEKQIKSNYWVESAQLVYQFPTKFTIKVKEYDIVAYYISGENHYPILSSGQLETSSVSLNSLPET
YLSVLFNDSEQIKVFVSELAQISPELKAAIQKVELAPSKVTSDLIRLTMNDSDEVLVPLSEMSKK
LPYYSKIKPQLSEPSVVDMEAGIYSYTVADKLIMEAEEKAKQEAKEAEKKQEEEQKKQEEESNRN
QTTQRSSRR SEQ ID NO: 153
LIVSAYLLSPYATMKDIRVEGTVQTTADDIRQVSGIQDSDYTINLLLDKAKYEKQIKSNYWVESA
QLVYQFPTKFTIKVKEYDIVAYYISGENHYPILSSGQLETSSVSLNSLPETYLSVLFNDSEQIKV
FVSELAQISPELKAAIQKVELAPSKVTSDLIRLTMNDSDEVLVPLSEMSKKLPYYSKIKPQLSEP
SVVDMEAGIYSYTVADKLIMEAEEKAKQEAKEAEKKQEEEQKKQEEESNRNQTTQRSSRR SEQ ID NO: 154 >NP_687507 [Streptococcus agalactiae 2603V/R]
MPKKKSDTPEKEEVVLTEWQKRNLEFLKKRKEDEEEQKRINEKLRLDKRSKLNISSPEEPQNTTK
IKKLHFPKISRPKIEKKQKKEKIVNSLAKTNRIRTAPIFVVAFLVILVSVFLLTPFSKQKTITVS
GNQHTPDDILIEKTNIQKNDYFFSLIFKHKAIEQRLAAEDVWVKTAQMTYQFPNKFHIQVQENKI
IAYAHTKQGYQPVLETGKKADPVNSSELPKHFLTINLDKEDSIKLLIKDLKALDPDLISEIQVIS
LADSKTTPDLLLLDMHDGNSIRIPLSKFKERLPFYKQIKKNLKEPSIVDMEVGVYTTTNTIESTP
VKAEDTKNKSTDKTQTQNGQVAENSQGQTNNSNTNQQGQQIATEQAPNPQNVN SEQ ID NO: 155
LLTPFSKQKTITVSGNQHTPDDILIEKTNIQKNDYFFSLIFKHKAIEQRLAAEDVWVKTAQMTYQ
FPNKFHIQVQENKIIAYAHTKQGYQPVLETGKKADPVNSSELPKHFLTINLDKEDSIKLLIKDLK
ALDPDLISEIQVISLADSKTTPDLLLLDMHDGNSIRIPLSKFKERLPFYKQIKKNLKEPSIVDME
VGVYTTTNTIESTPVKAEDTKNKSTDKTQTQNGQVAENSQGQTNNSNTNQQGQQIATEQAPNPQN
VN SEQ ID NO: 156 >NP_664978 [Streptococcus pyogenes MGAS315]
MAKDKEKQSDDKLVLTEWQKRNIEFLKKKQQAEEEKKLKEKLLSDKKAQQQAQNASEAVELKTD
EKTDSQEIESETTSKPKKTKKVRQPKEKSATQIAFQKSLPVLLGALLLMAVSIFMITPYSKKKEF
SVRGNHQTNLDELIKASKVKASDYWLTLLISPGQYERPILRTIPWVKSVHLSYQFPNHFLFNVIE
FEIIAYAQVENGFQPILENGKRVDKVRASELPKSFLILNLKDEKAIQQLVKQLTTLPKKLVKNIK
SVSLANSKTTADLLLIEMHDGNVVRVPQSQLTLKLPYYQKLKKNLENDSIVDMEVGIYTTTQEIE
NQPEVPLTPEQNAADKEGDKPGEHQEQTDNDSETPANQSSPQQAPPSPETVLEQAHG SEQ ID NO: 157
IFMITPYSKKKEFSVRGNHQTNLDELIKASKVKASDYWLTLLISPGQYERPILRTIPWVKSVHLS
YQFPNHFLFNVIEFEIIAYAQVENGFQPILENGKRVDKVRASELPKSFLILNLKDEKAIQQLVKQ
LTTLPKKLVKNIKSVSLANSKTTADLLLIEMHDGNVVRVPQSQLTLKLPYYQKLKKNLENDSIVD
MEVGIYTTTQEIENQPEVPLTPEQNAADKEGDKPGEHQEQTDNDSETPANQSSPQQAPPSPETVL
EQAHG

FIG. 4

DivIC PROTEIN SEQUENCES

SEQ ID NO: 158 >YP_016662 [Bacillus anthracis str. 'Ames Ancestor']
MRELRQRTIEKQSPNPVKEHIIQTDENRKRLYRRLAVFLVFAFTIIASISVTFYQQNSSIKAKEA
KVKDMKKELDSLTNKEKSLKDEVQKLNDEEYVLKIARRDYFFSGKGEIIFPVSK SEQ ID NO: 159
TFYQQNSSIKAKEAKVKDMKKELDSLTNKEKSLKDEVQKLNDEEYVLKIARRDYFFSGKGEIIFP
VSK SEQ ID NO: 160 >YP_001256011 [Clostridium botulinum A str. ATCC 3502]
MKKINVKKLIFFLAIVYSTVIFINQQITMHKIRDQISEKKIELKEVKEKNQKLQDEVKLSKSKDY
IEKLARERLRLIKKGETPVINNTQ

SEQ ID NO: 161
ITMHKIRDQISEKKIELKEVKEKNQKLQDEVKLSKSKDYIEKLARERLRLIKKGETPVINNTQ

SEQ ID NO: 162 >ZP_03985954 [Enterococcus faecalis HH22]
MGKNEKSSKKVAALENDYTKEQYVEFQKQQKQLIFRRRRLAAIFLVAFIIFAFSGIQLMKDYHRL
GAFKQERADAIAESVAVDKKVKDLKKDVALLKDDDYVAKLARSRFLLSKEGEQIYPTPEQMKKTQ
TSGAEESKSSSEKNSQSQSSTETTKSSAE SEQ ID NO: 163
QLMKDYHRLGAFKQERADAIAESVAVDKKVKDLKKDVALLKDDDYVAKLARSRFLLSKEGEQIYP
TPEQMKKTQTSGAEESKSSSEKNSQSQSSTETTKSSAE SEQ ID NO: 164 >NP_687047 [Streptococcus agalactiae 2603V/R]
MSKPNVVQLNNQYINDENLKKRYEAEELRRKNRLMGWVLIFVMLLFILPTYNLVKSYRTLQERRQ
EVVKLTKDYQTLTNRTENQKLLAKQLKNPDYVQKYARAKYYFSKTGEMIYPLPDLLPK SEQ ID NO: 165
NLVKSYRTLQERRQEVVKLTKDYQTLTNRTENQKLLAKQLKNPDYVQKYARAKYYFSKTGEMIYP
LPDLLPK SEQ ID NO: 166 >NP_268431 [Streptococcus pyogenes M1 GAS]
MKKPSIVQLNNHYIKKENLKKKFEEEESQKRNRFMGWILVSMMFLFILPTYNLVKSYVDFEKQNQ
QVVKLKKEYNELSESTKKEKQLAERLKDDNFVKKYARAKYYLSREGEMIYPIPGLLPK SEQ ID NO: 167
NLVKSYVDFEKQNQQVVKLKKEYNELSESTKKEKQLAERLKDDNFVKKYARAKYYLSREGEMIYP
IPGL FtsL HOMOLOG PROTEIN SEQUENCES SEQ ID NO: 168 >YP_020698 [Bacillus anthracis str. 'Ames Ancestor']
MSNLAVKYKQQAQEEVQIQTPPQQMVQPKAKAKITRIEKLLYVAFIGFLLYACVAFIGNKAGLYQ
VNVEAATIEQKIVQQQKENQELQAEVEKLSRYERIAEVAKKHGLEINANNVKGLK

FIG. 4 (continued)

SEQ ID NO: 169
FIGNKAGLYQVNVEAATIEQKIVQQQKENQELQAEVEKLSRYERIAEVAKKHGLEINANNVKGLK

SEQ ID NO: 170 >ZP_07106202 [Enterococcus faecalis TUSoD Ef11]
MAELKKVNDFHYEAPEMDQPTVATEQDRKMQEETLPVPTILPKKKLKNVSLLEKLIGVVLVCATI
GIAIATIQVRTTIVQTMNDITETQAVIKEKEDNALKLEQERSELSKSDRIKDVAKKQGLENNGDN
VRTVK SEQ ID NO: 171
IATIQVRTTIVQTMNDITETQAVIKEKEDNALKLEQERSELSKSDRIKDVAKKQGLENNGDNVRT
VK SEQ ID NO: 172 >NP_687321 [Streptococcus agalactiae 2603V/R]
MTNEKRTEAVTQTLQRHIKTFSRIEKAFYGAIVITAIIMAVGIIYLQSNSLQVKQEVNQLNSKIN
DKQTEFDNAKQEVNELSNRDRITKIAKDAGLTIQNDNIYRKVD SEQ ID NO: 173
GIIYLQSNSLQVKQEVNQLNSKINDKQTEFDNAKQEVNELSNRDRITKIAKDAGLTIQNDNIYRK
VD SEQ ID NO: 174 >ZP_01819554 [Streptococcus pneumoniae SP6-BS73]
MAERMEKTGQILQMQLKRFSRVEKAFYFSIAVTTLIVAISIIFMQTKLLQVQNDLTKINAQIEEK
KTELDDAKQEVNELLRAERLKEIANSHDLQLNNENIRIAE

SEQ ID NO: 175
FMQTKLLQVQNDLTKINAQIEEKKTELDDAKQEVNELLRAERLKEIANSHDLQLNNENIRIAE

SEQ ID NO: 176 >NP_665206 [Streptococcus pyogenes MGAS315]
MLPKKFGNKPMTNEKRTQAVTNALQKRIKTFSRIEKAFYTAIIVTAITMAVSIIYLQSRKLQLQQ
EITSLNSHISDQKLELNNAKQEVNELSRRDRIIDIAGKAGLSNRNNNIKKVE

SEQ ID NO: 177
IYLQSRKLQLQQEITSLNSHISDQKLELNNAKQEVNELSRRDRIIDIAGKAGLSNRNNNIKKVE

SEQUENCE LISTING

<160> NUMBER OF SEQ ID NOS: 177

<210> SEQ ID NO 1
<211> LENGTH: 488
<212> TYPE: PRT
<213> ORGANISM: Bacillus anthracis

<400> SEQUENCE: 1

Met Asn Ser Ala Thr Asn Gln Thr Thr Ser Gln Thr Glu Thr Thr Lys
1               5                   10                  15

Gly Lys Gly Glu Leu Arg Arg Gly Leu Lys Ser Lys His Leu Thr Met
            20                  25                  30

Ile Ser Leu Gly Gly Thr Ile Gly Thr Gly Leu Phe Leu Ala Ser Gly
        35                  40                  45

-continued

```
Gly Val Ile His Ser Ala Gly Pro Gly Ala Leu Ile Ala Tyr Ala
 50                  55                  60
Ala Ile Gly Ile Met Val Tyr Phe Leu Met Thr Ser Leu Ala Glu Leu
 65                  70                  75                  80
Ala Ala Tyr Met Pro Val Thr Gly Ser Phe Ser Thr Tyr Ala Thr Lys
                 85                  90                  95
Phe Val Asp Pro Ser Leu Gly Phe Ala Leu Gly Trp Asn Tyr Trp Tyr
                100                 105                 110
Asn Trp Ala Ile Thr Ile Ala Ala Glu Leu Ala Ala Val Thr Leu Ile
                115                 120                 125
Met Lys Phe Trp Phe Pro Asp Thr Pro Ser Leu Ile Trp Ser Gly Leu
130                 135                 140
Cys Leu Ala Ile Ile Phe Leu Leu Asn Tyr Leu Ser Val Lys Gly Phe
145                 150                 155                 160
Gly Glu Ser Glu Tyr Trp Phe Ala Leu Ile Lys Val Ala Thr Ile Ile
                165                 170                 175
Ile Phe Leu Ile Val Gly Phe Met Met Ile Phe Gly Ile Met Gly Gly
                180                 185                 190
Glu Thr Val Gly Phe Lys Asn Phe Thr Val Ala Asp Ala Pro Phe Asn
            195                 200                 205
Gly Gly Ile Met Ala Ile Ile Gly Val Phe Met Ala Ala Gly Phe Ser
210                 215                 220
Phe Gln Gly Thr Glu Leu Leu Gly Val Ala Ala Gly Glu Thr Ser Asp
225                 230                 235                 240
Pro Glu Arg Asn Ile Pro Lys Ala Ile Arg Ser Ile Phe Trp Arg Ile
                245                 250                 255
Leu Leu Phe Tyr Ile Leu Ala Ile Leu Val Ile Gly Leu Leu Ile Pro
                260                 265                 270
Tyr Thr Thr Glu Ser Leu Ala Ala Ser Asp Val Thr Val Ser Pro Phe
            275                 280                 285
Thr Leu Ile Phe Glu Lys Ala Gly Val Ala Phe Ala Ala Ser Val Met
            290                 295                 300
Asn Ala Val Ile Leu Thr Ala Val Leu Ser Ala Gly Asn Ser Gly Met
305                 310                 315                 320
Tyr Ala Ser Thr Arg Met Leu Trp Asp Leu Ala Arg Gln Gly Lys Ala
                325                 330                 335
Pro Lys Phe Leu Gly Lys Leu Asp Ser Arg Gly Val Pro Val Asn Ala
                340                 345                 350
Leu Ile Val Thr Ser Ile Val Gly Ser Ile Ala Phe Ile Ala Ser Leu
                355                 360                 365
Phe Gly Asp Gly Val Val Tyr Ile Trp Leu Leu Asn Ala Ser Gly Met
            370                 375                 380
Ser Gly Phe Ile Ala Trp Val Gly Ile Ala Ile Ser His Tyr Arg Phe
385                 390                 395                 400
Arg Lys Ala Tyr Ile Ala Gln Gly Lys Asp Leu Asn Asp Leu Pro Tyr
                405                 410                 415
Arg Ala Lys Trp Phe Pro Phe Gly Pro Ile Phe Ala Phe Ala Leu Cys
            420                 425                 430
Val Ile Val Ile Leu Gly Gln Asn Tyr Gly Ala Phe Met Gly Glu Ser
            435                 440                 445
Ile Asp Trp Asn Gly Val Leu Val Ser Tyr Ile Gly Leu Pro Leu Phe
450                 455                 460
Leu Val Leu Trp Leu Gly Tyr Lys Phe Thr Lys Lys Thr Lys Val Ile
```

```
                      465                 470                 475                 480
Pro Leu Asp Lys Cys Glu Leu Lys
                485

<210> SEQ ID NO 2
<211> LENGTH: 12
<212> TYPE: PRT
<213> ORGANISM: artificial sequence
<220> FEATURE:
<223> OTHER INFORMATION: polypeptide or immunogenic fragment of Bacillus
      spp genes

<400> SEQUENCE: 2

Gly Val Ile His Ser Ala Gly Pro Gly Gly Ala Leu
1               5                   10

<210> SEQ ID NO 3
<211> LENGTH: 18
<212> TYPE: PRT
<213> ORGANISM: artificial sequence
<220> FEATURE:
<223> OTHER INFORMATION: polypeptide or immunogenic fragment of Bacillus
      spp genes

<400> SEQUENCE: 3

Leu Ala Ala Val Thr Leu Ile Met Lys Phe Trp Phe Pro Asp Thr Pro
1               5                   10                  15

Ser Leu

<210> SEQ ID NO 4
<211> LENGTH: 31
<212> TYPE: PRT
<213> ORGANISM: artificial sequence
<220> FEATURE:
<223> OTHER INFORMATION: polypeptide or immunogenic fragment of Bacillus
      spp genes

<400> SEQUENCE: 4

Met Met Ile Phe Gly Ile Met Gly Gly Glu Thr Val Gly Phe Lys Asn
1               5                   10                  15

Phe Thr Val Ala Asp Ala Pro Phe Asn Gly Gly Ile Met Ala Ile
            20                  25                  30

<210> SEQ ID NO 5
<211> LENGTH: 28
<212> TYPE: PRT
<213> ORGANISM: artificial sequence
<220> FEATURE:
<223> OTHER INFORMATION: polypeptide or immunogenic fragment of Bacillus
      spp genes

<400> SEQUENCE: 5

Ile Pro Tyr Thr Thr Glu Ser Leu Ala Ala Ser Asp Val Thr Val Ser
1               5                   10                  15

Pro Phe Thr Leu Ile Phe Glu Lys Ala Gly Val Ala
            20                  25

<210> SEQ ID NO 6
<211> LENGTH: 13
<212> TYPE: PRT
<213> ORGANISM: artificial sequence
<220> FEATURE:
<223> OTHER INFORMATION: polypeptide or immunogenic fragment of Bacillus
      spp genes

<400> SEQUENCE: 6
```

Ala Ser Leu Phe Gly Asp Gly Val Val Tyr Ile Trp Leu
1               5                   10

<210> SEQ ID NO 7
<211> LENGTH: 16
<212> TYPE: PRT
<213> ORGANISM: artificial sequence
<220> FEATURE:
<223> OTHER INFORMATION: polypeptide or immunogenic fragment of Bacillus
      spp genes

<400> SEQUENCE: 7

Gly Gln Asn Tyr Gly Ala Phe Met Gly Glu Ser Ile Asp Trp Asn Gly
1               5                   10                  15

<210> SEQ ID NO 8
<211> LENGTH: 461
<212> TYPE: PRT
<213> ORGANISM: Burkholderia mallei

<400> SEQUENCE: 8

Met Ala Thr Asp Gln Asp Asn Asp Gly Leu Lys Arg Gly Leu Lys Asn
1               5                   10                  15

Arg His Ile Gln Leu Ile Ala Leu Gly Ala Ile Gly Thr Gly Leu
            20                  25                  30

Phe Leu Gly Ile Ala Gln Thr Ile Arg Met Ala Gly Pro Ser Val Leu
        35                  40                  45

Leu Gly Tyr Ala Leu Ala Gly Val Val Ala Phe Phe Ile Met Arg Gln
    50                  55                  60

Leu Gly Glu Met Val Val Asp Glu Pro Val Ala Gly Ser Phe Ser Tyr
65                  70                  75                  80

Phe Ala Ser Lys Tyr Cys Gly His Phe Thr Gly Phe Leu Ser Gly Trp
                85                  90                  95

Asn Tyr Trp Val Leu Tyr Val Leu Val Ser Met Ala Glu Leu Ser Ala
            100                 105                 110

Val Gly Ile Tyr Val Gln Tyr Trp Trp Pro Gly Val Pro Thr Trp Ile
        115                 120                 125

Ser Ala Leu Val Phe Phe Val Val Ile Asn Ala Val Asn Leu Ala Ser
    130                 135                 140

Val Lys Ser Tyr Gly Glu Thr Glu Phe Trp Phe Ser Ile Val Lys Val
145                 150                 155                 160

Ala Ala Ile Ile Gly Met Ile Gly Phe Gly Gly Tyr Leu Leu Leu Ser
                165                 170                 175

Gly His Ala Gly Pro Asp Ala Gly Val Ala Asn Leu Trp Arg His Gly
            180                 185                 190

Gly Phe Phe Pro Asn Gly Ile Gly Gly Leu Ala Met Ala Met Ala Val
        195                 200                 205

Ile Met Phe Ser Phe Gly Gly Leu Glu Leu Val Gly Ile Thr Ala Ala
    210                 215                 220

Glu Ala Asp Asp Pro Ser His Ser Ile Pro Arg Ala Thr Asn Gln Val
225                 230                 235                 240

Ile Tyr Arg Ile Leu Ile Phe Tyr Ile Gly Ala Leu Gly Val Leu Leu
                245                 250                 255

Ser Leu Tyr Pro Trp Gln Lys Val Val Thr Gly Gly Ser Pro Phe Val
            260                 265                 270

Leu Ile Phe His Ala Leu Ser Ser Asp Ile Ala Ala Asn Val Leu Asn
        275                 280                 285

-continued

```
Leu Val Val Leu Thr Ala Ala Leu Ser Val Tyr Asn Ser Cys Val Tyr
    290                 295                 300

Cys Asn Ser Arg Met Leu Tyr Gly Leu Ala Gln Gln Gly Asn Ala Pro
305                 310                 315                 320

Gln Ala Leu Ala Arg Val Asn Arg Arg Gly Ile Pro Ile Ala Ala Leu
                325                 330                 335

Gly Val Ser Ala Phe Ala Thr Ala Leu Cys Val Val Ile Asn Tyr Phe
            340                 345                 350

Met Pro Gly Lys Ala Phe Glu Leu Leu Met Gly Leu Val Val Ser Ala
        355                 360                 365

Ile Ile Ile Asn Trp Ala Met Ile Ser Val Ile His Leu Arg Phe Arg
    370                 375                 380

Gln Ala Lys Arg Ala Ala Gly Glu Thr Thr Arg Phe Arg Ser Leu Gly
385                 390                 395                 400

Tyr Pro Leu Thr Asn Tyr Phe Cys Leu Ala Phe Met Ala Ala Ile Leu
                405                 410                 415

Val Val Met Phe Arg Thr Pro Glu Leu Arg Leu Ser Val Tyr Leu Ile
            420                 425                 430

Pro Val Trp Leu Val Val Leu Ala Leu Gly Tyr Arg Phe Arg Gln Arg
        435                 440                 445

Gly Ala Gly Tyr Ala Leu Gly Gly Gly Val Ser Ala Arg
    450                 455                 460

<210> SEQ ID NO 9
<211> LENGTH: 13
<212> TYPE: PRT
<213> ORGANISM: Artificial Sequence
<220> FEATURE:
<223> OTHER INFORMATION: polypeptide or immunogenic fragment of
      Burkholderia spp genes

<400> SEQUENCE: 9

Ala Gln Thr Ile Arg Met Ala Gly Pro Ser Val Leu Leu
1               5                   10

<210> SEQ ID NO 10
<211> LENGTH: 22
<212> TYPE: PRT
<213> ORGANISM: artificial sequence
<220> FEATURE:
<223> OTHER INFORMATION: polypeptide or immunogenic fragment of
      Burkholderia spp genes

<400> SEQUENCE: 10

Ser Met Ala Glu Leu Ser Ala Val Gly Ile Tyr Val Gln Tyr Trp Trp
1               5                   10                  15

Pro Gly Val Pro Thr Trp
            20

<210> SEQ ID NO 11
<211> LENGTH: 30
<212> TYPE: PRT
<213> ORGANISM: artificial sequence
<220> FEATURE:
<223> OTHER INFORMATION: polypeptide or immunogenic fragment of
      Burkholderia spp genes

<400> SEQUENCE: 11

Leu Leu Leu Ser Gly His Ala Gly Pro Asp Ala Gly Val Ala Asn Leu
1               5                   10                  15
```

Trp Arg His Gly Gly Phe Phe Pro Asn Gly Ile Gly Gly Leu
              20                  25                  30

<210> SEQ ID NO 12
<211> LENGTH: 28
<212> TYPE: PRT
<213> ORGANISM: artificial sequence
<220> FEATURE:
<223> OTHER INFORMATION: polypeptide or immunogenic fragment of
      Burkholderia spp genes

<400> SEQUENCE: 12

Tyr Pro Trp Gln Lys Val Val Thr Gly Gly Ser Pro Phe Val Leu Ile
1               5                   10                  15

Phe His Ala Leu Ser Ser Asp Ile Ala Ala Asn Val
              20                  25

<210> SEQ ID NO 13
<211> LENGTH: 13
<212> TYPE: PRT
<213> ORGANISM: artificial sequence
<220> FEATURE:
<223> OTHER INFORMATION: polypeptide or immunogenic fragment of
      Burkholderia spp genes

<400> SEQUENCE: 13

Ile Asn Tyr Phe Met Pro Gly Lys Ala Phe Glu Leu Leu
1               5                   10

<210> SEQ ID NO 14
<211> LENGTH: 9
<212> TYPE: PRT
<213> ORGANISM: artificial sequence
<220> FEATURE:
<223> OTHER INFORMATION: polypeptide or immunogenic fragment of
      Burkholderia spp genes

<400> SEQUENCE: 14

Met Phe Arg Thr Pro Glu Leu Arg Leu
1               5

<210> SEQ ID NO 15
<211> LENGTH: 520
<212> TYPE: PRT
<213> ORGANISM: Burkholderia pseudomallei

<400> SEQUENCE: 15

Met Ser Pro His Pro Asn Ser Asp Asn Ser Thr Ala Gln Ser Asn Pro
1               5                   10                  15

Pro Gln Leu Arg Arg Ser Leu Lys Ala Arg His Leu Thr Met Ile Ala
              20                  25                  30

Ile Gly Gly Ser Ile Gly Thr Gly Leu Phe Val Ala Ser Gly Ala Ser
            35                  40                  45

Ile Ser Gln Ala Gly Pro Gly Gly Ala Met Leu Ala Tyr Leu Leu Ile
        50                  55                  60

Gly Leu Met Val Tyr Cys Leu Met Met Ser Leu Gly Glu Met Ala Ala
65                  70                  75                  80

Phe Met Pro Val Ser Gly Ser Phe Ala Thr Tyr Gly Ala Lys Tyr Val
                85                  90                  95

Glu Glu Gly Phe Gly Phe Ala Leu Gly Trp Asn Tyr Trp Tyr Asn Trp
              100                 105                 110

Ala Val Thr Ile Ala Val Glu Leu Val Ala Ala Gln Leu Val Met His
          115                 120                 125

Tyr Trp Phe Pro Asp Val Pro Gly Val Trp Ser Ala Ala Phe Leu
130                 135                 140

Gly Val Met Phe Leu Leu Asn Val Leu Thr Val Arg Gly Phe Gly Glu
145                 150                 155                 160

Ala Glu Tyr Trp Phe Ala Leu Ile Lys Val Val Thr Val Ile Ala Phe
                165                 170                 175

Ile Gly Val Gly Leu Leu Met Ile Phe Gly Ile Leu Lys Gly Gly Pro
                180                 185                 190

Ser Asn Gly Trp Ser Asn Phe Thr Ile Gly Asp Ala Pro Phe Ala Gly
                195                 200                 205

Gly Leu Pro Ala Met Met Gly Val Ala Met Ile Ala Gly Phe Ser Phe
210                 215                 220

Gln Gly Thr Glu Leu Ile Gly Val Ala Ala Gly Glu Ser Glu Asn Pro
225                 230                 235                 240

Arg Thr Thr Ile Pro Arg Ala Val Arg Gln Val Phe Trp Arg Ile Leu
                245                 250                 255

Leu Phe Tyr Val Leu Ala Ile Phe Val Ile Gly Val Leu Ile Pro Tyr
                260                 265                 270

Thr Asp Pro Asn Leu Leu Lys Ser Asp Val Thr Asp Val Gly Val Ser
                275                 280                 285

Pro Phe Thr Leu Val Phe Arg His Ala Gly Leu Ala Phe Ala Ala Gly
                290                 295                 300

Val Met Asn Ala Val Ile Leu Thr Ala Val Leu Ser Ala Gly Asn Ser
305                 310                 315                 320

Gly Met Tyr Ala Ser Thr Arg Met Leu His Asn Leu Ala Thr Glu Gly
                325                 330                 335

Arg Ala Pro Lys Leu Phe Ala Lys Leu Ser Ala Gly Gly Val Pro Arg
                340                 345                 350

Asn Ala Leu Tyr Ala Thr Thr Ala Val Gly Leu Cys Phe Leu Ser
                355                 360                 365

Ser Leu Tyr Gly Asp Lys Thr Val Tyr Leu Trp Leu Leu Asn Thr Ser
370                 375                 380

Gly Met Thr Gly Phe Ile Ala Trp Leu Gly Ile Ala Leu Ser His Tyr
385                 390                 395                 400

Arg Phe Arg Lys Gly Tyr Val Arg Gln Gly Phe Ser Val Asp Gln Leu
                405                 410                 415

Pro Tyr Gln Ser Ser Leu Tyr Pro Tyr Gly Pro Ile Phe Ala Phe Ala
                420                 425                 430

Leu Cys Ile Val Ile Ala Leu Gly Gln Asp Tyr Gln Ala Phe Leu Ala
                435                 440                 445

Asn Arg Ile Asp Trp Ile Gly Val Leu Ala Thr Tyr Val Gly Ile Pro
450                 455                 460

Leu Phe Leu Val Val Trp Leu Gly Tyr Arg Leu Val His Lys Thr Arg
465                 470                 475                 480

Val Val Arg Tyr Glu Asp Met Asp Ile Ala Ser Trp Val Ala Glu His
                485                 490                 495

Glu Arg Ala Ala Ala His Glu Ala Arg Glu Ala Ala Val Arg Val
                500                 505                 510

Pro Ser Ser Pro Glu Ala Ala Ser
                515                 520

<210> SEQ ID NO 16
<211> LENGTH: 16

```
<212> TYPE: PRT
<213> ORGANISM: Artificial Sequence
<220> FEATURE:
<223> OTHER INFORMATION: polypeptide or immunogenic fragment of
      Burkholderia spp genes

<400> SEQUENCE: 16

Ala Ser Ile Ser Gln Ala Gly Pro Gly Gly Ala Met Leu Ala Tyr Leu
1               5                   10                  15

<210> SEQ ID NO 17
<211> LENGTH: 17
<212> TYPE: PRT
<213> ORGANISM: Artificial Sequence
<220> FEATURE:
<223> OTHER INFORMATION: polypeptide or immunogenic fragment of
      Burkholderia spp genes

<400> SEQUENCE: 17

Ala Gln Leu Val Met His Tyr Trp Phe Pro Asp Val Pro Gly Val Trp
1               5                   10                  15

Trp

<210> SEQ ID NO 18
<211> LENGTH: 31
<212> TYPE: PRT
<213> ORGANISM: artificial sequence
<220> FEATURE:
<223> OTHER INFORMATION: polypeptide or immunogenic fragment of
      Burkholderia spp genes

<400> SEQUENCE: 18

Ile Phe Gly Ile Leu Lys Gly Gly Pro Ser Asn Gly Trp Ser Asn Phe
1               5                   10                  15

Thr Ile Gly Asp Ala Pro Phe Ala Gly Gly Leu Pro Ala Met Met
            20                  25                  30

<210> SEQ ID NO 19
<211> LENGTH: 31
<212> TYPE: PRT
<213> ORGANISM: artificial sequence
<220> FEATURE:
<223> OTHER INFORMATION: polypeptide or immunogenic fragment of
      Burkholderia spp genes

<400> SEQUENCE: 19

Ile Pro Tyr Thr Asp Pro Asn Leu Leu Lys Ser Asp Val Thr Asp Val
1               5                   10                  15

Gly Val Ser Pro Phe Thr Leu Val Phe Arg His Ala Gly Leu Ala
            20                  25                  30

<210> SEQ ID NO 20
<211> LENGTH: 14
<212> TYPE: PRT
<213> ORGANISM: artificial sequence
<220> FEATURE:
<223> OTHER INFORMATION: polypeptide or immunogenic fragment of
      Burkholderia spp genes

<400> SEQUENCE: 20

Leu Ser Ser Leu Tyr Gly Asp Lys Thr Val Tyr Leu Trp Leu
1               5                   10

<210> SEQ ID NO 21
<211> LENGTH: 17
<212> TYPE: PRT
```

<213> ORGANISM: artificial sequence
<220> FEATURE:
<223> OTHER INFORMATION: polypeptide or immunogenic fragment of
      Burkholderia spp genes

<400> SEQUENCE: 21

Gly Gln Asp Tyr Gln Ala Phe Leu Ala Asn Arg Ile Asp Trp Ile Gly
1               5                   10                  15

Val

<210> SEQ ID NO 22
<211> LENGTH: 487
<212> TYPE: PRT
<213> ORGANISM: Clostridium botulinum A

<400> SEQUENCE: 22

Met Ser Thr Thr Lys Glu Lys Asp Ser Asn Ser His Asn Leu Lys Arg
1               5                   10                  15

Ser Leu Gln Ala Arg His Leu Asn Met Ile Ala Met Gly Gly Ala Ile
            20                  25                  30

Gly Thr Gly Ile Phe Leu Ala Leu Gly Ala Thr Ile Lys Gln Ala Gly
        35                  40                  45

Pro Gly Gly Ala Leu Thr Ala Tyr Ala Cys Ile Gly Val Met Val Tyr
    50                  55                  60

Phe Leu Met Thr Ser Leu Gly Glu Met Ala Thr Phe Met Pro Val Ser
65                  70                  75                  80

Gly Ser Phe Glu Thr Tyr Ala Ser Arg Phe Ile Asp Pro Ala Phe Gly
                85                  90                  95

Phe Ala Leu Gly Trp Asn Tyr Trp Tyr Asn Trp Ala Ile Thr Val Ala
            100                 105                 110

Ala Glu Met Val Ala Gly Ala Leu Ile Met Lys Phe Trp Phe Pro Asn
        115                 120                 125

Val Pro Ala Ile Ile Trp Ser Val Leu Phe Leu Val Leu Ile Val Ser
    130                 135                 140

Leu Asn Leu Leu Ser Thr Lys Ala Tyr Gly Glu Ser Glu Tyr Trp Phe
145                 150                 155                 160

Ala Gly Ile Lys Val Phe Thr Val Ile Val Phe Leu Leu Ile Gly Ile
                165                 170                 175

Ala Thr Ile Leu Gly Ile Leu Gly Gly His Thr Val Gly Leu Gln Asn
            180                 185                 190

Phe Thr Ile Lys Asp Ala Pro Phe Val Gly Gly Val Lys Ser Ile Phe
        195                 200                 205

Met Val Phe Leu Ile Ala Gly Phe Ser Phe Gln Gly Thr Glu Leu Val
    210                 215                 220

Gly Ile Ala Ala Gly Glu Ser Glu Asn Pro Lys Lys Thr Ile Pro Lys
225                 230                 235                 240

Ala Ile Asn Thr Ile Phe Trp Arg Ile Ile Val Phe Tyr Leu Gly Thr
                245                 250                 255

Ile Phe Val Val Ser Ala Ile Ile Pro Tyr Thr Asp Ala Gly Val Asn
            260                 265                 270

Thr Ser Pro Phe Thr Leu Val Phe Glu Arg Ala Gly Ile Ala Ala Asp
        275                 280                 285

Ala Ser Leu Met Asn Ala Val Ile Leu Thr Ser Val Ile Ser Cys Gly
    290                 295                 300

Asn Ser Gly Met Tyr Ala Ser Ser Arg Met Leu Tyr Ala Met Ala Lys
305                 310                 315                 320

```
Glu Gly Lys Ala Pro Ser Trp Leu Gly Lys Leu Asn Ser Arg Gly Val
                325                 330                 335

Pro Val Asn Ala Leu Ala Leu Thr Thr Leu Val Ala Ser Ala Cys Phe
            340                 345                 350

Leu Thr Gly Leu Tyr Ala Glu Thr Thr Val Tyr Val Trp Leu Val Ala
        355                 360                 365

Ala Ser Gly Leu Ala Gly Phe Ile Ala Trp Val Gly Ile Ala Leu Cys
    370                 375                 380

His Tyr Arg Phe Arg Lys Ala Tyr Val Ala Gln Gly Arg Asp Leu Asn
385                 390                 395                 400

Lys Leu Val Tyr Lys Ala Lys Leu Phe Pro Leu Gly Pro Ile Ile Ala
                405                 410                 415

Leu Val Leu Cys Ile Ile Val Ile Leu Gly Gln Gly Ile Ser Tyr Phe
            420                 425                 430

Glu Ala Thr Lys Ile Asp Trp Asn Gly Ile Ile Ala Ser Tyr Ile Gly
        435                 440                 445

Leu Pro Ile Phe Phe Gly Leu Trp Phe Ser Tyr Lys Lys His Lys
    450                 455                 460

Thr Lys Val Val Asn Leu Gln Glu Ile Ser Phe Asp Val Glu Asp Thr
465                 470                 475                 480

His Leu Lys Thr Glu Ile Val
                485

<210> SEQ ID NO 23
<211> LENGTH: 16
<212> TYPE: PRT
<213> ORGANISM: artificial sequence
<220> FEATURE:
<223> OTHER INFORMATION: polypeptide or immunogenic fragment of
      Clostridium spp genes

<400> SEQUENCE: 23

Gly Ala Thr Ile Lys Gln Ala Gly Pro Gly Ala Leu Thr Ala Tyr
1               5                   10                  15

<210> SEQ ID NO 24
<211> LENGTH: 18
<212> TYPE: PRT
<213> ORGANISM: artificial sequence
<220> FEATURE:
<223> OTHER INFORMATION: polypeptide or immunogenic fragment of
      Clostridium spp genes

<400> SEQUENCE: 24

Met Val Ala Gly Ala Leu Ile Met Lys Phe Trp Phe Pro Asn Val Pro
1               5                   10                  15

Ala Ile

<210> SEQ ID NO 25
<211> LENGTH: 30
<212> TYPE: PRT
<213> ORGANISM: artificial sequence
<220> FEATURE:
<223> OTHER INFORMATION: polypeptide or immunogenic fragment of
      Clostridium spp genes

<400> SEQUENCE: 25

Leu Gly Ile Leu Gly Gly His Thr Val Gly Leu Gln Asn Phe Thr Ile
1               5                   10                  15

Lys Asp Ala Pro Phe Val Gly Gly Val Lys Ser Ile Phe Met
```

<210> SEQ ID NO 26
<211> LENGTH: 29
<212> TYPE: PRT
<213> ORGANISM: artificial sequence
<220> FEATURE:
<223> OTHER INFORMATION: polypeptide or immunogenic fragment of
      Clostridium spp genes

<400> SEQUENCE: 26

Ala Ile Ile Pro Tyr Thr Asp Ala Gly Val Asn Thr Ser Pro Phe Thr
1               5                   10                  15

Leu Val Phe Glu Arg Ala Gly Ile Ala Ala Asp Ala Ser
            20                  25

<210> SEQ ID NO 27
<211> LENGTH: 13
<212> TYPE: PRT
<213> ORGANISM: artificial sequence
<220> FEATURE:
<223> OTHER INFORMATION: polypeptide or immunogenic fragment of
      Clostridium spp genes

<400> SEQUENCE: 27

Gly Leu Tyr Ala Glu Thr Thr Val Tyr Val Trp Leu Val
1               5                   10

<210> SEQ ID NO 28
<211> LENGTH: 15
<212> TYPE: PRT
<213> ORGANISM: artificial sequence
<220> FEATURE:
<223> OTHER INFORMATION: polypeptide or immunogenic fragment of
      Clostridium spp genes

<400> SEQUENCE: 28

Gly Gln Gly Ile Ser Tyr Phe Glu Ala Thr Lys Ile Asp Trp Asn
1               5                   10                  15

<210> SEQ ID NO 29
<211> LENGTH: 447
<212> TYPE: PRT
<213> ORGANISM: Clostridium difficile

<400> SEQUENCE: 29

Met Arg Arg Lys Lys Met Glu Ser Asn Glu Leu Lys Lys Thr Leu Gly
1               5                   10                  15

Val Ser Ala Ala Leu Ser Thr Val Val Gly Ser Val Ile Gly Ala Gly
            20                  25                  30

Val Phe Phe Lys Pro Gln Ala Val Tyr Thr Leu Thr Gly Gly Ala Pro
        35                  40                  45

Gly Leu Gly Ile Leu Ala Trp Leu Ile Ala Gly Ile Ile Thr Ile Thr
    50                  55                  60

Ala Gly Leu Thr Ala Ala Glu Val Ser Val Ala Ile Pro Lys Thr Gly
65                  70                  75                  80

Gly Met Met Val Tyr Ile Lys Glu Ile Tyr Gly Glu Lys Leu Gly Phe
                85                  90                  95

Leu Thr Gly Trp Met Gln Ile Val Leu Phe Tyr Pro Gly Met Met Ala
            100                 105                 110

Ala Leu Gly Val Ile Phe Gly Glu Gln Ala Ser Ala Leu Ile Gly Ser
        115                 120                 125

```
Pro Ser Leu Leu Pro Ile Ala Ile Gly Ile Ile Val Ile Val Ala
    130                 135                 140
Gly Leu Asn Met Leu Gly Ser Lys Thr Gly Gly Val Ile Gln Thr Val
145                 150                 155                 160
Ser Thr Ile Cys Lys Leu Ile Pro Leu Ile Leu Ile Met Ile Val Gly
                165                 170                 175
Phe Ile Lys Gly Gly Gly Asn Asn Pro Ile Leu Thr Pro Met Val Gly
            180                 185                 190
Glu Gly Leu Ser Leu Gly Ser Val Leu Gly Gln Val Leu Ile Ala Ile
        195                 200                 205
Leu Phe Ala Phe Asp Gly Trp Met Asn Val Gly Thr Leu Ala Gly Glu
210                 215                 220
Met Lys Asn Pro Gly Lys Asp Leu Pro Lys Ala Ile Ile Gly Gly Leu
225                 230                 235                 240
Ser Val Val Met Ala Val Tyr Phe Ile Ile Asn Leu Ala Tyr Leu Trp
                245                 250                 255
Val Leu Pro Ala Ser Glu Leu Ala Asn Tyr Ala Ser Pro Ala Ser Ala
            260                 265                 270
Val Ala Glu Val Ile Phe Gly Ser Met Gly Gly Lys Ile Ile Ser Val
        275                 280                 285
Gly Ile Leu Ile Ser Val Phe Gly Ala Leu Asn Gly Phe Leu Leu Thr
290                 295                 300
Gly Ser Arg Val Ala Tyr Thr Leu Ala Thr Asp Lys Thr Leu Pro Lys
305                 310                 315                 320
Tyr Ser Ile Phe Ser Lys Leu Asn Ser Ala Gln Val Pro Ala Asn Ala
                325                 330                 335
Ile Ala Leu Val Ser Val Ile Ala Ser Ile Tyr Ala Leu Ser Gly Gln
            340                 345                 350
Phe Asn Leu Leu Thr Asp Leu Ala Val Phe Ala Thr Trp Ile Phe Tyr
        355                 360                 365
Val Leu Thr Phe Ile Gly Val Met Lys Leu Arg Lys Thr His Pro Asn
370                 375                 380
Ile Pro Arg Glu Tyr Lys Val Pro Leu Tyr Pro Ile Val Pro Ile Ile
385                 390                 395                 400
Ala Ile Ala Ser Gly Ile Phe Val Val Asn Gln Leu Cys Phe Ala
                405                 410                 415
Gly Met Lys Thr Thr Met Ile Ser Ile Gly Leu Val Ile Thr Ala
            420                 425                 430
Ile Gly Leu Pro Val Tyr Ala Tyr Met Thr Arg Gly Ile Lys Arg
        435                 440                 445
```

<210> SEQ ID NO 30
<211> LENGTH: 23
<212> TYPE: PRT
<213> ORGANISM: artificial sequence
<220> FEATURE:
<223> OTHER INFORMATION: polypeptide or immunogenic fragment of
    Clostridium spp genes

<400> SEQUENCE: 30

```
Val Phe Phe Lys Pro Gln Ala Val Tyr Thr Leu Thr Gly Gly Ala Pro
1               5                   10                  15

Gly Leu Gly Ile Leu Ala Trp
            20
```

<210> SEQ ID NO 31

```
<211> LENGTH: 18
<212> TYPE: PRT
<213> ORGANISM: artificial sequence
<220> FEATURE:
<223> OTHER INFORMATION: polypeptide or immunogenic fragment of
      Clostridium spp genes

<400> SEQUENCE: 31

Leu Gly Val Ile Phe Gly Glu Gln Ala Ser Ala Leu Ile Gly Ser Pro
1               5                   10                  15

Ser Leu

<210> SEQ ID NO 32
<211> LENGTH: 24
<212> TYPE: PRT
<213> ORGANISM: artificial sequence
<220> FEATURE:
<223> OTHER INFORMATION: polypeptide or immunogenic fragment of
      Clostridium spp genes

<400> SEQUENCE: 32

Gly Phe Ile Lys Gly Gly Gly Asn Asn Pro Ile Leu Thr Pro Met Val
1               5                   10                  15

Gly Glu Gly Leu Ser Leu Gly Ser
            20

<210> SEQ ID NO 33
<211> LENGTH: 36
<212> TYPE: PRT
<213> ORGANISM: artificial sequence
<220> FEATURE:
<223> OTHER INFORMATION: polypeptide or immunogenic fragment of
      Clostridium spp genes

<400> SEQUENCE: 33

Leu Trp Val Leu Pro Ala Ser Glu Leu Ala Asn Tyr Ala Ser Pro Ala
1               5                   10                  15

Ser Ala Val Ala Glu Val Ile Phe Gly Ser Met Gly Gly Lys Ile Ile
            20                  25                  30

Ser Val Gly Ile
        35

<210> SEQ ID NO 34
<211> LENGTH: 11
<212> TYPE: PRT
<213> ORGANISM: artificial sequence
<220> FEATURE:
<223> OTHER INFORMATION: polypeptide or immunogenic fragment of
      Clostridium spp genes

<400> SEQUENCE: 34

Ala Leu Ser Gly Gln Phe Asn Leu Leu Thr Asp
1               5                   10

<210> SEQ ID NO 35
<211> LENGTH: 12
<212> TYPE: PRT
<213> ORGANISM: artificial sequence
<220> FEATURE:
<223> OTHER INFORMATION: polypeptide or immunogenic fragment of
      Clostridium spp genes

<400> SEQUENCE: 35

Asn Gln Leu Cys Phe Ala Gly Met Lys Thr Thr Met
1               5                   10
```

<210> SEQ ID NO 36
<211> LENGTH: 450
<212> TYPE: PRT
<213> ORGANISM: Enterococcus faecalis

<400> SEQUENCE: 36

```
Met Ser Glu Thr Gln Gln Thr Thr Leu Lys Lys Gln Leu Ser Ser Arg
1               5                   10                  15

His Ile Thr Met Leu Ala Leu Gly Gly Ala Ile Gly Ala Gly Leu Phe
            20                  25                  30

Lys Gly Ser Gly Glu Ala Ile Gly Ile Ala Gly Pro Ser Val Leu Ile
        35                  40                  45

Ala Phe Leu Ile Gly Gly Ala Val Leu Phe Ile Val Met Ser Gly Leu
    50                  55                  60

Gly Lys Leu Val Leu Asp Gly Gly Asp Thr His His Gly Leu Ser Gly
65                  70                  75                  80

Leu Val Arg Pro Phe Leu Gly Ala His Ser Ala Asp Phe Ile Asp Trp
                85                  90                  95

Val Tyr Tyr Ser Met Trp Thr Ile Asn Ile Ile Ala Glu Ala Val Ala
            100                 105                 110

Ala Ala Ser Phe Leu Gln Leu Trp Phe Pro Asn Ile Pro Ala Trp Phe
        115                 120                 125

Phe Val Phe Ile Leu Ala Ile Leu Thr Thr Leu Ile Asn Leu Tyr Ser
    130                 135                 140

Val Arg Leu Phe Ala Glu Thr Glu Tyr Trp Leu Ala Phe Ala Lys Ile
145                 150                 155                 160

Ser Val Ile Ile Leu Leu Ile Ile Phe Gly Val Tyr Leu Val Gly Gln
                165                 170                 175

Gln Met Leu Gly Ser Gly Val Phe Pro Thr Leu Gln Ser Ile Thr Lys
            180                 185                 190

His Gly Gly Phe Ala Pro His Gly Met Lys Gly Ile Val Asn Ser Leu
        195                 200                 205

Leu Val Val Ile Tyr Ser Tyr Gly Gly Ser Glu Leu Ile Ala Ile Thr
    210                 215                 220

Val Ser Glu Ala Asp Asp Pro Lys Lys Ala Ile Pro Lys Ala Ile Arg
225                 230                 235                 240

Gly Val Met Gly Arg Ile Ile Ser Phe Tyr Ile Ile Pro Leu Phe Leu
                245                 250                 255

Leu Leu Ile Ile Phe Pro Trp Asn Thr Leu Ala Ser Thr Thr Val Ser
            260                 265                 270

Pro Phe Val Met Val Phe Glu Lys Met Asn Ile Pro Phe Ala Ala Asp
        275                 280                 285

Ile Val Asn Phe Val Ile Ile Leu Ala Leu Phe Ser Ser Ile Asn Ser
    290                 295                 300

Gly Val Tyr Ala Ser Ser Arg Leu Leu Tyr Phe Arg Leu Lys Asp Lys
305                 310                 315                 320

Lys Gly Pro Met Ser Lys Leu Ala Val Leu Asn Lys His Gln Val Pro
                325                 330                 335

Gln Arg Ser Val Phe Cys Ala Ser Val Leu Tyr Leu Gly Val Ile
            340                 345                 350

Leu Ser Tyr Phe Val Gly Asp Glu Leu Phe Gly Tyr Leu Ala Gly Ser
        355                 360                 365

Leu Ser Tyr Thr Val Leu Leu Ile Trp Ile Leu Ile Ser Ala Ala Ala
    370                 375                 380
```

```
Phe Val Leu Ser Leu Lys Arg Gly Ser Leu Phe Glu Lys Ser Ile Asn
385                 390                 395                 400

Leu Leu Ala Leu Ile Ile Leu Gly Leu Ile Phe Ile Gly Ile Leu Phe
            405                 410                 415

Thr Asn Ser Leu Gly Val Thr Leu Leu Thr Gly Leu Leu Tyr Phe Val
                420                 425                 430

Ile Phe Phe Ser Tyr Arg Lys Lys Asn Asp Ser Phe Leu Leu Ser Asp
        435                 440                 445

Glu Ser
    450

<210> SEQ ID NO 37
<211> LENGTH: 18
<212> TYPE: PRT
<213> ORGANISM: artificial sequence
<220> FEATURE:
<223> OTHER INFORMATION: polypeptide or immunogenic fragment of
      Enterococcus spp genes

<400> SEQUENCE: 37

Phe Lys Gly Ser Gly Glu Ala Ile Gly Ile Ala Gly Pro Ser Val Leu
1               5                   10                  15

Ile Ala

<210> SEQ ID NO 38
<211> LENGTH: 15
<212> TYPE: PRT
<213> ORGANISM: artificial sequence
<220> FEATURE:
<223> OTHER INFORMATION: polypeptide or immunogenic fragment of
      Enetrococcus spp genes

<400> SEQUENCE: 38

Ala Ser Phe Leu Gln Leu Trp Phe Pro Asn Ile Pro Ala Trp Phe
1               5                   10                  15

<210> SEQ ID NO 39
<211> LENGTH: 37
<212> TYPE: PRT
<213> ORGANISM: artificial sequence
<220> FEATURE:
<223> OTHER INFORMATION: polypeptide or immunogenic fragment of
      Enetrococcus spp genes

<400> SEQUENCE: 39

Tyr Leu Val Gly Gln Gln Met Leu Gly Ser Gly Val Pro Thr Leu
1               5                   10                  15

Gln Ser Ile Thr Lys His Gly Gly Phe Ala Pro His Gly Met Lys Gly
            20                  25                  30

Ile Val Asn Ser Leu
        35

<210> SEQ ID NO 40
<211> LENGTH: 32
<212> TYPE: PRT
<213> ORGANISM: artificial sequence
<220> FEATURE:
<223> OTHER INFORMATION: polypeptide or immunogenic fragment of
      Enetrococcus spp genes

<400> SEQUENCE: 40

Pro Trp Asn Thr Leu Ala Ser Thr Thr Val Ser Pro Phe Val Met Val
1               5                   10                  15
```

```
Phe Glu Lys Met Asn Ile Pro Phe Ala Ala Asp Ile Val Asn Phe Val
            20                  25                  30
```

<210> SEQ ID NO 41
<211> LENGTH: 15
<212> TYPE: PRT
<213> ORGANISM: artificial sequence
<220> FEATURE:
<223> OTHER INFORMATION: polypeptide or immunogenic fragment of
      Enetrococcus spp genes

<400> SEQUENCE: 41

```
Phe Val Gly Asp Glu Leu Phe Gly Tyr Leu Ala Gly Ser Leu Ser
1               5                   10                  15
```

<210> SEQ ID NO 42
<211> LENGTH: 34
<212> TYPE: PRT
<213> ORGANISM: artificial sequence
<220> FEATURE:
<223> OTHER INFORMATION: polypeptide or immunogenic fragment of
      Enetrococcus spp genes

<400> SEQUENCE: 42

```
Thr Asn Ser Leu Gly Val Thr Leu Leu Thr Gly Leu Leu Tyr Phe Val
1               5                   10                  15

Ile Phe Phe Ser Tyr Arg Lys Asn Asp Ser Phe Leu Leu Ser Asp
            20                  25                  30

Glu Ser
```

<210> SEQ ID NO 43
<211> LENGTH: 489
<212> TYPE: PRT
<213> ORGANISM: Escherichia coli

<400> SEQUENCE: 43

```
Met Val Ser Glu Thr Lys Thr Thr Glu Ala Pro Gly Leu Arg Arg Glu
1               5                   10                  15

Leu Lys Ala Arg His Leu Thr Met Ile Ala Ile Gly Gly Ser Ile Gly
            20                  25                  30

Thr Gly Leu Phe Val Ala Ser Gly Ala Thr Ile Ser Gln Ala Gly Pro
        35                  40                  45

Gly Gly Ala Leu Leu Ser Tyr Met Leu Ile Gly Leu Met Val Tyr Phe
    50                  55                  60

Leu Met Thr Ser Leu Gly Glu Leu Ala Ala Tyr Met Pro Val Ser Gly
65                  70                  75                  80

Ser Phe Ala Thr Tyr Gly Gln Asn Tyr Val Glu Glu Gly Phe Gly Phe
                85                  90                  95

Ala Leu Gly Trp Asn Tyr Trp Tyr Asn Trp Ala Val Thr Ile Ala Val
            100                 105                 110

Asp Leu Val Ala Ala Gln Leu Val Met Ser Trp Trp Phe Pro Asp Thr
        115                 120                 125

Pro Gly Trp Ile Trp Ser Ala Leu Phe Leu Gly Val Ile Phe Leu Leu
    130                 135                 140

Asn Tyr Ile Ser Val Arg Gly Phe Gly Glu Ala Glu Tyr Trp Phe Ser
145                 150                 155                 160

Leu Ile Lys Val Thr Thr Val Ile Val Phe Ile Ile Val Gly Val Leu
                165                 170                 175

Met Ile Ile Gly Ile Phe Lys Gly Ala Gln Pro Ala Gly Trp Ser Asn
```

```
                    180                 185                 190
Trp Thr Ile Gly Glu Ala Pro Phe Ala Gly Gly Phe Ala Ala Met Ile
                195                 200                 205
Gly Val Ala Met Ile Val Gly Phe Ser Phe Gln Gly Thr Glu Leu Ile
            210                 215                 220
Gly Ile Ala Ala Gly Glu Ser Glu Asp Pro Ala Lys Asn Ile Pro Arg
225                 230                 235                 240
Ala Val Arg Gln Val Phe Trp Arg Ile Leu Leu Phe Tyr Val Phe Ala
                245                 250                 255
Ile Leu Ile Ile Ser Leu Ile Ile Pro Tyr Thr Asp Pro Ser Leu Leu
            260                 265                 270
Arg Asn Asp Val Lys Asp Ile Ser Val Ser Pro Phe Thr Leu Val Phe
        275                 280                 285
Gln His Ala Gly Leu Leu Ser Ala Ala Ala Val Met Asn Ala Val Ile
        290                 295                 300
Leu Thr Ala Val Leu Ser Ala Gly Asn Ser Gly Met Tyr Ala Ser Thr
305                 310                 315                 320
Arg Met Leu Tyr Thr Leu Ala Cys Asp Gly Lys Ala Pro Arg Ile Phe
                325                 330                 335
Ala Lys Leu Ser Arg Gly Gly Val Pro Arg Asn Ala Leu Tyr Ala Thr
                340                 345                 350
Thr Val Ile Ala Gly Leu Cys Phe Leu Thr Ser Met Phe Gly Asn Gln
            355                 360                 365
Thr Val Tyr Leu Trp Leu Leu Asn Thr Ser Gly Met Thr Gly Phe Ile
        370                 375                 380
Ala Trp Leu Gly Ile Ala Ile Ser His Tyr Arg Phe Arg Arg Gly Tyr
385                 390                 395                 400
Val Leu Gln Gly His Asp Ile Asn Asp Leu Pro Tyr Arg Ser Gly Phe
                405                 410                 415
Phe Pro Leu Gly Pro Ile Phe Ala Phe Ile Leu Cys Leu Ile Ile Thr
                420                 425                 430
Leu Gly Gln Asn Tyr Glu Ala Phe Leu Lys Asp Thr Ile Asp Trp Gly
            435                 440                 445
Gly Val Ala Ala Thr Tyr Ile Gly Ile Pro Leu Phe Leu Ile Ile Trp
        450                 455                 460
Phe Gly Tyr Lys Leu Ile Lys Gly Thr His Phe Val Arg Tyr Ser Glu
465                 470                 475                 480
Met Lys Phe Pro Gln Asn Asp Lys Lys
                485

<210> SEQ ID NO 44
<211> LENGTH: 19
<212> TYPE: PRT
<213> ORGANISM: artificial sequence
<220> FEATURE:
<223> OTHER INFORMATION: polypeptide or immunogenic fragment of
      Escherichia spp genes

<400> SEQUENCE: 44

Gly Ala Thr Ile Ser Gln Ala Gly Pro Gly Gly Ala Leu Leu Ser Tyr
1               5                   10                  15

Met Leu Ile

<210> SEQ ID NO 45
<211> LENGTH: 17
<212> TYPE: PRT
```

```
<213> ORGANISM: artificial sequence
<220> FEATURE:
<223> OTHER INFORMATION: polypeptide or immunogenic fragment of
      Escherichia spp genes

<400> SEQUENCE: 45

Ala Ala Gln Leu Val Met Ser Trp Trp Phe Pro Asp Thr Pro Gly Trp
1               5                   10                  15

Ile

<210> SEQ ID NO 46
<211> LENGTH: 27
<212> TYPE: PRT
<213> ORGANISM: artificial sequence
<220> FEATURE:
<223> OTHER INFORMATION: polypeptide or immunogenic fragment of
      Escherichia spp genes

<400> SEQUENCE: 46

Met Ile Ile Gly Ile Phe Lys Gly Ala Gln Pro Ala Gly Trp Ser Asn
1               5                   10                  15

Trp Thr Ile Gly Glu Ala Pro Phe Ala Gly Gly
            20                  25

<210> SEQ ID NO 47
<211> LENGTH: 30
<212> TYPE: PRT
<213> ORGANISM: artificial sequence
<220> FEATURE:
<223> OTHER INFORMATION: polypeptide or immunogenic fragment of
      Escherichia spp genes

<400> SEQUENCE: 47

Ile Ile Pro Tyr Thr Asp Pro Ser Leu Leu Arg Asn Asp Val Lys Asp
1               5                   10                  15

Ile Ser Val Ser Pro Phe Thr Leu Val Phe Gln His Ala Gly
            20                  25                  30

<210> SEQ ID NO 48
<211> LENGTH: 13
<212> TYPE: PRT
<213> ORGANISM: artificial sequence
<220> FEATURE:
<223> OTHER INFORMATION: polypeptide or immunogenic fragment of
      Escherichia spp genes

<400> SEQUENCE: 48

Thr Ser Met Phe Gly Asn Gln Thr Val Tyr Leu Trp Leu
1               5                   10

<210> SEQ ID NO 49
<211> LENGTH: 21
<212> TYPE: PRT
<213> ORGANISM: artificial sequence
<220> FEATURE:
<223> OTHER INFORMATION: polypeptide or immunogenic fragment of
      Escherichia spp genes

<400> SEQUENCE: 49

Thr Leu Gly Gln Asn Tyr Glu Ala Phe Leu Lys Asp Thr Ile Asp Trp
1               5                   10                  15

Gly Gly Val Ala Ala
            20

<210> SEQ ID NO 50
```

```
<211> LENGTH: 455
<212> TYPE: PRT
<213> ORGANISM: Haemophilus influenza

<400> SEQUENCE: 50
```

| | | | | | | | | | | | | | | |
|---|---|---|---|---|---|---|---|---|---|---|---|---|---|---|
| Met | Ser | Asp | Lys | Glu | Val | Lys | Lys | Ser | Leu | Thr | Leu | Arg | His | Ile | Gln |
| 1 | | | | 5 | | | | | 10 | | | | | 15 | |
| Phe | Leu | Ala | Leu | Gly | Ser | Ala | Ile | Gly | Thr | Gly | Leu | Phe | Tyr | Gly | Ser |
| | | | 20 | | | | | 25 | | | | | 30 | | |
| Tyr | Glu | Ser | Ile | Lys | Leu | Ala | Gly | Ser | Ser | Val | Ile | Phe | Gly | Tyr | Leu |
| | | 35 | | | | | 40 | | | | | 45 | | | |
| Ile | Ile | Gly | Phe | Ile | Ile | Tyr | Ile | Ile | Met | Lys | Ser | Leu | Gly | Asp | Leu |
| 50 | | | | | 55 | | | | | 60 | | | | | |
| Ile | Leu | Asn | Thr | Pro | Thr | Gly | Lys | Thr | Phe | Gly | Asp | Tyr | Ala | Ser | Ile |
| 65 | | | | 70 | | | | | 75 | | | | | 80 | |
| Tyr | Leu | Gly | Lys | Lys | Trp | Gly | Phe | Val | Thr | Gly | Trp | Ala | Tyr | Ala | Leu |
| | | | | 85 | | | | | 90 | | | | | 95 | |
| Glu | Met | Ile | Ile | Val | Cys | Ile | Ala | Asp | Leu | Thr | Ala | Phe | Gly | Ile | Tyr |
| | | | 100 | | | | | 105 | | | | | 110 | | |
| Met | Lys | Phe | Trp | Tyr | Pro | Glu | Val | Asp | Ser | Trp | Ile | Trp | Ile | Thr | Ile |
| | | 115 | | | | | 120 | | | | | 125 | | | |
| Leu | Ile | Phe | Phe | Ile | Ala | Ser | Ile | Asn | Leu | Ile | Asn | Val | Arg | Val | Phe |
| 130 | | | | | 135 | | | | | 140 | | | | | |
| Gly | Glu | Leu | Glu | Phe | Ile | Leu | Thr | Ile | Ile | Lys | Val | Ile | Ala | Ile | Gly |
| 145 | | | | | 150 | | | | | 155 | | | | | 160 |
| Phe | Met | Ile | Val | Ile | Gly | Val | Ile | Leu | Leu | Phe | Tyr | Thr | Gln | Leu | Asn |
| | | | | 165 | | | | | 170 | | | | | 175 | |
| Lys | Asp | Ser | Leu | Glu | Gln | Ile | Ala | Ser | Ile | Asn | Asn | Leu | Ile | Lys | Tyr |
| | | | 180 | | | | | 185 | | | | | 190 | | |
| Gly | Gly | Phe | Phe | Pro | Asn | Gly | Leu | Glu | Gly | Phe | Ile | Tyr | Ser | Leu | Ser |
| | | | 195 | | | | | 200 | | | | | 205 | | |
| Ile | Ile | Ala | Phe | Ser | Phe | Gly | Gly | Ile | Glu | Ile | Ile | Gly | Ile | Ser | Ala |
| | | 210 | | | | | 215 | | | | | 220 | | | |
| Gly | Glu | Thr | Leu | Asp | Pro | Lys | Lys | Ser | Ile | Pro | Ile | Ala | Ile | Arg | Ser |
| 225 | | | | | 230 | | | | | 235 | | | | | 240 |
| Val | Pro | Phe | Arg | Ile | Ile | Phe | Phe | Tyr | Ile | Phe | Thr | Ile | Phe | Ile | Ile |
| | | | | 245 | | | | | 250 | | | | | 255 | |
| Leu | Thr | Ile | Val | Pro | Trp | Asn | Asn | Leu | Asp | Gly | Ser | Lys | Ser | Pro | Phe |
| | | | | 260 | | | | | 265 | | | | | 270 | |
| Val | Ile | Ile | Phe | Glu | Tyr | Ile | Gly | Ile | Pro | Tyr | Ser | Ser | Asp | Ile | Leu |
| | | | 275 | | | | | 280 | | | | | 285 | | |
| Asn | Ile | Val | Ile | Ile | Ser | Ala | Ser | Ile | Ser | Ala | Ile | Asn | Ser | Asp | Ile |
| | 290 | | | | | 295 | | | | | 300 | | | | |
| Phe | Ser | Ala | Ser | Arg | Ile | Ile | Tyr | Ser | Met | Ser | Lys | Arg | Asn | Gln | Ala |
| 305 | | | | | 310 | | | | | 315 | | | | | 320 |
| Pro | Ile | Ile | Leu | Ser | Arg | Ile | Ser | Lys | Gln | Gly | Ile | Pro | Trp | Val | Val |
| | | | | 325 | | | | | 330 | | | | | 335 | |
| Val | Leu | Leu | Val | Ser | Phe | Leu | Leu | Cys | Phe | Gly | Ile | Phe | Leu | Asn | Tyr |
| | | | | 340 | | | | | 345 | | | | | 350 | |
| Leu | Phe | Pro | Asp | Lys | Ile | Phe | Phe | Ile | Ala | Ser | Ala | Ser | Val |
| | | | 355 | | | | | 360 | | | | | 365 | |
| Ile | Thr | Ile | Phe | Val | Trp | Ile | Ile | Ile | Leu | Phe | Ser | Asn | Met | Phe | Met |
| | | 370 | | | | | 375 | | | | | 380 | | | |
| Asn | Asn | Asn | Arg | Leu | Ser | Ser | Phe | Ile | Gly | Phe | Leu | Gln | Lys | Asn | Lys |

```
                385                 390                 395                 400
        Phe Ile Leu Phe Ser Ile Phe Ser Leu Val Phe Ile Val Leu Phe Met
                        405                 410                 415

Leu Leu Asn Lys Glu Thr Arg Trp Ala Ser Leu Val Gly Val Ser Ile
                        420                 425                 430

Ile Leu Leu Ile Phe Ile Ile Gly Thr Lys Phe Asn Asn Ile Ile Phe
                        435                 440                 445

Lys Glu Asn Lys Asp Glu Cys
                        450                 455

<210> SEQ ID NO 51
<211> LENGTH: 19
<212> TYPE: PRT
<213> ORGANISM: artificial sequence
<220> FEATURE:
<223> OTHER INFORMATION: polypeptide or immunogenic fragment of
      Haemophilus spp genes

<400> SEQUENCE: 51

Phe Tyr Gly Ser Tyr Glu Ser Ile Lys Leu Ala Gly Ser Ser Val Ile
1               5                   10                  15

Phe Gly Tyr

<210> SEQ ID NO 52
<211> LENGTH: 20
<212> TYPE: PRT
<213> ORGANISM: artificial sequence
<220> FEATURE:
<223> OTHER INFORMATION: polypeptide or immunogenic fragment of
      Haemophilus spp genes

<400> SEQUENCE: 52

Leu Thr Ala Phe Gly Ile Tyr Met Lys Phe Trp Tyr Pro Glu Val Asp
1               5                   10                  15

Ser Trp Ile Trp
            20

<210> SEQ ID NO 53
<211> LENGTH: 36
<212> TYPE: PRT
<213> ORGANISM: artificial sequence
<220> FEATURE:
<223> OTHER INFORMATION: polypeptide or immunogenic fragment of
      Haemophilus spp genes

<400> SEQUENCE: 53

Leu Leu Phe Tyr Thr Gln Leu Asn Lys Asp Ser Leu Glu Gln Ile Ala
1               5                   10                  15

Ser Ile Asn Asn Leu Ile Lys Tyr Gly Gly Phe Phe Pro Asn Gly Leu
                20                  25                  30

Glu Gly Phe Ile
        35

<210> SEQ ID NO 54
<211> LENGTH: 32
<212> TYPE: PRT
<213> ORGANISM: artificial sequence
<220> FEATURE:
<223> OTHER INFORMATION: polypeptide or immunogenic fragment of
      Haemophilus spp genes

<400> SEQUENCE: 54

Val Pro Trp Asn Asn Leu Asp Gly Ser Lys Ser Pro Phe Val Ile Ile
```

```
                1               5                  10                 15
Phe Glu Tyr Ile Gly Ile Pro Tyr Ser Ser Asp Ile Leu Asn Ile Val
                20                 25                 30

<210> SEQ ID NO 55
<211> LENGTH: 9
<212> TYPE: PRT
<213> ORGANISM: artificial sequence
<220> FEATURE:
<223> OTHER INFORMATION: polypeptide or immunogenic fragment of
      Haemophilus spp genes

<400> SEQUENCE: 55

Asn Tyr Leu Phe Pro Asp Lys Ile Phe
1               5

<210> SEQ ID NO 56
<211> LENGTH: 10
<212> TYPE: PRT
<213> ORGANISM: artificial sequence
<220> FEATURE:
<223> OTHER INFORMATION: polypeptide or immunogenic fragment of
      Haemophilus spp genes

<400> SEQUENCE: 56

Leu Asn Lys Glu Thr Arg Trp Ala Ser Leu
1               5                  10

<210> SEQ ID NO 57
<211> LENGTH: 475
<212> TYPE: PRT
<213> ORGANISM: Helicobacter pylori

<400> SEQUENCE: 57

Met Lys Asp Asn Thr Thr Leu Ser Arg Asp Ile Ser Phe Asn Gln Leu
1               5                  10                 15

Met Met Ile Ala Leu Gly Gly Thr Ile Gly Thr Gly Leu Phe Val Gly
                20                 25                 30

Thr Gly Gly Asn Ile Ala Ser Ala Gly Pro Leu Ala Thr Leu Leu Ala
            35                 40                 45

Tyr Leu Ile Gly Gly Ile Ile Val Tyr Ser Ile Val Leu Ser Leu Gly
        50                 55                 60

Glu Leu Ala Ser Val Tyr Pro Thr Thr Gly Ser Phe Gly Asp Tyr Ala
65                 70                 75                 80

Ser Arg Phe Ile Asn Pro Ser Thr Gly Tyr Met Val Phe Trp Met Tyr
                85                 90                 95

Trp Leu Ser Trp Val Leu Thr Val Ala Val Glu Tyr Ile Ala Ile Gly
                100                105                110

Leu Leu Met Gln Arg Trp Phe Pro Thr Ile Pro Val Tyr Val Trp Val
            115                120                125

Ile Val Cys Ile Ala Leu Leu Phe Leu Leu Asn Phe Phe Ser Val Lys
        130                135                140

Ile Phe Ala Thr Gly Glu Phe Leu Leu Ser Thr Ile Lys Val Leu Ala
145                150                155                160

Val Phe Val Phe Ile Val Leu Gly Cys Ile Gly Ile Val Tyr Ser Phe
                165                170                175

Tyr Leu His Gly Phe Glu Gly Val Ala Asn Phe Tyr Phe Asn Gly
            180                185                190

Glu Thr Gln Gly Leu Glu Lys Gly Phe Phe Pro Lys Gly Val Gly Ala
            195                200                205
```

Phe Phe Gly Ala Ile Leu Ala Val Ile Phe Tyr Thr Gly Thr Glu
            210                 215                 220

Ile Ile Gly Val Ala Ala Gly Glu Thr Lys Asp Ala Lys Lys Val Met
225                 230                 235                 240

Pro Lys Ala Ile Lys Ala Thr Leu Trp Arg Ile Val Phe Phe Phe Leu
                245                 250                 255

Gly Ala Val Phe Val Val Ser Val Phe Leu Pro Met Thr Asp Ser Ser
            260                 265                 270

Leu Thr Gln Ser Pro Phe Val Ser Ala Leu Glu Lys Ile Pro Leu Pro
        275                 280                 285

Phe Trp Gly Val Gly Ile Pro Tyr Ala Ala Asp Ile Met Asn Phe Val
    290                 295                 300

Ile Val Thr Ala Ile Leu Ser Thr Ala Asn Ser Gly Leu Tyr Ala Ser
305                 310                 315                 320

Gly Arg Met Ile Tyr Gly Leu Ser Gln Lys Lys Met Phe Phe Pro Leu
                325                 330                 335

Phe Ala Lys Leu Asn Ala Ser Gly Thr Pro Thr Tyr Ala Leu Tyr Leu
            340                 345                 350

Ser Leu Gly Val Thr Leu Ile Gly Met Leu Thr Glu Ala Phe Ala Pro
        355                 360                 365

Glu Lys Ile Met Ala Ser Leu Ile Asn Val Val Ser Phe Met Val Ile
    370                 375                 380

Ile Val Trp Ile Ser Ile Ser Val Ala Gln Tyr His Phe Arg Lys Glu
385                 390                 395                 400

Tyr Leu Ala Leu Arg Lys Ser Leu Lys Asp Leu Pro Tyr Lys Ala Pro
                405                 410                 415

Leu Asn Pro Leu Ile Gln Ile Ile Gly Ile Ser Gly Cys Leu Val Gly
            420                 425                 430

Leu Ile Gly Ala Tyr Met Asp Ala Asn Glu Arg Ile Gly Gly Tyr Leu
        435                 440                 445

Thr Leu Val Phe Met Gly Leu Cys Tyr Gly Ala Tyr Tyr Leu Ser Lys
    450                 455                 460

Asp Lys Trp Gly Tyr Gln Gln Glu Lys Gly Ile
465                 470                 475

<210> SEQ ID NO 58
<211> LENGTH: 18
<212> TYPE: PRT
<213> ORGANISM: artificial sequence
<220> FEATURE:
<223> OTHER INFORMATION: polypeptide or immunogenic fragment of
      Heliobacter spp genes

<400> SEQUENCE: 58

Gly Thr Gly Gly Asn Ile Ala Ser Ala Gly Pro Leu Ala Thr Leu Leu
1               5                   10                  15

Ala Tyr

<210> SEQ ID NO 59
<211> LENGTH: 14
<212> TYPE: PRT
<213> ORGANISM: artificial sequence
<220> FEATURE:
<223> OTHER INFORMATION: polypeptide or immunogenic fragment of
      Heliobacter spp genes

<400> SEQUENCE: 59

```
Ala Ile Gly Leu Leu Met Gln Arg Trp Phe Pro Thr Ile Pro
1               5                   10
```

<210> SEQ ID NO 60
<211> LENGTH: 37
<212> TYPE: PRT
<213> ORGANISM: artificial sequence
<220> FEATURE:
<223> OTHER INFORMATION: polypeptide or immunogenic fragment of
      Heliobacter spp genes

<400> SEQUENCE: 60

```
Val Tyr Ser Phe Tyr Leu His Gly Phe Glu Gly Val Phe Ala Asn Phe
1               5                   10                  15

Tyr Phe Asn Gly Glu Thr Gln Gly Leu Glu Lys Gly Phe Phe Pro Lys
            20                  25                  30

Gly Val Gly Ala Phe
        35
```

<210> SEQ ID NO 61
<211> LENGTH: 37
<212> TYPE: PRT
<213> ORGANISM: artificial sequence
<220> FEATURE:
<223> OTHER INFORMATION: polypeptide or immunogenic fragment of
      Heliobacter spp genes

<400> SEQUENCE: 61

```
Leu Pro Met Thr Asp Ser Ser Leu Thr Gln Ser Pro Phe Val Ser Ala
1               5                   10                  15

Leu Glu Lys Ile Pro Leu Pro Phe Trp Gly Val Gly Ile Pro Tyr Ala
            20                  25                  30

Ala Asp Ile Met Asn
        35
```

<210> SEQ ID NO 62
<211> LENGTH: 23
<212> TYPE: PRT
<213> ORGANISM: artificial sequence
<220> FEATURE:
<223> OTHER INFORMATION: polypeptide or immunogenic fragment of
      Heliobacter spp genes

<400> SEQUENCE: 62

```
Gly Val Thr Leu Ile Gly Met Leu Thr Glu Ala Phe Ala Pro Glu Lys
1               5                   10                  15

Ile Met Ala Ser Leu Ile Asn
            20
```

<210> SEQ ID NO 63
<211> LENGTH: 11
<212> TYPE: PRT
<213> ORGANISM: artificial sequence
<220> FEATURE:
<223> OTHER INFORMATION: polypeptide or immunogenic fragment of
      Heliobacter spp genes

<400> SEQUENCE: 63

```
Gly Ala Tyr Met Asp Ala Asn Glu Arg Ile Gly
1               5                   10
```

<210> SEQ ID NO 64
<211> LENGTH: 461
<212> TYPE: PRT
<213> ORGANISM: Mycobacterium tuberculosis

<400> SEQUENCE: 64

Met Pro Pro Thr Asp Arg Lys Ala Gly Ala Ile Ala Thr Thr Ser Gly
1               5                   10                  15

Leu Arg Pro Gly Leu Ser Gln Arg Gln Leu Asn Met Ile Ala Ile Gly
            20                  25                  30

Gly Val Ile Gly Ala Gly Leu Phe Val Gly Ser Gly Val Val Ile Arg
        35                  40                  45

Ala Thr Gly Pro Ala Ala Phe Leu Thr Tyr Ala Leu Cys Gly Ala Leu
    50                  55                  60

Ile Val Leu Val Met Arg Met Leu Gly Glu Met Ala Ala Ala Asn Pro
65                  70                  75                  80

Ser Thr Gly Ala Phe Ala Asp Tyr Ala Ala Lys Ala Leu Gly Gly Trp
                85                  90                  95

Ala Gly Phe Ser Val Gly Trp Leu Tyr Trp Tyr Phe Trp Val Ile Val
            100                 105                 110

Val Gly Phe Glu Ala Val Ala Gly Gly Lys Val Leu Thr Tyr Trp Ile
        115                 120                 125

Asp Ala Pro Leu Trp Leu Ala Ser Leu Cys Leu Met Met Met Met Thr
    130                 135                 140

Ala Thr Asn Leu Val Ser Val Ser Ser Phe Gly Glu Phe Glu Phe Trp
145                 150                 155                 160

Phe Ala Gly Val Lys Val Ala Thr Ile Val Gly Phe Leu Val Leu Gly
                165                 170                 175

Thr Ala Phe Ala Phe Gly Leu Leu Pro Gly His Gly Met Asp Phe Ser
            180                 185                 190

Asn Leu Ser Ala His Gly Gly Phe Phe Pro Asp Gly Val Gly Ala Val
        195                 200                 205

Phe Ala Ala Ile Val Val Ala Ile Phe Ser Met Thr Gly Thr Glu Val
    210                 215                 220

Val Thr Ile Ala Ala Ala Glu Ala Pro Asp Pro Gln Arg Ala Val Gln
225                 230                 235                 240

Arg Ala Met Ser Thr Val Val Ala Arg Ile Val Ile Phe Phe Val Gly
                245                 250                 255

Ser Val Phe Leu Leu Thr Val Ile Leu Pro Trp Asn Ser Leu Glu Leu
            260                 265                 270

Gly Ala Ser Pro Tyr Val Ala Ala Leu Arg His Met Gly Ile Gly Gly
        275                 280                 285

Ala Asp Gln Ile Met Asn Ala Val Val Leu Thr Ala Val Leu Ser Cys
    290                 295                 300

Leu Asn Ser Gly Leu Tyr Thr Ala Ser Arg Met Leu Phe Val Leu Ala
305                 310                 315                 320

Ala Arg Gln Glu Ala Pro Ala Gln Leu Val Lys Val Asn Arg Arg Gly
                325                 330                 335

Val Pro Thr Phe Ala Ile Met Gly Ser Ser Val Gly Phe Leu Cys
            340                 345                 350

Val Ile Met Ala Trp Val Ser Pro Ala Thr Val Phe Val Phe Leu Leu
    355                 360                 365

Asn Ser Ser Gly Ala Val Ile Leu Phe Val Tyr Leu Leu Ile Ala Leu
370                 375                 380

Ser Gln Ile Val Leu Arg Arg Gln Thr Ser Gly Gln Asn Leu Gly Val
385                 390                 395                 400

Arg Met Trp Leu Phe Pro Gly Leu Ser Ile Val Thr Val Thr Gly Ile

```
            405                 410                 415
Val Ala Val Leu Ala Arg Met Ala Phe Asp Tyr Ala Ala Arg Ser Gln
        420                 425                 430

Leu Trp Leu Ser Leu Leu Ser Trp Ala Val Val Gly Cys Tyr Leu
    435                 440                 445

Val Thr Thr Leu Val Arg Arg Pro Leu Asn Arg Pro Trp
    450                 455                 460

<210> SEQ ID NO 65
<211> LENGTH: 10
<212> TYPE: PRT
<213> ORGANISM: artificial sequence
<220> FEATURE:
<223> OTHER INFORMATION: polypeptide or immunogenic fragment of
      Myobacterium spp genes

<400> SEQUENCE: 65

Gly Val Val Ile Arg Ala Thr Gly Pro Ala
1               5                   10

<210> SEQ ID NO 66
<211> LENGTH: 25
<212> TYPE: PRT
<213> ORGANISM: artificial sequence
<220> FEATURE:
<223> OTHER INFORMATION: polypeptide or immunogenic fragment of
      Myobacterium spp genes

<400> SEQUENCE: 66

Val Ile Val Val Gly Phe Glu Ala Val Ala Gly Gly Lys Val Leu Thr
1               5                   10                  15

Tyr Trp Ile Asp Ala Pro Leu Trp Leu
            20                  25

<210> SEQ ID NO 67
<211> LENGTH: 28
<212> TYPE: PRT
<213> ORGANISM: artificial sequence
<220> FEATURE:
<223> OTHER INFORMATION: polypeptide or immunogenic fragment of
      Myobacterium spp genes

<400> SEQUENCE: 67

Ala Phe Gly Leu Leu Pro Gly His Gly Met Asp Phe Ser Asn Leu Ser
1               5                   10                  15

Ala His Gly Gly Phe Phe Pro Asp Gly Val Gly Ala
            20                  25

<210> SEQ ID NO 68
<211> LENGTH: 35
<212> TYPE: PRT
<213> ORGANISM: artificial sequence
<220> FEATURE:
<223> OTHER INFORMATION: polypeptide or immunogenic fragment of
      Myobacterium spp genes

<400> SEQUENCE: 68

Val Ile Leu Pro Trp Asn Ser Leu Glu Leu Gly Ala Ser Pro Tyr Val
1               5                   10                  15

Ala Ala Leu Arg His Met Gly Ile Gly Gly Ala Asp Gln Ile Met Asn
            20                  25                  30

Ala Val Val
        35
```

<210> SEQ ID NO 69
<211> LENGTH: 10
<212> TYPE: PRT
<213> ORGANISM: artificial sequence
<220> FEATURE:
<223> OTHER INFORMATION: polypeptide or immunogenic fragment of
      Myobacterium spp genes

<400> SEQUENCE: 69

Trp Val Ser Pro Ala Thr Val Phe Val Phe
1               5                   10

<210> SEQ ID NO 70
<211> LENGTH: 13
<212> TYPE: PRT
<213> ORGANISM: artificial sequence
<220> FEATURE:
<223> OTHER INFORMATION: polypeptide or immunogenic fragment of
      Myobacterium spp genes

<400> SEQUENCE: 70

Arg Met Ala Phe Asp Tyr Ala Ala Arg Ser Gln Leu Trp
1               5                   10

<210> SEQ ID NO 71
<211> LENGTH: 487
<212> TYPE: PRT
<213> ORGANISM: Pseudomonas aeruginosa

<400> SEQUENCE: 71

Met Thr Asp Leu Asn Thr Ser Gln Gly Gln Gln Leu Arg Arg Val Leu
1               5                   10                  15

Lys Pro Arg His Leu Asn Met Ile Ala Ile Gly Gly Ser Ile Gly Thr
                20                  25                  30

Gly Leu Phe Val Ala Ser Gly Ala Thr Val Ala Thr Ala Gly Pro Gly
            35                  40                  45

Gly Ala Leu Leu Ser Tyr Ala Leu Ile Gly Leu Met Val Tyr Phe Leu
        50                  55                  60

Met Thr Ser Leu Gly Glu Met Ala Ala Tyr Met Pro Val Ser Gly Ser
65                  70                  75                  80

Phe Cys Thr Tyr Gly Ser Arg Phe Val Glu Asp Gly Phe Gly Phe Ala
                85                  90                  95

Leu Gly Trp Asn Tyr Trp Tyr Asn Trp Ala Val Thr Ile Ala Ala Glu
                100                 105                 110

Leu Val Ala Ala Gln Leu Val Met Ser Phe Trp Phe Pro Glu Val Pro
            115                 120                 125

Gly Ile Tyr Trp Ser Ala Ile Phe Leu Gly Ile Met Phe Gly Leu Asn
        130                 135                 140

Val Ile Ser Ala Arg Gly Phe Gly Glu Ser Glu Phe Trp Phe Ala Leu
145                 150                 155                 160

Ile Lys Val Val Thr Val Val Ile Phe Ile Gly Val Gly Leu Ala Thr
                165                 170                 175

Ile Phe Gly Ile Met His Gly Val Glu Ser Pro Gly Phe Ser Asn Phe
            180                 185                 190

Thr Met Gly Asp Ala Pro Phe Val Gly Gly Phe Gln Ala Met Val Gly
        195                 200                 205

Val Ala Met Ile Ala Gly Phe Ser Phe Gln Gly Thr Glu Leu Ile Gly
        210                 215                 220

Ile Ala Ala Gly Glu Ser Glu Asn Pro Arg Lys Asn Ile Pro Ile Ala

```
                225                 230                 235                 240
Ile Arg Gln Val Phe Trp Arg Ile Leu Met Phe Tyr Ile Leu Ala Ile
                245                 250                 255

Phe Val Ile Gly Met Leu Ile Pro Tyr Thr Asp Pro Asn Leu Leu Lys
            260                 265                 270

Asn Asp Ala Ser Asp Ile Ser Val Ser Pro Phe Thr Leu Leu Phe Glu
            275                 280                 285

Arg Ala Gly Phe Ala Ala Ala Gly Val Met Asn Ala Val Ile Leu
            290                 295                 300

Ser Ala Ile Leu Ser Ala Gly Asn Ser Gly Met Tyr Ala Ser Thr Arg
305                 310                 315                 320

Met Leu Tyr Asn Leu Ala Leu Glu Gly Lys Ala Pro Arg Leu Phe Ser
                325                 330                 335

Arg Val Ser Arg Ser Gly Val Pro Arg Asn Ala Leu Tyr Ala Thr Thr
            340                 345                 350

Leu Val Gly Ala Leu Cys Phe Leu Thr Ser Ala Phe Gly Asp Ser Thr
            355                 360                 365

Val Tyr Thr Trp Leu Leu Asn Thr Ser Gly Met Cys Gly Phe Ile Ala
            370                 375                 380

Trp Leu Gly Ile Ala Ile Ser His Tyr Arg Phe Arg Lys Gly Tyr Leu
385                 390                 395                 400

Ala Gln Gly Gly Arg Leu Glu Asp Leu Pro Tyr Arg Ala Lys Leu Phe
                405                 410                 415

Pro Phe Gly Pro Leu Phe Ala Phe Ala Leu Cys Met Val Ile Thr Leu
            420                 425                 430

Gly Gln Asn Tyr Gln Ala Leu Val Gly Glu Arg Ile Asp Trp Ile Gly
            435                 440                 445

Leu Leu Ala Thr Tyr Ile Ser Leu Pro Leu Phe Leu Ala Ile Trp Leu
            450                 455                 460

Gly Tyr Arg Trp Lys Lys Arg Ala Arg Phe Val Arg Tyr His Glu Met
465                 470                 475                 480

Asp Val Ser Pro Thr Asn Thr
                485

<210> SEQ ID NO 72
<211> LENGTH: 18
<212> TYPE: PRT
<213> ORGANISM: artificial sequence
<220> FEATURE:
<223> OTHER INFORMATION: polypeptide or immunogenic fragment of
      Pseudomonas spp genes

<400> SEQUENCE: 72

Ala Thr Val Ala Thr Ala Gly Pro Gly Gly Ala Leu Leu Ser Tyr Ala
1               5                   10                  15

Leu Ile

<210> SEQ ID NO 73
<211> LENGTH: 15
<212> TYPE: PRT
<213> ORGANISM: artificial sequence
<220> FEATURE:
<223> OTHER INFORMATION: polypeptide or immunogenic fragment of
      Pseudomonas spp genes

<400> SEQUENCE: 73

Ala Gln Leu Val Met Ser Phe Trp Phe Pro Glu Val Pro Gly Ile
1               5                   10                  15
```

<210> SEQ ID NO 74
<211> LENGTH: 28
<212> TYPE: PRT
<213> ORGANISM: artificial sequence
<220> FEATURE:
<223> OTHER INFORMATION: polypeptide or immunogenic fragment of
      Pseudomonas spp genes

<400> SEQUENCE: 74

Ile Phe Gly Ile Met His Gly Val Glu Ser Pro Gly Phe Ser Asn Phe
1               5                   10                  15

Thr Met Gly Asp Ala Pro Phe Val Gly Gly Phe Gln
            20                  25

<210> SEQ ID NO 75
<211> LENGTH: 34
<212> TYPE: PRT
<213> ORGANISM: artificial sequence
<220> FEATURE:
<223> OTHER INFORMATION: polypeptide or immunogenic fragment of
      Pseudomonas spp genes

<400> SEQUENCE: 75

Met Leu Ile Pro Tyr Thr Asp Pro Asn Leu Leu Lys Asn Asp Ala Ser
1               5                   10                  15

Asp Ile Ser Val Ser Pro Phe Thr Leu Leu Phe Glu Arg Ala Gly Phe
            20                  25                  30

Ala Ala

<210> SEQ ID NO 76
<211> LENGTH: 14
<212> TYPE: PRT
<213> ORGANISM: artificial sequence
<220> FEATURE:
<223> OTHER INFORMATION: polypeptide or immunogenic fragment of
      Pseudomonas spp genes

<400> SEQUENCE: 76

Thr Ser Ala Phe Gly Asp Ser Thr Val Tyr Thr Trp Leu Leu
1               5                   10

<210> SEQ ID NO 77
<211> LENGTH: 16
<212> TYPE: PRT
<213> ORGANISM: artificial sequence
<220> FEATURE:
<223> OTHER INFORMATION: polypeptide or immunogenic fragment of
      Pseudomonas spp genes

<400> SEQUENCE: 77

Gly Gln Asn Tyr Gln Ala Leu Val Gly Glu Arg Ile Asp Trp Ile Gly
1               5                   10                  15

<210> SEQ ID NO 78
<211> LENGTH: 489
<212> TYPE: PRT
<213> ORGANISM: Shigella flexneri

<400> SEQUENCE: 78

Met Gly Ser Glu Thr Lys Thr Thr Glu Ala Pro Gly Leu Arg Arg Glu
1               5                   10                  15

Leu Lys Ala Arg His Leu Thr Met Ile Ala Ile Gly Gly Ser Ile Gly
            20                  25                  30

-continued

```
Thr Gly Leu Phe Val Ala Ser Gly Ala Thr Ile Ser Gln Ala Gly Pro
             35                  40                  45

Gly Gly Ala Leu Leu Ser Tyr Met Leu Ile Gly Leu Met Val Tyr Phe
 50                  55                  60

Leu Met Thr Ser Leu Gly Glu Leu Ala Ala Tyr Met Pro Val Ser Gly
 65                  70                  75                  80

Ser Phe Ala Thr Tyr Gly Gln Asn Tyr Val Glu Gly Phe Gly Phe
                 85                  90                  95

Ala Leu Gly Trp Asn Tyr Trp Tyr Asn Trp Ala Val Thr Ile Ala Val
                100                 105                 110

Asp Leu Val Ala Ala Gln Leu Val Met Ser Trp Trp Phe Pro Asp Thr
            115                 120                 125

Pro Gly Trp Ile Trp Ser Ala Leu Phe Leu Gly Val Ile Phe Leu Leu
        130                 135                 140

Asn Tyr Ile Ser Val Arg Gly Phe Gly Glu Ala Glu Tyr Trp Phe Ser
145                 150                 155                 160

Leu Ile Lys Val Thr Thr Val Ile Val Phe Ile Ile Val Gly Val Leu
                165                 170                 175

Met Ile Ile Gly Ile Phe Lys Gly Ala Gln Pro Ala Gly Trp Ser Asn
            180                 185                 190

Trp Thr Ile Gly Glu Ala Pro Phe Ala Gly Gly Phe Ala Ala Met Ile
        195                 200                 205

Gly Val Ala Met Ile Val Gly Phe Ser Phe Gln Gly Thr Glu Leu Ile
    210                 215                 220

Gly Ile Ala Ala Gly Glu Ser Glu Asp Pro Ala Lys Asn Ile Pro Arg
225                 230                 235                 240

Ala Val Arg Gln Val Phe Trp Arg Ile Leu Leu Phe Tyr Val Phe Ala
                245                 250                 255

Ile Leu Ile Ile Ser Leu Ile Ile Pro Tyr Thr Asp Pro Ser Leu Leu
            260                 265                 270

Arg Asn Asp Val Lys Asp Ile Ser Val Ser Pro Phe Thr Leu Val Phe
        275                 280                 285

Gln His Ala Gly Leu Leu Ser Ala Ala Ala Val Met Asn Ala Val Ile
    290                 295                 300

Leu Thr Ala Val Leu Ser Ala Gly Asn Ser Gly Met Tyr Ala Ser Thr
305                 310                 315                 320

Arg Met Leu Tyr Thr Leu Ala Cys Asp Gly Lys Ala Pro Arg Ile Phe
                325                 330                 335

Ala Lys Leu Ser Arg Gly Gly Val Pro Arg Asn Ala Leu Tyr Ala Thr
            340                 345                 350

Thr Val Ile Ala Gly Leu Cys Phe Leu Thr Ser Met Phe Gly Asn Gln
        355                 360                 365

Thr Val Tyr Leu Trp Leu Leu Asn Thr Ser Gly Met Thr Gly Phe Ile
    370                 375                 380

Ala Trp Leu Gly Ile Ala Ile Ser His Tyr Arg Phe Arg Arg Gly Tyr
385                 390                 395                 400

Val Leu Gln Gly His Asp Ile Asn Asp Leu Pro Tyr Arg Ser Gly Phe
                405                 410                 415

Phe Pro Leu Gly Pro Ile Phe Ala Phe Ile Leu Cys Leu Ile Ile Thr
            420                 425                 430

Leu Gly Gln Asn Tyr Glu Ala Phe Leu Lys Asp Thr Ile Asp Trp Gly
        435                 440                 445

Gly Val Ala Ala Thr Tyr Ile Gly Ile Pro Leu Phe Leu Ile Ile Trp
```

```
                    450                 455                 460
Phe Gly Tyr Lys Leu Ile Lys Gly Thr His Phe Val Arg Tyr Ser Glu
465                 470                 475                 480

Met Lys Phe Pro Gln Asn Asp Lys Lys
                485

<210> SEQ ID NO 79
<211> LENGTH: 20
<212> TYPE: PRT
<213> ORGANISM: artificial sequence
<220> FEATURE:
<223> OTHER INFORMATION: polypeptide or immunogenic fragment of Shigella
      spp genes

<400> SEQUENCE: 79

Gly Ala Thr Ile Ser Gln Ala Gly Pro Gly Gly Ala Leu Leu Ser Tyr
1               5                   10                  15

Met Leu Ile Gly
            20

<210> SEQ ID NO 80
<211> LENGTH: 18
<212> TYPE: PRT
<213> ORGANISM: artificial sequence
<220> FEATURE:
<223> OTHER INFORMATION: polypeptide or immunogenic fragment of Shigella
      spp genes

<400> SEQUENCE: 80

Ala Ala Gln Leu Val Met Ser Trp Trp Phe Pro Asp Thr Pro Gly Trp
1               5                   10                  15

Ile Trp

<210> SEQ ID NO 81
<211> LENGTH: 27
<212> TYPE: PRT
<213> ORGANISM: artificial sequence
<220> FEATURE:
<223> OTHER INFORMATION: polypeptide or immunogenic fragment of Shigella
      spp genes

<400> SEQUENCE: 81

Met Ile Ile Gly Ile Phe Lys Gly Ala Gln Pro Ala Gly Trp Ser Asn
1               5                   10                  15

Trp Thr Ile Gly Glu Ala Pro Phe Ala Gly Gly
                20                  25

<210> SEQ ID NO 82
<211> LENGTH: 29
<212> TYPE: PRT
<213> ORGANISM: artificial sequence
<220> FEATURE:
<223> OTHER INFORMATION: polypeptide or immunogenic fragment of Shigella
      spp genes

<400> SEQUENCE: 82

Ile Pro Tyr Thr Asp Pro Ser Leu Leu Arg Asn Asp Val Lys Asp Ile
1               5                   10                  15

Ser Val Ser Pro Phe Thr Leu Val Phe Gln His Ala Gly
                20                  25

<210> SEQ ID NO 83
<211> LENGTH: 13
<212> TYPE: PRT
```

```
<213> ORGANISM: artificial sequence
<220> FEATURE:
<223> OTHER INFORMATION: polypeptide or immunogenic fragment of Shigella
      spp genes

<400> SEQUENCE: 83

Thr Ser Met Phe Gly Asn Gln Thr Val Tyr Leu Trp Leu
1               5                   10

<210> SEQ ID NO 84
<211> LENGTH: 20
<212> TYPE: PRT
<213> ORGANISM: artificial sequence
<220> FEATURE:
<223> OTHER INFORMATION: polypeptide or immunogenic fragment of Shigella
      spp genes

<400> SEQUENCE: 84

Thr Leu Gly Gln Asn Tyr Glu Ala Phe Leu Lys Asp Thr Ile Asp Trp
1               5                   10                  15

Gly Gly Val Ala
            20

<210> SEQ ID NO 85
<211> LENGTH: 467
<212> TYPE: PRT
<213> ORGANISM: Streptococcus pneumonia

<400> SEQUENCE: 85

Met Glu Ser Lys Met Asn Ile Phe Arg Thr Lys Asn Val Ser Leu Asp
1               5                   10                  15

Lys Thr Glu Met His Arg His Leu Lys Leu Trp Asp Leu Ile Leu Leu
            20                  25                  30

Gly Ile Gly Ala Met Val Gly Thr Gly Val Phe Thr Ile Thr Gly Thr
        35                  40                  45

Ala Ala Ala Thr Leu Ala Gly Pro Ala Leu Val Ile Ser Ile Val Ile
    50                  55                  60

Ser Ala Leu Cys Val Gly Leu Ser Ala Leu Phe Phe Ala Glu Phe Ala
65                  70                  75                  80

Ser Arg Val Pro Ala Thr Gly Gly Ala Tyr Ser Tyr Leu Tyr Ala Ile
                85                  90                  95

Leu Gly Glu Phe Pro Ala Trp Leu Ala Gly Trp Leu Thr Met Met Glu
            100                 105                 110

Phe Met Thr Ala Ile Ser Gly Val Ala Ser Gly Trp Ala Ala Tyr Phe
        115                 120                 125

Lys Gly Leu Leu Ser Gln Tyr Gly Ile Ala Phe Pro Gln Ala Leu Asn
    130                 135                 140

Gly Thr Phe Asn Pro Gln Ala Gly Thr Phe Val Asp Leu Leu Pro Ile
145                 150                 155                 160

Leu Val Leu Val Leu Val Thr Ser Leu Val Leu Leu Asn Ala Lys Ala
                165                 170                 175

Ala Leu Arg Phe Asn Ser Ile Leu Val Ile Leu Lys Phe Ser Ala Leu
            180                 185                 190

Ala Leu Phe Val Leu Val Gly Ile Trp Asn Ile Lys Phe Asp Asn Trp
        195                 200                 205

Ser Asn Phe Ala Pro Tyr Gly Phe Gly Gln Ile Tyr Gly Ala Ser Thr
    210                 215                 220

Gly Ile Met Ala Gly Ala Ser Leu Met Phe Phe Gly Phe Leu Gly Phe
225                 230                 235                 240
```

```
Glu Ser Ile Ser Met Ala Val Asp Glu Val Lys Thr Pro Gln Lys Asn
            245                 250                 255

Ile Pro Arg Gly Ile Val Leu Ser Leu Ser Ile Val Thr Ile Leu Tyr
        260                 265                 270

Ala Leu Val Thr Leu Val Leu Thr Gly Val Val His Tyr Ser His Leu
        275                 280                 285

Asn Val Asp Asp Ala Val Ala Phe Ala Leu Arg Ser Val Gly Ile Ser
        290                 295                 300

Trp Ala Ala Asn Tyr Val Ser Leu Val Ala Ile Leu Thr Leu Ile Thr
305                 310                 315                 320

Val Cys Ile Ser Met Thr Tyr Ala Leu Ser Arg Met Ile Tyr Ser Leu
                325                 330                 335

Ala Arg Asp Gly Leu Val Pro Ala Ala Phe Lys Glu Leu Thr Lys Thr
            340                 345                 350

Ser Lys Ile Pro Lys Asn Ala Thr Ile Leu Thr Gly Leu Ala Ser Ala
        355                 360                 365

Val Ala Ala Gly Met Phe Pro Leu Ala Ser Ile Ala Ala Phe Leu Asn
        370                 375                 380

Ile Cys Thr Leu Ala Tyr Leu Ile Met Leu Ala Tyr Gly Leu Ile Arg
385                 390                 395                 400

Leu Arg Lys Glu Lys Gly Met Pro Lys Ala Gly Glu Phe Lys Thr Pro
                405                 410                 415

Leu Val Pro Leu Leu Pro Ile Leu Ser Ile Ile Cys Leu Ser Phe
            420                 425                 430

Met Leu Gln Tyr Asn Met Asn Thr Trp Ile Ala Phe Leu Val Ala Leu
            435                 440                 445

Leu Val Gly Ser Ile Ile Tyr Phe Thr Tyr Gly Tyr Lys His Ser Thr
        450                 455                 460

Ile Glu Glu
465

<210> SEQ ID NO 86
<211> LENGTH: 16
<212> TYPE: PRT
<213> ORGANISM: artificial sequence
<220> FEATURE:
<223> OTHER INFORMATION: polypeptide or immunogenic fragment of
      Streptococcus spp genes

<400> SEQUENCE: 86

Thr Ile Thr Gly Thr Ala Ala Thr Leu Ala Gly Pro Ala Leu Val
1               5                   10                  15

<210> SEQ ID NO 87
<211> LENGTH: 46
<212> TYPE: PRT
<213> ORGANISM: artificial sequence
<220> FEATURE:
<223> OTHER INFORMATION: polypeptide or immunogenic fragment of
      Streptococcus spp genes

<400> SEQUENCE: 87

Thr Met Met Glu Phe Met Thr Ala Ile Ser Gly Val Ala Ser Gly Trp
1               5                   10                  15

Ala Ala Tyr Phe Lys Gly Leu Leu Ser Gln Tyr Gly Ile Ala Phe Pro
            20                  25                  30

Gln Ala Leu Asn Gly Thr Phe Asn Pro Gln Ala Gly Thr Phe
        35                  40                  45
```

<210> SEQ ID NO 88
<211> LENGTH: 22
<212> TYPE: PRT
<213> ORGANISM: artificial sequence
<220> FEATURE:
<223> OTHER INFORMATION: polypeptide or immunogenic fragment of
Streptococcus spp genes

<400> SEQUENCE: 88

Ile Trp Asn Ile Lys Phe Asp Asn Trp Ser Asn Phe Ala Pro Tyr Gly
1 5 10 15

Phe Gly Gln Ile Tyr Gly
20

<210> SEQ ID NO 89
<211> LENGTH: 31
<212> TYPE: PRT
<213> ORGANISM: artificial sequence
<220> FEATURE:
<223> OTHER INFORMATION: polypeptide or immunogenic fragment of
Streptococcus spp genes

<400> SEQUENCE: 89

Thr Gly Val Val His Tyr Ser His Leu Asn Val Asp Asp Ala Val Ala
1 5 10 15

Phe Ala Leu Arg Ser Val Gly Ile Ser Trp Ala Ala Asn Tyr Val
20 25 30

<210> SEQ ID NO 90
<211> LENGTH: 10
<212> TYPE: PRT
<213> ORGANISM: artificial sequence
<220> FEATURE:
<223> OTHER INFORMATION: polypeptide or immunogenic fragment of
Streptococcus spp. genes

<400> SEQUENCE: 90

Met Phe Pro Leu Ala Ser Ile Ala Ala Phe
1 5 10

<210> SEQ ID NO 91
<211> LENGTH: 503
<212> TYPE: PRT
<213> ORGANISM: Yersinia pestis

<400> SEQUENCE: 91

Met Thr Gln Gln Asn Thr Lys Ile Pro Ala Gln Gln Gly Ala Gln Arg
1 5 10 15

Leu Arg Arg Glu Leu Lys Ser Arg His Leu Ala Met Ile Ala Ile Gly
20 25 30

Gly Ser Ile Gly Thr Gly Leu Phe Val Ala Ser Gly Ala Thr Val Ser
35 40 45

Gln Ala Gly Pro Gly Gly Ala Leu Leu Ser Tyr Ala Leu Ile Gly Leu
50 55 60

Met Val Tyr Phe Leu Met Thr Ser Leu Gly Glu Leu Ala Ala Phe Met
65 70 75 80

Pro Val Ser Gly Ser Phe Ser Thr Tyr Gly Ser Lys Tyr Val Glu Glu
85 90 95

Gly Phe Gly Phe Ala Leu Gly Trp Asn Tyr Trp Tyr Asn Trp Ala Val
100 105 110

Thr Ile Ala Val Asp Leu Val Ala Ala Gln Leu Val Met Asn Tyr Trp

```
            115                 120                 125
Phe Pro Asp Ala Pro Gly Trp Ile Trp Ser Ala Leu Phe Gly Leu
130                 135                 140

Met Phe Leu Leu Asn Tyr Ile Ser Val Lys Gly Phe Gly Glu Ala Glu
145                 150                 155                 160

Tyr Trp Phe Ser Leu Ile Lys Val Thr Thr Val Val Ile Phe Ile Ile
                165                 170                 175

Val Gly Val Met Met Ile Thr Gly Ile Met Lys Gly Gly Glu Thr Ala
                180                 185                 190

Gly Trp His Asn Trp Thr Ile Gly Asp Ala Pro Phe Ala Gly Gly Phe
                195                 200                 205

Ser Ala Met Ile Gly Val Ala Met Ile Val Gly Phe Ser Phe Gln Gly
                210                 215                 220

Thr Glu Leu Ile Gly Ile Ala Ala Gly Glu Ser Lys Asp Pro Gly Lys
225                 230                 235                 240

Asn Ile Pro Lys Ala Ile Arg Lys Val Phe Trp Arg Ile Leu Leu Phe
                245                 250                 255

Tyr Ile Phe Ala Ile Leu Ile Ile Ser Leu Ile Ile Pro Tyr Thr Asp
                260                 265                 270

Pro Ser Leu Leu Arg Asn Asp Val Lys Asp Ile Ser Val Ser Pro Phe
                275                 280                 285

Thr Leu Val Phe Gln Asn Ala Gly Leu Leu Ser Ala Ala Ala Val Met
290                 295                 300

Asn Ala Val Ile Leu Thr Ala Val Leu Ser Ala Gly Asn Ser Gly Met
305                 310                 315                 320

Tyr Ala Ser Thr Arg Met Leu Phe Thr Leu Ala Ser Glu Gly Lys Ala
                325                 330                 335

Pro Arg Ile Phe Ala Lys Leu Ser Lys Gly Gly Val Pro Arg Asn Ala
                340                 345                 350

Leu Tyr Ala Thr Thr Val Val Ala Gly Leu Cys Phe Leu Ser Ser Met
                355                 360                 365

Phe Gly Asn Gln Thr Val Tyr Leu Trp Leu Leu Asn Thr Ser Gly Met
370                 375                 380

Thr Gly Phe Ile Ala Trp Leu Gly Ile Ala Ile Ser His Tyr Arg Phe
385                 390                 395                 400

Arg Arg Gly Tyr Met Met Gln Gly Arg Asp Leu Asn Asp Leu Pro Tyr
                405                 410                 415

Gln Ser Gly Phe Phe Pro Leu Gly Pro Ile Phe Ala Phe Val Leu Cys
                420                 425                 430

Leu Ile Ile Thr Leu Gly Gln Asn Tyr Gln Ala Phe Leu Gln Asp Arg
                435                 440                 445

Ile Asp Trp Tyr Gly Val Thr Ala Thr Tyr Ile Gly Ile Pro Leu Phe
                450                 455                 460

Leu Val Ile Trp Phe Gly Tyr Lys Leu Ser Arg Gly Thr Arg Val Val
465                 470                 475                 480

Lys Tyr Gln Glu Met Glu Phe Pro Lys Trp Arg Asp Glu Ser Glu Glu
                485                 490                 495

His Gln Lys Pro Thr Ser Arg
            500

<210> SEQ ID NO 92
<211> LENGTH: 23
<212> TYPE: PRT
<213> ORGANISM: artificial sequence
```

```
<220> FEATURE:
<223> OTHER INFORMATION: polypeptide or immunogenic fragment of Yersinia
      spp genes

<400> SEQUENCE: 92

Val Ala Ser Gly Ala Thr Val Ser Gln Ala Gly Pro Gly Ala Leu
1               5                   10                  15

Leu Ser Tyr Ala Leu Ile Gly
            20

<210> SEQ ID NO 93
<211> LENGTH: 18
<212> TYPE: PRT
<213> ORGANISM: artificial sequence
<220> FEATURE:
<223> OTHER INFORMATION: polypeptide or immunogenic fragment of Yersinia
      spp genes

<400> SEQUENCE: 93

Val Ala Ala Gln Leu Val Met Asn Tyr Trp Phe Pro Asp Ala Pro Gly
1               5                   10                  15

Trp Ile

<210> SEQ ID NO 94
<211> LENGTH: 30
<212> TYPE: PRT
<213> ORGANISM: artificial sequence
<220> FEATURE:
<223> OTHER INFORMATION: polypeptide or immunogenic fragment of Yersinia
      spp genes

<400> SEQUENCE: 94

Met Ile Thr Gly Ile Met Lys Gly Gly Glu Thr Ala Gly Trp His Asn
1               5                   10                  15

Trp Thr Ile Gly Asp Ala Pro Phe Ala Gly Gly Phe Ser Ala
            20                  25                  30

<210> SEQ ID NO 95
<211> LENGTH: 30
<212> TYPE: PRT
<213> ORGANISM: artificial sequence
<220> FEATURE:
<223> OTHER INFORMATION: polypeptide or immunogenic fragment of Yersinia
      spp genes

<400> SEQUENCE: 95

Ile Pro Tyr Thr Asp Pro Ser Leu Leu Arg Asn Asp Val Lys Asp Ile
1               5                   10                  15

Ser Val Ser Pro Phe Thr Leu Val Phe Gln Asn Ala Gly Leu
            20                  25                  30

<210> SEQ ID NO 96
<211> LENGTH: 15
<212> TYPE: PRT
<213> ORGANISM: artificial sequence
<220> FEATURE:
<223> OTHER INFORMATION: polypeptide or immunogenic fragment of Yersinia
      spp genes

<400> SEQUENCE: 96

Ser Ser Met Phe Gly Asn Gln Thr Val Tyr Leu Trp Leu Leu Asn
1               5                   10                  15

<210> SEQ ID NO 97
<211> LENGTH: 20
```

```
<212> TYPE: PRT
<213> ORGANISM: artificial sequence
<220> FEATURE:
<223> OTHER INFORMATION: polypeptide or immunogenic fragment of Yersinia
      spp genes

<400> SEQUENCE: 97

Ile Thr Leu Gly Gln Asn Tyr Gln Ala Phe Leu Gln Asp Arg Ile Asp
1               5                   10                  15

Trp Tyr Gly Val
            20

<210> SEQ ID NO 98
<211> LENGTH: 455
<212> TYPE: PRT
<213> ORGANISM: Streptococcus agalactiae

<400> SEQUENCE: 98

Met Glu Asn His Arg Tyr Glu Asp Glu Gly Lys Phe Gln Arg Lys Met
1               5                   10                  15

Thr Ser Arg His Leu Phe Met Leu Ser Leu Gly Gly Val Ile Gly Thr
                20                  25                  30

Gly Leu Phe Leu Ser Ser Gly Tyr Thr Ile Ala Gln Ala Gly Pro Leu
            35                  40                  45

Gly Ala Val Leu Ser Tyr Leu Ile Gly Ala Val Val Tyr Leu Val
        50                  55                  60

Met Leu Ser Leu Gly Glu Leu Ala Val Ala Met Pro Val Thr Gly Ser
65                  70                  75                  80

Phe His Thr Tyr Ala Thr Lys Phe Ile Ser Pro Gly Thr Gly Phe Thr
                85                  90                  95

Val Ala Trp Leu Tyr Trp Ile Cys Trp Thr Val Ala Leu Gly Thr Glu
            100                 105                 110

Phe Leu Gly Ala Ala Met Leu Met Gln Arg Trp Phe Pro Asp Val Pro
        115                 120                 125

Ala Trp Ala Phe Ala Ser Phe Phe Ala Leu Val Ile Phe Gly Leu Asn
130                 135                 140

Ala Leu Ser Val Arg Phe Phe Ala Glu Ala Glu Ser Phe Phe Ser Ser
145                 150                 155                 160

Ile Lys Val Ile Ala Ile Ile Phe Ile Ile Leu Gly Leu Gly Ala
                165                 170                 175

Met Phe Gly Leu Val Ser Phe Glu Gly Gln His Lys Ala Ile Leu Phe
            180                 185                 190

Thr His Leu Thr Ala Asn Gly Asp Phe Pro Asn Gly Ile Val Ala Val
        195                 200                 205

Val Ser Val Met Leu Ala Val Asn Tyr Ala Phe Ser Gly Thr Glu Leu
    210                 215                 220

Ile Gly Ile Ala Ala Gly Glu Thr Asp Asn Pro Lys Glu Ala Val Pro
225                 230                 235                 240

Arg Ala Ile Lys Thr Thr Ile Gly Arg Leu Val Phe Phe Val Leu
                245                 250                 255

Thr Ile Val Val Leu Ala Ser Leu Leu Pro Met Lys Glu Ala Gly Val
            260                 265                 270

Ser Thr Ala Pro Phe Val Asp Val Phe Asp Lys Met Gly Val Pro Phe
        275                 280                 285

Ala Ala Asp Ile Met Asn Phe Val Ile Leu Thr Ala Ile Leu Ser Ala
    290                 295                 300
```

```
Gly Asn Ser Gly Leu Tyr Ala Ser Ser Arg Met Leu Trp Ser Leu Ala
305                 310                 315                 320

Asn Glu Gly Met Leu Ser Lys Ser Val Val Lys Ile Asn Lys His Gly
            325                 330                 335

Val Pro Met Arg Ala Leu Leu Leu Ser Met Ala Gly Ala Val Leu Ser
            340                 345                 350

Leu Phe Ser Ser Ile Tyr Ala Ala Asp Thr Val Tyr Leu Ala Leu Val
        355                 360                 365

Ser Ile Ala Gly Phe Ala Val Val Val Trp Leu Ala Ile Pro Val
        370                 375                 380

Ala Gln Ile Asn Phe Arg Lys Glu Phe Leu Lys Glu Asn Arg Leu Glu
385                 390                 395                 400

Asp Leu Ser Tyr Lys Thr Pro Phe Thr Pro Val Leu Pro Tyr Ile Thr
            405                 410                 415

Ile Val Leu Leu Leu Ile Ser Ile Val Gly Ile Ala Trp Asp Ser Ser
            420                 425                 430

Gln Arg Ala Gly Leu Tyr Phe Gly Val Pro Phe Ile Ile Leu Cys Tyr
            435                 440                 445

Ile Tyr His Lys Leu Arg Tyr
            450                 455

<210> SEQ ID NO 99
<211> LENGTH: 20
<212> TYPE: PRT
<213> ORGANISM: artificial sequence
<220> FEATURE:
<223> OTHER INFORMATION: polypeptide or immunogenic fragment of
      Streptococcus spp genes

<400> SEQUENCE: 99

Gly Tyr Thr Ile Ala Gln Ala Gly Pro Leu Gly Ala Val Leu Ser Tyr
1               5                   10                  15

Leu Ile Gly Ala
            20

<210> SEQ ID NO 100
<211> LENGTH: 24
<212> TYPE: PRT
<213> ORGANISM: artificial sequence
<220> FEATURE:
<223> OTHER INFORMATION: polypeptide or immunogenic fragment of
      Streptococcus spp genes

<400> SEQUENCE: 100

Ala Leu Gly Thr Glu Phe Leu Gly Ala Ala Met Leu Met Gln Arg Trp
1               5                   10                  15

Phe Pro Asp Val Pro Ala Trp Ala
            20

<210> SEQ ID NO 101
<211> LENGTH: 34
<212> TYPE: PRT
<213> ORGANISM: artificial sequence
<220> FEATURE:
<223> OTHER INFORMATION: polypeptide or immunogenic fragment of
      Streptococcus spp genes

<400> SEQUENCE: 101

Met Phe Gly Leu Val Ser Phe Glu Gly Gln His Lys Ala Ile Leu Phe
1               5                   10                  15

Thr His Leu Thr Ala Asn Gly Asp Phe Pro Asn Gly Ile Val Ala Val
```

Val Ser

<210> SEQ ID NO 102
<211> LENGTH: 32
<212> TYPE: PRT
<213> ORGANISM: artificial sequence
<220> FEATURE:
<223> OTHER INFORMATION: polypeptide or immunogenic fragment of
      Streptococcus spp genes

<400> SEQUENCE: 102

Leu Leu Pro Met Lys Glu Ala Gly Val Ser Thr Ala Pro Phe Val Asp
1               5                   10                  15

Val Phe Asp Lys Met Gly Val Pro Phe Ala Ala Asp Ile Met Asn Phe
            20                  25                  30

<210> SEQ ID NO 103
<211> LENGTH: 14
<212> TYPE: PRT
<213> ORGANISM: artificial sequence
<220> FEATURE:
<223> OTHER INFORMATION: polypeptide or immunogenic fragment of
      Streptococcus spp genes

<400> SEQUENCE: 103

Ser Ile Tyr Ala Ala Asp Thr Val Tyr Leu Ala Leu Val Ser
1               5                   10

<210> SEQ ID NO 104
<211> LENGTH: 12
<212> TYPE: PRT
<213> ORGANISM: artificial sequence
<220> FEATURE:
<223> OTHER INFORMATION: polypeptide or immunogenic fragment of
      Streptococcus spp genes

<400> SEQUENCE: 104

Gly Ile Ala Trp Asp Ser Ser Gln Arg Ala Gly Leu
1               5                   10

<210> SEQ ID NO 105
<211> LENGTH: 459
<212> TYPE: PRT
<213> ORGANISM: Streptococcus pyogenes

<400> SEQUENCE: 105

Met Ser Ile Lys Glu Gln Thr Asp Asn Asn Glu Leu Glu Asn Gly Met
1               5                   10                  15

Val Arg Gly Leu Glu Asn Arg His Val Gln Leu Ile Ala Ile Ala Gly
            20                  25                  30

Thr Ile Gly Thr Gly Leu Phe Leu Gly Ala Gly Arg Ser Ile Ala Leu
        35                  40                  45

Thr Gly Pro Ser Ile Ile Phe Val Tyr Met Ile Thr Gly Ala Phe Met
    50                  55                  60

Phe Met Met Met Arg Ala Ile Gly Glu Met Leu Tyr Tyr Asp Pro Asp
65                  70                  75                  80

Gln His Thr Phe Ile Asn Phe Ile Ser Lys Tyr Ile Gly Pro Gly Trp
                85                  90                  95

Gly Tyr Phe Ser Gly Leu Ser Tyr Trp Ile Ser Leu Ile Phe Ile Gly
            100                 105                 110

Met Ala Glu Ile Thr Ala Val Gly Ala Tyr Val Gln Phe Trp Phe Pro

```
                    115                 120                 125
Ser Trp Pro Ala Trp Leu Ile Gln Leu Val Phe Leu Val Leu Leu Ser
    130                 135                 140

Ser Ile Asn Leu Ile Ala Val Arg Val Phe Gly Glu Thr Glu Phe Trp
145                 150                 155                 160

Phe Ala Met Ile Lys Ile Leu Ala Ile Leu Ala Leu Ile Ala Thr Ala
                    165                 170                 175

Ile Phe Met Val Leu Thr Gly Phe Glu Thr His Thr Gly His Ala Ser
                180                 185                 190

Leu Ser Asn Ile Phe Asp His Phe Ser Met Phe Pro Asn Gly Lys Leu
                195                 200                 205

Lys Phe Phe Met Ala Phe Gln Met Val Phe Ala Tyr Gln Ala Ile
            210                 215                 220

Glu Phe Val Gly Ile Thr Thr Ser Glu Thr Ala Asn Pro Arg Lys Val
225                 230                 235                 240

Leu Pro Lys Ala Ile Gln Glu Ile Pro Thr Arg Ile Val Ile Phe Tyr
                    245                 250                 255

Val Gly Ala Leu Val Ser Ile Met Ala Ile Val Pro Trp His Gln Leu
                260                 265                 270

Pro Val Asp Glu Ser Pro Phe Val Met Val Phe Lys Leu Ile Gly Ile
                275                 280                 285

Lys Trp Ala Ala Ala Leu Ile Asn Phe Val Val Leu Thr Ser Ala Ala
            290                 295                 300

Ser Ala Leu Asn Ser Thr Leu Tyr Ser Thr Gly Arg His Leu Tyr Gln
305                 310                 315                 320

Ile Ala Asn Glu Thr Pro Asn Ala Leu Thr Asn Arg Leu Lys Ile Asn
                    325                 330                 335

Thr Leu Ser Arg Gln Gly Val Pro Ser Arg Ala Ile Ile Ala Ser Ala
                340                 345                 350

Val Val Val Gly Ile Ser Ala Leu Ile Asn Ile Leu Pro Gly Val Ala
                355                 360                 365

Asp Ala Phe Ser Leu Ile Thr Ala Ser Ser Gly Val Tyr Ile Ala
            370                 375                 380

Ile Tyr Ala Leu Thr Met Ile Ala His Trp Lys Tyr Arg Gln Ser Lys
385                 390                 395                 400

Asp Phe Met Ala Asp Gly Tyr Leu Met Pro Lys Tyr Lys Val Thr Thr
                    405                 410                 415

Pro Leu Thr Leu Ala Phe Phe Ala Phe Val Phe Ile Ser Leu Phe Leu
                420                 425                 430

Gln Glu Ser Thr Tyr Ile Gly Ala Ile Gly Ala Thr Ile Trp Ile Ile
                435                 440                 445

Ile Phe Gly Ile Tyr Ser Asn Val Lys Phe Lys
            450                 455

<210> SEQ ID NO 106
<211> LENGTH: 16
<212> TYPE: PRT
<213> ORGANISM: artificial sequence
<220> FEATURE:
<223> OTHER INFORMATION: polypeptide or immunogenic fragment of
      Streptococcus spp genes

<400> SEQUENCE: 106

Leu Gly Ala Gly Arg Ser Ile Ala Leu Thr Gly Pro Ser Ile Ile Phe
1               5                   10                  15
```

```
<210> SEQ ID NO 107
<211> LENGTH: 23
<212> TYPE: PRT
<213> ORGANISM: artificial sequence
<220> FEATURE:
<223> OTHER INFORMATION: polypeptide or immunogenic fragment of
      Streptococcus spp genes

<400> SEQUENCE: 107

Gly Met Ala Glu Ile Thr Ala Val Gly Ala Tyr Val Gln Phe Trp Phe
1               5                   10                  15

Pro Ser Trp Pro Ala Trp Leu
            20

<210> SEQ ID NO 108
<211> LENGTH: 33
<212> TYPE: PRT
<213> ORGANISM: artificial sequence
<220> FEATURE:
<223> OTHER INFORMATION: polypeptide or immunogenic fragment of
      Streptococcus spp genes

<400> SEQUENCE: 108

Met Val Leu Thr Gly Phe Glu Thr His Thr Gly His Ala Ser Leu Ser
1               5                   10                  15

Asn Ile Phe Asp His Phe Ser Met Phe Pro Asn Gly Lys Leu Lys Phe
            20                  25                  30

Phe

<210> SEQ ID NO 109
<211> LENGTH: 24
<212> TYPE: PRT
<213> ORGANISM: artificial sequence
<220> FEATURE:
<223> OTHER INFORMATION: polypeptide or immunogenic fragment of
      Streptococcus spp genes

<400> SEQUENCE: 109

Trp His Gln Leu Pro Val Asp Glu Ser Pro Phe Val Met Val Phe Lys
1               5                   10                  15

Leu Ile Gly Ile Lys Trp Ala Ala
            20

<210> SEQ ID NO 110
<211> LENGTH: 13
<212> TYPE: PRT
<213> ORGANISM: artificial sequence
<220> FEATURE:
<223> OTHER INFORMATION: polypeptide or immunogenic fragment of
      Streptococcus spp genes

<400> SEQUENCE: 110

Ile Asn Ile Leu Pro Gly Val Ala Asp Ala Phe Ser Leu
1               5                   10

<210> SEQ ID NO 111
<211> LENGTH: 8
<212> TYPE: PRT
<213> ORGANISM: artificial sequence
<220> FEATURE:
<223> OTHER INFORMATION: polypeptide or immunogenic fragment of
      Streptococcus spp genes

<400> SEQUENCE: 111

Phe Leu Gln Glu Ser Thr Tyr Ile
```

-continued

```
<210> SEQ ID NO 112
<211> LENGTH: 338
<212> TYPE: PRT
<213> ORGANISM: Bacillus anthracis

<400> SEQUENCE: 112

Met Glu Lys Asn Thr Ile Ile Leu Gly Ile Glu Thr Ser Cys Asp Glu
1               5                   10                  15

Thr Ala Val Ala Val Val Lys Asn Gly Thr Glu Ile Ile Ala Asn Val
            20                  25                  30

Val Ala Ser Gln Ile Glu Ser His Lys Arg Phe Gly Gly Val Val Pro
        35                  40                  45

Glu Ile Ala Ser Arg His His Val Glu Ile Thr Val Val Leu Glu
    50                  55                  60

Glu Ala Leu Lys Glu Ala Asn Ile Thr Phe Asp Asp Ile Asp Ala Ile
65                  70                  75                  80

Ala Val Thr Glu Gly Pro Gly Leu Val Gly Ala Leu Leu Ile Gly Val
                85                  90                  95

Asn Ala Ala Lys Ala Val Ala Phe Ala His Asp Ile Pro Leu Val Gly
            100                 105                 110

Val His His Ile Ala Gly His Ile Tyr Ala Asn Arg Leu Val Lys Glu
        115                 120                 125

Val Gln Phe Pro Leu Leu Ser Leu Val Val Ser Gly His Thr Glu
    130                 135                 140

Leu Val Tyr Met Lys Glu His Gly Ser Phe Glu Val Ile Gly Glu Thr
145                 150                 155                 160

Arg Asp Asp Ala Ala Gly Glu Ala Tyr Asp Lys Val Ala Arg Thr Leu
                165                 170                 175

Ser Met Pro Tyr Pro Gly Gly Pro His Ile Asp Arg Leu Ala His Glu
            180                 185                 190

Gly Lys Pro Thr Ile Asp Leu Pro Arg Ala Trp Leu Glu Pro Asp Ser
        195                 200                 205

Tyr Asp Phe Ser Phe Ser Gly Leu Lys Ser Ala Val Ile Asn Thr Val
    210                 215                 220

His Asn Ala Lys Gln Arg Gly Ile Glu Ile Ala Pro Glu Asp Leu Ala
225                 230                 235                 240

Ala Ser Phe Gln Glu Ser Val Ile Asp Val Leu Val Thr Lys Ala Ser
                245                 250                 255

Arg Ala Ala Asp Ala Tyr Asn Val Lys Gln Val Leu Leu Ala Gly Gly
            260                 265                 270

Val Ala Ala Asn Lys Gly Leu Arg Ala Arg Leu Glu Thr Glu Phe Ala
        275                 280                 285

Gln Lys Glu Asn Val Glu Leu Ile Ile Pro Pro Leu Ser Leu Cys Thr
    290                 295                 300

Asp Asn Ala Ala Met Ile Ala Ala Gly Thr Ile Ala Tyr Glu Gln
305                 310                 315                 320

Gly Lys Arg Ala Thr Leu Ala Leu Asn Ala Asn Pro Gly Leu Asp Ile
                325                 330                 335

Glu Ala

<210> SEQ ID NO 113
<211> LENGTH: 359
<212> TYPE: PRT
```

<213> ORGANISM: Burkholderia mallei

<400> SEQUENCE: 113

Met Arg Thr Arg Ala Ser Met Arg Pro Pro His Thr Ile Met Leu Val
1               5                   10                  15

Leu Gly Ile Glu Ser Ser Cys Asp Glu Thr Gly Leu Ala Leu Tyr Asp
            20                  25                  30

Thr Glu Arg Gly Leu Leu Ala His Ala Leu His Ser Gln Ile Ala Met
        35                  40                  45

His Arg Glu Tyr Gly Gly Val Val Pro Glu Leu Ala Ser Arg Asp His
    50                  55                  60

Ile Arg Arg Ala Leu Pro Leu Leu Glu Glu Val Leu Ala Ala Ser Gly
65                  70                  75                  80

Ala Arg Arg Asp Asp Ile Asp Ala Ile Ala Phe Thr Gln Gly Pro Gly
                85                  90                  95

Leu Ala Gly Ala Leu Leu Val Gly Ala Ser Ile Ala Asn Ala Leu Ala
            100                 105                 110

Phe Ala Trp Asp Lys Pro Thr Ile Gly Ile His His Leu Glu Gly His
        115                 120                 125

Leu Leu Ser Pro Leu Leu Val Ala Glu Pro Pro Phe Pro Phe Val
130                 135                 140

Ala Leu Leu Val Ser Gly Gly His Thr Gln Leu Met Arg Val Ser Asp
145                 150                 155                 160

Val Gly Val Tyr Glu Thr Leu Gly Glu Thr Leu Asp Asp Ala Ala Gly
                165                 170                 175

Glu Ala Phe Asp Lys Thr Ala Lys Leu Leu Gly Leu Gly Tyr Pro Gly
            180                 185                 190

Gly Pro Glu Val Ser Arg Leu Ala Glu Ala Gly Thr Pro Gly Ala Val
        195                 200                 205

Val Leu Pro Arg Pro Met Leu His Ser Gly Asp Leu Asp Phe Ser Phe
210                 215                 220

Ser Gly Leu Lys Thr Ala Val Leu Thr Gln Met Lys Lys Leu Glu Ala
225                 230                 235                 240

Ala His Ala Gly Gly Ala Val Leu Glu Arg Ala Lys Ala Asp Leu Ala
                245                 250                 255

Arg Gly Phe Val Asp Ala Ala Val Asp Val Leu Val Ala Lys Ser Leu
            260                 265                 270

Ala Ala Leu Lys Ala Thr Arg Leu Lys Arg Leu Val Val Ala Gly Gly
        275                 280                 285

Val Gly Ala Asn Arg Gln Leu Arg Ala Ala Leu Ser Ala Ala Ala Gln
290                 295                 300

Lys Arg Gly Phe Asp Val His Tyr Pro Asp Leu Ala Leu Cys Thr Asp
305                 310                 315                 320

Asn Gly Ala Met Ile Ala Leu Ala Gly Ala Leu Arg Leu Ala Arg Trp
                325                 330                 335

Pro Ser Gln Ala Ser Arg Asp Tyr Ala Phe Thr Val Lys Pro Arg Trp
            340                 345                 350

Asp Leu Ala Ser Leu Ala Arg
        355

<210> SEQ ID NO 114
<211> LENGTH: 253
<212> TYPE: PRT
<213> ORGANISM: Artificial Sequence
<220> FEATURE:

<223> OTHER INFORMATION: polypeptide or immunogenic fragment of
      Burkholderia spp genes

<400> SEQUENCE: 114

Ile Ala Asn Ala Leu Ala Phe Ala Trp Asp Lys Pro Thr Ile Gly Ile
1               5                   10                  15

His His Leu Glu Gly His Leu Leu Ser Pro Leu Val Ala Glu Pro
            20                  25                  30

Pro Pro Phe Pro Phe Val Ala Leu Leu Val Ser Gly Gly His Thr Gln
        35                  40                  45

Leu Met Arg Val Ser Asp Val Gly Val Tyr Glu Thr Leu Gly Glu Thr
    50                  55                  60

Leu Asp Asp Ala Ala Gly Glu Ala Phe Asp Lys Thr Ala Lys Leu Leu
65                  70                  75                  80

Gly Leu Gly Tyr Pro Gly Gly Pro Glu Val Ser Arg Leu Ala Glu Ala
                85                  90                  95

Gly Thr Pro Gly Ala Val Val Leu Pro Arg Pro Met Leu His Ser Gly
            100                 105                 110

Asp Leu Asp Phe Ser Phe Ser Gly Leu Lys Thr Ala Val Leu Thr Gln
        115                 120                 125

Met Lys Lys Leu Glu Ala Ala His Ala Gly Gly Ala Val Leu Glu Arg
    130                 135                 140

Ala Lys Ala Asp Leu Ala Arg Gly Phe Val Asp Ala Ala Val Asp Val
145                 150                 155                 160

Leu Val Ala Lys Ser Leu Ala Ala Leu Lys Ala Thr Arg Leu Lys Arg
                165                 170                 175

Leu Val Val Ala Gly Gly Val Gly Ala Asn Arg Gln Leu Arg Ala Ala
            180                 185                 190

Leu Ser Ala Ala Gln Lys Arg Gly Phe Asp Val His Tyr Pro Asp
        195                 200                 205

Leu Ala Leu Cys Thr Asp Asn Gly Ala Met Ile Ala Leu Ala Gly Ala
    210                 215                 220

Leu Arg Leu Ala Arg Trp Pro Ser Gln Ala Ser Arg Asp Tyr Ala Phe
225                 230                 235                 240

Thr Val Lys Pro Arg Trp Asp Leu Ala Ser Leu Ala Arg
                245                 250

<210> SEQ ID NO 115
<211> LENGTH: 359
<212> TYPE: PRT
<213> ORGANISM: Burkholderia pseudomallei

<400> SEQUENCE: 115

Met Arg Thr Arg Ala Ser Met Arg Pro Pro His Thr Ile Met Leu Val
1               5                   10                  15

Leu Gly Ile Glu Ser Ser Cys Asp Glu Thr Gly Leu Ala Leu Tyr Asp
            20                  25                  30

Thr Glu Arg Gly Leu Leu Ala His Ala Leu His Ser Gln Ile Ala Met
        35                  40                  45

His Arg Glu Tyr Gly Gly Val Val Pro Glu Leu Ala Ser Arg Asp His
    50                  55                  60

Ile Arg Arg Ala Leu Pro Leu Leu Glu Glu Val Leu Ala Ala Ser Gly
65                  70                  75                  80

Ala Arg Arg Asp Asp Ile Asp Ala Ile Ala Phe Thr Gln Gly Pro Gly
                85                  90                  95

Leu Ala Gly Ala Leu Leu Val Gly Ala Ser Ile Ala Asn Ala Leu Ala
                100                 105                 110

Phe Ala Trp Asp Lys Pro Thr Ile Gly Ile His His Leu Glu Gly His
        115                 120                 125

Leu Leu Ser Pro Leu Leu Val Ala Glu Pro Pro Phe Pro Phe Val
    130                 135                 140

Ala Leu Leu Val Ser Gly Gly His Thr Gln Leu Met Arg Val Ser Asp
145                 150                 155                 160

Val Gly Val Tyr Glu Thr Leu Gly Glu Thr Leu Asp Asp Ala Ala Gly
                165                 170                 175

Glu Ala Phe Asp Lys Thr Ala Lys Leu Leu Gly Leu Gly Tyr Pro Gly
            180                 185                 190

Gly Pro Glu Val Ser Arg Leu Ala Glu Ala Gly Thr Pro Gly Ala Val
        195                 200                 205

Val Leu Pro Arg Pro Met Leu His Ser Gly Asp Leu Asp Phe Ser Phe
210                 215                 220

Ser Gly Leu Lys Thr Ala Val Leu Thr Gln Met Lys Lys Leu Glu Ala
225                 230                 235                 240

Ala His Ala Gly Gly Ala Val Leu Glu Arg Ala Lys Ala Asp Leu Ala
                245                 250                 255

Arg Gly Phe Val Asp Ala Ala Val Asp Val Leu Val Ala Lys Ser Leu
            260                 265                 270

Ala Ala Leu Lys Thr Thr Arg Leu Lys Arg Leu Val Val Ala Gly Gly
        275                 280                 285

Val Gly Ala Asn Arg Gln Leu Arg Ala Ala Leu Ser Ala Ala Ala Gln
    290                 295                 300

Lys Arg Gly Phe Asp Val His Tyr Pro Asp Leu Ala Leu Cys Thr Asp
305                 310                 315                 320

Asn Gly Ala Met Ile Ala Leu Ala Gly Ala Leu Arg Leu Thr Arg Trp
                325                 330                 335

Pro Ser Gln Ala Ser Arg Asp Tyr Ala Phe Thr Val Lys Pro Arg Trp
            340                 345                 350

Asp Leu Ala Ser Leu Ala Arg
        355

<210> SEQ ID NO 116
<211> LENGTH: 265
<212> TYPE: PRT
<213> ORGANISM: Artificial Sequence
<220> FEATURE:
<223> OTHER INFORMATION: polypeptide or immunogenic fragment of
      Burkholderia spp genes

<400> SEQUENCE: 116

Pro Gly Leu Ala Gly Ala Leu Leu Val Gly Ala Ser Ile Ala Asn Ala
1               5                   10                  15

Leu Ala Phe Ala Trp Asp Lys Pro Thr Ile Gly Ile His His Leu Glu
                20                  25                  30

Gly His Leu Leu Ser Pro Leu Leu Val Ala Glu Pro Pro Phe Pro
            35                  40                  45

Phe Val Ala Leu Leu Val Ser Gly Gly His Thr Gln Leu Met Arg Val
        50                  55                  60

Ser Asp Val Gly Val Tyr Glu Thr Leu Gly Glu Thr Leu Asp Asp Ala
65                  70                  75                  80

Ala Gly Glu Ala Phe Asp Lys Thr Ala Lys Leu Leu Gly Leu Gly Tyr
                85                  90                  95

```
Pro Gly Gly Pro Glu Val Ser Arg Leu Ala Glu Ala Gly Thr Pro Gly
            100                 105                 110

Ala Val Val Leu Pro Arg Pro Met Leu His Ser Gly Asp Leu Asp Phe
        115                 120                 125

Ser Phe Ser Gly Leu Lys Thr Ala Val Leu Thr Gln Met Lys Lys Leu
    130                 135                 140

Glu Ala Ala His Ala Gly Gly Ala Val Leu Glu Arg Ala Lys Ala Asp
145                 150                 155                 160

Leu Ala Arg Gly Phe Val Asp Ala Ala Val Asp Val Leu Val Ala Lys
                165                 170                 175

Ser Leu Ala Ala Leu Lys Thr Thr Arg Leu Lys Arg Leu Val Val Ala
            180                 185                 190

Gly Gly Val Gly Ala Asn Arg Gln Leu Arg Ala Ala Leu Ser Ala Ala
        195                 200                 205

Ala Gln Lys Arg Gly Phe Asp Val His Tyr Pro Asp Leu Ala Leu Cys
    210                 215                 220

Thr Asp Asn Gly Ala Met Ile Ala Leu Ala Gly Ala Leu Arg Leu Thr
225                 230                 235                 240

Arg Trp Pro Ser Gln Ala Ser Arg Asp Tyr Ala Phe Thr Val Lys Pro
                245                 250                 255

Arg Trp Asp Leu Ala Ser Leu Ala Arg
            260                 265

<210> SEQ ID NO 117
<211> LENGTH: 341
<212> TYPE: PRT
<213> ORGANISM: Chlamydia trachomatis

<400> SEQUENCE: 117

Met Phe Ala Met Leu Thr Leu Gly Leu Glu Ser Ser Cys Asp Glu Thr
1               5                   10                  15

Ser Cys Ser Leu Val Gln Asn Gly Lys Ile Leu Ala Asn Lys Ile Ala
            20                  25                  30

Ser Gln Asp Ile His Ala Ser Tyr Gly Gly Val Ile Pro Glu Leu Ala
        35                  40                  45

Ser Arg Ala His Leu Gln Thr Phe Pro Glu Leu Leu Thr Ala Ala Thr
    50                  55                  60

Gln Ser Ala Gly Val Ser Leu Glu Asp Ile Glu Leu Ile Ser Val Ala
65                  70                  75                  80

Asn Thr Pro Gly Leu Ile Gly Ala Leu Ser Ile Gly Val Asn Phe Ala
                85                  90                  95

Lys Gly Leu Ala Ser Gly Leu Lys Arg Pro Leu Ile Gly Val Asn His
            100                 105                 110

Val Glu Ala His Leu Tyr Ala Ala Cys Met Glu Ala Pro Ala Thr Gln
        115                 120                 125

Phe Pro Ala Leu Gly Leu Ala Ile Ser Gly Ala His Thr Ser Leu Phe
    130                 135                 140

Leu Met Pro Asp Ala Thr Thr Phe Leu Leu Ile Gly Lys Thr Arg Asp
145                 150                 155                 160

Asp Ala Ile Gly Glu Thr Phe Asp Lys Val Ala Arg Phe Leu Gly Leu
                165                 170                 175

Pro Tyr Pro Gly Gly Gln Lys Leu Glu Glu Leu Ala Arg Glu Gly Asp
            180                 185                 190

Ala Asp Ala Phe Ala Phe Ser Pro Ala Arg Val Ser Gly Tyr Asp Phe
```

```
                195                 200                 205
Ser Phe Ser Gly Leu Lys Thr Ala Val Leu Tyr Ala Leu Lys Gly Asn
    210                 215                 220

Asn Ser Ser Ala Lys Ala Pro Phe Pro Glu Val Ser Glu Thr Gln Lys
225                 230                 235                 240

Arg Asn Ile Ala Ala Ser Phe Gln Lys Ala Val Phe Met Thr Ile Ala
                245                 250                 255

Gln Lys Leu Pro Asp Ile Val Lys Thr Phe Ser Cys Glu Ser Leu Ile
            260                 265                 270

Val Gly Gly Gly Val Ala Asn Asn Ser Tyr Phe Arg Arg Leu Leu Asn
        275                 280                 285

Gln Ile Cys Ser Leu Pro Ile Tyr Phe Pro Ser Ser Gln Leu Cys Ser
    290                 295                 300

Asp Asn Ala Ala Met Ile Ala Gly Leu Gly Glu Arg Leu Phe Cys Asn
305                 310                 315                 320

Arg Thr His Val Ser Lys Glu Val Ile Pro Cys Ala Arg Tyr Gln Trp
                325                 330                 335

Glu Ser Ala Cys Ser
            340

<210> SEQ ID NO 118
<211> LENGTH: 340
<212> TYPE: PRT
<213> ORGANISM: Clostridium botulinum

<400> SEQUENCE: 118

Met Lys Glu Ser Ile Asn Ile Leu Ala Ile Glu Ser Ser Cys Asp Glu
1               5                   10                  15

Thr Ser Ala Ala Val Val Val Asn Gly Arg Glu Val Leu Ser Asn Ile
            20                  25                  30

Ile Ala Ser Gln Ile Ser Thr His Glu Lys Phe Gly Gly Val Val Pro
        35                  40                  45

Glu Val Ala Ser Arg Lys His Ile Glu Val Ile Ser Ala Val Val Gln
    50                  55                  60

Glu Ala Leu Asp Glu Ala Asn Phe Thr Leu Asp Asp Ile Asp Ala Ile
65                  70                  75                  80

Gly Val Thr Tyr Gly Pro Gly Leu Val Gly Ala Leu Leu Val Gly Leu
                85                  90                  95

Gln Tyr Ala Lys Gly Leu Ala Phe Ala Thr Gly Lys Pro Leu Ile Gly
            100                 105                 110

Val Asn His Ile Glu Gly His Ile Ser Ala Asn Phe Ile Glu Tyr Lys
        115                 120                 125

Asp Leu Lys Pro Pro Phe Met Cys Leu Val Val Ser Gly Gly His Thr
    130                 135                 140

Phe Ile Val Tyr Met Lys Asp Tyr Gly Glu Phe Glu Val Leu Gly Glu
145                 150                 155                 160

Thr Arg Asp Asp Ala Ala Gly Glu Ala Phe Asp Lys Val Ala Arg Ala
                165                 170                 175

Ile Gly Leu Gly Tyr Pro Gly Gly Pro Lys Ile Asp Lys Ile Ser Lys
            180                 185                 190

Glu Gly Asn Glu Glu Ala Ile Lys Phe Pro Arg Ala Asn Phe His Asn
        195                 200                 205

Asp Thr Leu Asp Phe Ser Phe Ser Gly Ile Lys Ser Ala Val Leu Asn
    210                 215                 220
```

```
Tyr Leu Asn Lys Lys Glu Met Lys Gly Glu Glu Ile Asn Lys Ala Asp
225                 230                 235                 240

Val Ala Ala Ser Phe Gln Lys Ser Val Val Asp Val Leu Val Asp Asn
                245                 250                 255

Thr Ile Lys Ala Cys Met Ser Lys Lys Val Asp Lys Ile Ala Val Ala
            260                 265                 270

Gly Gly Val Ala Ser Asn Ser Cys Leu Arg Glu Thr Leu Val Arg Glu
        275                 280                 285

Cys Lys Lys Lys Gly Ile Glu Val Leu Ile Pro Pro Phe Ile Leu Cys
    290                 295                 300

Thr Asp Asn Ala Ala Met Ile Gly Ser Ala Ala Tyr Phe Glu Tyr Ile
305                 310                 315                 320

Lys Gly Arg Ser Thr Ser Leu Asp Ile Asn Ala Val Pro Asn Leu Lys
                325                 330                 335

Leu Gly Glu Arg
            340

<210> SEQ ID NO 119
<211> LENGTH: 338
<212> TYPE: PRT
<213> ORGANISM: Clostridium difficile

<400> SEQUENCE: 119

Met Ser Asp Ile Ile Thr Leu Ala Ile Glu Ser Ser Cys Asp Glu Thr
1               5                   10                  15

Ala Ala Ser Val Leu Lys Asn Gly Arg Glu Ile Leu Ser Asn Ile Ile
                20                  25                  30

Ser Thr Gln Ile Glu Thr His Lys Lys Phe Gly Gly Val Val Pro Glu
            35                  40                  45

Val Ala Ser Arg Lys His Val Glu Asn Ile Asp Ile Val Val Gln Glu
        50                  55                  60

Ala Leu Asp Lys Ala Asn Ile Gly Phe Asn Asp Ile Asp His Ile Ala
65                  70                  75                  80

Val Thr Tyr Gly Pro Gly Leu Val Gly Ala Leu Leu Val Gly Leu Ser
                85                  90                  95

Tyr Ala Lys Ala Leu Ala Tyr Thr Leu Asn Ile Pro Leu Val Gly Val
                100                 105                 110

Asn His Ile Glu Gly His Leu Ser Ala Asn Tyr Ile Glu His Lys Asp
            115                 120                 125

Leu Lys Pro Pro Phe Ile Thr Leu Ile Val Ser Gly Gly His Thr His
        130                 135                 140

Leu Val Glu Val Lys Asp Tyr Gly Lys Tyr Glu Ile Leu Gly Lys Thr
145                 150                 155                 160

Arg Asp Asp Ala Ser Gly Glu Ala Phe Asp Lys Ile Ser Arg Ala Met
                165                 170                 175

Asn Leu Gly Tyr Pro Gly Gly Pro Ile Ile Asp Asn Leu Ala Lys Asn
            180                 185                 190

Gly Asn Lys His Ala Ile Glu Phe Pro Arg Ala Tyr Leu Glu Glu Asp
        195                 200                 205

Ser Tyr Asp Phe Ser Phe Ser Gly Leu Lys Ser Val Leu Asn Tyr
            210                 215                 220

Leu Asn Gly Lys Arg Met Lys Asn Glu Glu Ile Val Val Glu Asp Val
225                 230                 235                 240

Ala Ala Ser Phe Gln Glu Ala Val Val Glu Val Leu Ser Thr Lys Ala
                245                 250                 255
```

-continued

```
Leu Lys Ala Val Lys Asp Lys Gly Tyr Asn Ile Ile Thr Leu Ser Gly
            260                 265                 270

Gly Val Ala Ser Asn Ser Gly Leu Arg Ala Lys Ile Thr Glu Leu Ala
        275                 280                 285

Lys Asp Asn Gly Ile Thr Val Lys Tyr Pro Pro Leu Ile Leu Cys Thr
290                 295                 300

Asp Asn Ala Ala Met Ile Gly Cys Ala Gly Tyr Tyr Asn Phe Ile Asn
305                 310                 315                 320

Gly Lys Thr His Asp Met Ser Leu Asn Ala Val Pro Asn Leu Lys Ile
                325                 330                 335

Asn Gln
```

<210> SEQ ID NO 120
<211> LENGTH: 348
<212> TYPE: PRT
<213> ORGANISM: Enterococcus faecalis

<400> SEQUENCE: 120

```
Met Thr Ile Phe Thr Lys Glu Arg Lys Leu Leu Leu Ala Val Glu Ser
1               5                   10                  15

Ser Cys Asp Glu Thr Ser Val Ala Val Ile Glu Asp Gly Asp Lys Ile
            20                  25                  30

Leu Ser Asn Ile Val Ala Ser Gln Ile Lys Ser His Gln Arg Phe Gly
        35                  40                  45

Gly Val Val Pro Glu Val Ala Ser Arg His His Val Glu Gln Val Thr
    50                  55                  60

Ile Cys Ile Glu Glu Ala Leu Thr Glu Ala Lys Val Thr Pro Glu Glu
65                  70                  75                  80

Leu Ser Gly Val Ala Val Thr Tyr Gly Pro Gly Leu Val Gly Ala Leu
                85                  90                  95

Leu Ile Gly Leu Ser Ala Ala Lys Ala Phe Ala Trp Ala His Gln Leu
            100                 105                 110

Pro Leu Ile Pro Val Asn His Met Ala Gly His Ile Tyr Ala Ala Arg
        115                 120                 125

Phe Val Ala Pro Leu Glu Phe Pro Leu Met Ala Leu Leu Val Ser Gly
    130                 135                 140

Gly His Thr Glu Leu Val Tyr Met Lys Glu Asp Gly Ser Phe Glu Ile
145                 150                 155                 160

Val Gly Glu Thr Arg Asp Asp Ala Ala Gly Glu Ala Tyr Asp Lys Val
                165                 170                 175

Gly Arg Val Leu Gly Leu Pro Tyr Pro Ser Gly Lys Glu Ile Asp Ala
            180                 185                 190

Leu Ala His Glu Gly Thr Asp Thr Tyr Gln Phe Pro Arg Ala Met Leu
        195                 200                 205

Lys Glu Asp Asn Tyr Asp Phe Ser Phe Ser Gly Leu Lys Ser Ala Phe
    210                 215                 220

Ile Asn Thr Val His Asn Ala Glu Gln Arg Gly Glu Ala Leu Ser Thr
225                 230                 235                 240

Lys Asp Leu Ala Ala Ser Phe Gln Ala Ser Val Val Glu Val Leu Val
                245                 250                 255

Thr Lys Thr Ile Arg Ala Cys Gln Glu Tyr Pro Val Lys Gln Leu Leu
            260                 265                 270

Ile Ala Gly Gly Val Ala Ala Asn Gln Gly Leu Arg Glu Ala Met Arg
        275                 280                 285
```

```
His Ala Ile Ser Glu Gln Leu Pro Glu Val Thr Leu Leu Ile Pro Pro
    290                 295                 300

Leu Lys Leu Cys Gly Asp Asn Ala Ala Met Ile Gly Ala Ala Ala Phe
305                 310                 315                 320

Ile Glu Ala Glu Lys Asn His Phe Ala Ser Tyr Asn Leu Asn Ala Glu
                325                 330                 335

Pro Gly Val Ser Phe Met Thr Ile Ser Glu Glu Gly
            340                 345

<210> SEQ ID NO 121
<211> LENGTH: 50
<212> TYPE: PRT
<213> ORGANISM: artificial sequence
<220> FEATURE:
<223> OTHER INFORMATION: polypeptide or immunogenic fragment of
      Enetrococcus spp genes

<400> SEQUENCE: 121

Leu Ile Gly Leu Ser Ala Ala Lys Ala Phe Ala Trp Ala His Gln Leu
1               5                   10                  15

Pro Leu Ile Pro Val Asn His Met Ala Gly His Ile Tyr Ala Ala Arg
            20                  25                  30

Phe Val Ala Pro Leu Glu Phe Pro Leu Met Ala Leu Leu Val Ser Gly
        35                  40                  45

Gly His
    50

<210> SEQ ID NO 122
<211> LENGTH: 337
<212> TYPE: PRT
<213> ORGANISM: Escherichia coli

<400> SEQUENCE: 122

Met Arg Val Leu Gly Ile Glu Thr Ser Cys Asp Glu Thr Gly Ile Ala
1               5                   10                  15

Ile Tyr Asp Asp Glu Lys Gly Leu Leu Ala Asn Gln Leu Tyr Ser Gln
            20                  25                  30

Val Lys Leu His Ala Asp Tyr Gly Gly Val Val Pro Glu Leu Ala Ser
        35                  40                  45

Arg Asp His Val Arg Lys Thr Val Pro Leu Ile Gln Ala Ala Leu Lys
    50                  55                  60

Glu Ser Gly Leu Thr Ala Lys Asp Ile Asp Ala Val Ala Tyr Thr Ala
65                  70                  75                  80

Gly Pro Gly Leu Val Gly Ala Leu Leu Val Gly Ala Thr Val Gly Arg
                85                  90                  95

Ser Leu Ala Phe Ala Trp Asp Val Pro Ala Ile Pro Val His His Met
            100                 105                 110

Glu Gly His Leu Leu Ala Pro Met Leu Glu Asp Asn Pro Pro Glu Phe
        115                 120                 125

Pro Phe Val Ala Leu Leu Val Ser Gly Gly His Thr Gln Leu Ile Ser
    130                 135                 140

Val Thr Gly Ile Gly Gln Tyr Glu Leu Leu Gly Glu Ser Ile Asp Asp
145                 150                 155                 160

Ala Ala Gly Glu Ala Phe Asp Lys Thr Ala Lys Leu Leu Gly Leu Asp
                165                 170                 175

Tyr Pro Gly Gly Pro Leu Leu Ser Lys Met Ala Ala Gln Gly Thr Ala
            180                 185                 190
```

-continued

Gly Arg Phe Val Phe Pro Arg Pro Met Thr Asp Arg Pro Gly Leu Asp
            195                 200                 205

Phe Ser Phe Ser Gly Leu Lys Thr Phe Ala Ala Asn Thr Ile Arg Asp
        210                 215                 220

Asn Gly Thr Asp Asp Gln Thr Arg Ala Asp Ile Ala Arg Ala Phe Glu
225                 230                 235                 240

Asp Ala Val Val Asp Thr Leu Met Ile Lys Cys Lys Arg Ala Leu Asp
                245                 250                 255

Gln Thr Gly Phe Lys Arg Leu Val Met Ala Gly Val Ser Ala Asn
            260                 265                 270

Arg Thr Leu Arg Ala Lys Leu Ala Glu Met Met Lys Lys Arg Arg Gly
            275                 280                 285

Glu Val Phe Tyr Ala Arg Pro Glu Phe Cys Thr Asp Asn Gly Ala Met
            290                 295                 300

Ile Ala Tyr Ala Gly Met Val Arg Phe Lys Ala Gly Ala Thr Ala Asp
305                 310                 315                 320

Leu Gly Val Ser Val Arg Pro Arg Trp Pro Leu Ala Glu Leu Pro Ala
                325                 330                 335

Ala

<210> SEQ ID NO 123
<211> LENGTH: 246
<212> TYPE: PRT
<213> ORGANISM: artificial sequence
<220> FEATURE:
<223> OTHER INFORMATION: polypeptide or immunogenic fragment of
      Escherichia spp genes

<400> SEQUENCE: 123

Ala Thr Val Gly Arg Ser Leu Ala Phe Ala Trp Asp Val Pro Ala Ile
1               5                   10                  15

Pro Val His His Met Glu Gly His Leu Leu Ala Pro Met Leu Glu Asp
            20                  25                  30

Asn Pro Pro Glu Phe Pro Phe Val Ala Leu Leu Val Ser Gly Gly His
        35                  40                  45

Thr Gln Leu Ile Ser Val Thr Gly Ile Gly Gln Tyr Glu Leu Leu Gly
    50                  55                  60

Glu Ser Ile Asp Asp Ala Ala Gly Glu Ala Phe Asp Lys Thr Ala Lys
65                  70                  75                  80

Leu Leu Gly Leu Asp Tyr Pro Gly Gly Pro Leu Leu Ser Lys Met Ala
                85                  90                  95

Ala Gln Gly Thr Ala Gly Arg Phe Val Phe Pro Arg Pro Met Thr Asp
            100                 105                 110

Arg Pro Gly Leu Asp Phe Ser Phe Ser Gly Leu Lys Thr Phe Ala Ala
            115                 120                 125

Asn Thr Ile Arg Asp Asn Gly Thr Asp Asp Gln Thr Arg Ala Asp Ile
        130                 135                 140

Ala Arg Ala Phe Glu Asp Ala Val Val Asp Thr Leu Met Ile Lys Cys
145                 150                 155                 160

Lys Arg Ala Leu Asp Gln Thr Gly Phe Lys Arg Leu Val Met Ala Gly
                165                 170                 175

Gly Val Ser Ala Asn Arg Thr Leu Arg Ala Lys Leu Ala Glu Met Met
            180                 185                 190

Lys Lys Arg Arg Gly Glu Val Phe Tyr Ala Arg Pro Glu Phe Cys Thr
            195                 200                 205

```
Asp Asn Gly Ala Met Ile Ala Tyr Ala Gly Met Val Arg Phe Lys Ala
            210                 215                 220

Gly Ala Thr Ala Asp Leu Gly Val Ser Val Arg Pro Arg Trp Pro Leu
225                 230                 235                 240

Ala Glu Leu Pro Ala Ala
                245

<210> SEQ ID NO 124
<211> LENGTH: 342
<212> TYPE: PRT
<213> ORGANISM: Haemophilus influenzae

<400> SEQUENCE: 124

Met Lys Ile Leu Gly Ile Glu Thr Ser Cys Asp Glu Thr Gly Val Ala
1               5                   10                  15

Ile Tyr Asp Glu Glu Lys Gly Leu Ile Ala Asn Gln Leu Tyr Thr Gln
                20                  25                  30

Ile Ala Leu His Ala Asp Tyr Gly Gly Val Pro Glu Leu Ala Ser
            35                  40                  45

Arg Asp His Ile Arg Lys Thr Ala Pro Leu Ile Lys Ala Ala Leu Glu
50                  55                  60

Glu Ala Lys Ile Thr Ala Ser Asp Ile Asp Gly Ile Ala Tyr Thr Ser
65                  70                  75                  80

Gly Pro Gly Leu Val Gly Ala Leu Leu Val Gly Ala Thr Ile Ala Arg
                85                  90                  95

Ser Leu Ala Tyr Ala Trp Asn Val Pro Ala Ile Gly Val His His Met
            100                 105                 110

Glu Gly His Leu Leu Ala Pro Met Leu Asp Lys Asn Ser Pro His Phe
        115                 120                 125

Pro Phe Val Ala Leu Leu Val Ser Gly Gly His Thr Gln Leu Val Arg
130                 135                 140

Val Asp Gly Val Gly Lys Tyr Glu Val Ile Gly Glu Ser Ile Asp Asp
145                 150                 155                 160

Ala Ala Gly Glu Ala Phe Asp Lys Thr Ala Lys Leu Leu Gly Leu Asp
                165                 170                 175

Tyr Pro Gly Gly Ala Ala Leu Ser Arg Leu Ala Glu Lys Gly Ala Pro
            180                 185                 190

Asn Arg Phe Thr Phe Pro Arg Pro Met Thr Asp Arg Ala Gly Leu Asp
        195                 200                 205

Phe Ser Phe Ser Gly Leu Lys Thr Phe Ala Ala Asn Thr Ile Asn Gln
210                 215                 220

Ala Ile Lys Asn Glu Gly Lys Leu Thr Glu Gln Ile Lys Ala Asp Ile
225                 230                 235                 240

Ala Tyr Ala Phe Gln Asp Ala Val Val Asp Thr Leu Ala Ile Lys Cys
                245                 250                 255

Lys Arg Ala Leu Lys Glu Thr Gly Tyr Lys Arg Leu Val Ile Ala Gly
            260                 265                 270

Gly Val Ser Ala Asn Lys Lys Leu Arg Glu Ser Leu Ala His Leu Met
        275                 280                 285

Gln Asn Leu Gly Gly Glu Val Phe Tyr Pro Gln Pro Gln Phe Cys Thr
290                 295                 300

Asp Asn Gly Ala Met Ile Ala Tyr Thr Gly Phe Leu Arg Leu Lys Gln
305                 310                 315                 320

Gly Gln His Ser Asp Leu Ala Ile Asp Val Lys Pro Arg Trp Ala Met
```

Thr Glu Leu Glu Ala Ile
        340

<210> SEQ ID NO 125
<211> LENGTH: 249
<212> TYPE: PRT
<213> ORGANISM: artificial sequence
<220> FEATURE:
<223> OTHER INFORMATION: polypeptide or immunogenic fragment of
      Haemophilus spp genes

<400> SEQUENCE: 125

Ile Ala Arg Ser Leu Ala Tyr Ala Trp Asn Val Pro Ala Ile Gly Val
1               5                   10                  15

His His Met Glu Gly His Leu Leu Ala Pro Met Leu Asp Lys Asn Ser
            20                  25                  30

Pro His Phe Pro Phe Val Ala Leu Leu Val Ser Gly Gly His Thr Gln
        35                  40                  45

Leu Val Arg Val Asp Gly Val Gly Lys Tyr Glu Val Ile Gly Glu Ser
    50                  55                  60

Ile Asp Asp Ala Ala Gly Glu Ala Phe Asp Lys Thr Ala Lys Leu Leu
65                  70                  75                  80

Gly Leu Asp Tyr Pro Gly Gly Ala Ala Leu Ser Arg Leu Ala Glu Lys
                85                  90                  95

Gly Ala Pro Asn Arg Phe Thr Phe Pro Arg Pro Met Thr Asp Arg Ala
            100                 105                 110

Gly Leu Asp Phe Ser Phe Ser Gly Leu Lys Thr Phe Ala Ala Asn Thr
        115                 120                 125

Ile Asn Gln Ala Ile Lys Asn Glu Gly Lys Leu Thr Glu Gln Ile Lys
    130                 135                 140

Ala Asp Ile Ala Tyr Ala Phe Gln Asp Ala Val Val Asp Thr Leu Ala
145                 150                 155                 160

Ile Lys Cys Lys Arg Ala Leu Lys Glu Thr Gly Tyr Lys Arg Leu Val
                165                 170                 175

Ile Ala Gly Gly Val Ser Ala Asn Lys Lys Leu Arg Glu Ser Leu Ala
            180                 185                 190

His Leu Met Gln Asn Leu Gly Gly Glu Val Phe Tyr Pro Gln Pro Gln
        195                 200                 205

Phe Cys Thr Asp Asn Gly Ala Met Ile Ala Tyr Thr Gly Phe Leu Arg
    210                 215                 220

Leu Lys Gln Gly Gln His Ser Asp Leu Ala Ile Asp Val Lys Pro Arg
225                 230                 235                 240

Trp Ala Met Thr Glu Leu Glu Ala Ile
                245

<210> SEQ ID NO 126
<211> LENGTH: 340
<212> TYPE: PRT
<213> ORGANISM: Helicobacter pylori

<400> SEQUENCE: 126

Met Ile Leu Ser Ile Glu Ser Ser Cys Asp Asp Ser Ser Leu Ala Leu
1               5                   10                  15

Thr Arg Ile Lys Asp Ala Lys Leu Ile Ala His Phe Lys Ile Ser Gln
            20                  25                  30

Glu Lys His His Ser Ser Tyr Gly Gly Val Val Pro Glu Leu Ala Ser

```
                35                  40                  45
Arg Leu His Ala Glu Asn Leu Pro Leu Leu Glu Arg Ile Lys Ile
 50                  55                  60
Ser Leu Asn Lys Asp Phe Ser Lys Leu Lys Ala Ile Ala Ile Thr Asn
 65                  70                  75                  80
Gln Pro Gly Leu Ser Val Thr Leu Ile Glu Gly Leu Met Met Ala Lys
                 85                  90                  95
Ala Leu Ser Leu Ser Leu Asn Leu Pro Leu Ile Leu Glu Asp His Leu
                100                 105                 110
Arg Gly His Val Tyr Ser Leu Phe Ile Asn Glu Lys Gln Thr Cys Met
                115                 120                 125
Pro Leu Ser Ala Leu Leu Val Ser Gly Gly His Ser Leu Ile Leu Glu
130                 135                 140
Ala Arg Asp Tyr Glu Asp Ile Lys Ile Val Ala Thr Ser Leu Asp Asp
145                 150                 155                 160
Ser Phe Gly Glu Ser Phe Asp Lys Val Ser Lys Met Leu Asp Leu Gly
                165                 170                 175
Tyr Pro Gly Gly Pro Ile Val Glu Lys Leu Ala Leu Asp Tyr Ala His
                180                 185                 190
Gln Asn Glu Pro Leu Met Phe Pro Val Pro Leu Lys Asn Ser Gln Asn
                195                 200                 205
Leu Ala Phe Ser Phe Ser Gly Leu Lys Asn Ala Val Arg Leu Glu Val
210                 215                 220
Glu Lys Asn Ala Pro Asn Leu Asn Glu Ala Ile Lys Gln Lys Ile Ser
225                 230                 235                 240
Tyr His Phe Gln Ser Ala Ala Ile Glu His Leu Ile Gln Gln Thr Lys
                245                 250                 255
Arg Tyr Phe Lys Ile Lys Arg Pro Lys Ile Phe Gly Ile Val Gly Gly
                260                 265                 270
Ala Ser Gln Asn Leu Ala Leu Arg Lys Ala Phe Glu Asn Leu Cys Asp
                275                 280                 285
Glu Phe Asp Cys Lys Leu Val Leu Ala Pro Leu Glu Phe Cys Ser Asp
290                 295                 300
Asn Ala Ala Met Ile Gly Arg Ser Ser Leu Glu Ala Tyr Gln Gln Lys
305                 310                 315                 320
Arg Phe Val Ser Leu Glu Lys Ala Asn Ile Ser Pro Arg Thr Leu Leu
                325                 330                 335
Lys Ser Phe Glu
            340

<210> SEQ ID NO 127
<211> LENGTH: 344
<212> TYPE: PRT
<213> ORGANISM: Mycobacterium tuberculosis

<400> SEQUENCE: 127

Met Thr Thr Val Leu Gly Ile Glu Thr Ser Cys Asp Glu Thr Gly Val
 1               5                  10                  15
Gly Ile Ala Arg Leu Asp Pro Asp Gly Thr Val Thr Leu Leu Ala Asp
                20                  25                  30
Glu Val Ala Ser Ser Val Asp Glu His Val Arg Phe Gly Gly Val Val
                35                  40                  45
Pro Glu Ile Ala Ser Arg Ala His Leu Glu Ala Leu Gly Pro Ala Met
 50                  55                  60
```

Arg Arg Ala Leu Ala Ala Gly Leu Lys Gln Pro Asp Ile Val Ala
65                  70                  75                  80

Ala Thr Ile Gly Pro Gly Leu Ala Gly Ala Leu Leu Val Gly Val Ala
                85                  90                  95

Ala Ala Lys Ala Tyr Ser Ala Ala Trp Gly Val Pro Phe Tyr Ala Val
            100                 105                 110

Asn His Leu Gly Gly His Leu Ala Ala Asp Val Tyr Glu His Gly Pro
            115                 120                 125

Leu Pro Glu Cys Val Ala Leu Val Ser Gly Gly His Thr His Leu
130                 135                 140

Leu His Val Arg Ser Leu Gly Glu Pro Ile Ile Glu Leu Gly Ser Thr
145                 150                 155                 160

Val Asp Asp Ala Ala Gly Glu Ala Tyr Asp Lys Val Ala Arg Leu Leu
                165                 170                 175

Gly Leu Gly Tyr Pro Gly Gly Lys Ala Leu Asp Asp Leu Ala Arg Thr
            180                 185                 190

Gly Asp Arg Asp Ala Ile Val Phe Pro Arg Gly Met Ser Gly Pro Ala
            195                 200                 205

Asp Asp Arg Tyr Ala Phe Ser Phe Ser Gly Leu Lys Thr Ala Val Ala
210                 215                 220

Arg Tyr Val Glu Ser His Ala Ala Asp Pro Gly Phe Arg Thr Ala Asp
225                 230                 235                 240

Ile Ala Ala Gly Phe Gln Glu Ala Val Ala Asp Val Leu Thr Met Lys
                245                 250                 255

Ala Val Arg Ala Ala Thr Ala Leu Gly Val Ser Thr Leu Leu Ile Ala
            260                 265                 270

Gly Gly Val Ala Ala Asn Ser Arg Leu Arg Glu Leu Ala Thr Gln Arg
            275                 280                 285

Cys Gly Glu Ala Gly Arg Thr Leu Arg Ile Pro Ser Pro Arg Leu Cys
290                 295                 300

Thr Asp Asn Gly Ala Met Ile Ala Ala Phe Ala Ala Gln Leu Val Ala
305                 310                 315                 320

Ala Gly Ala Pro Pro Ser Pro Leu Asp Val Pro Ser Asp Pro Gly Leu
                325                 330                 335

Pro Val Met Gln Gly Gln Val Arg
            340

<210> SEQ ID NO 128
<211> LENGTH: 166
<212> TYPE: PRT
<213> ORGANISM: artificial sequence
<220> FEATURE:
<223> OTHER INFORMATION: polypeptide or immunogenic fragment of
      Myobacterium spp genes

<400> SEQUENCE: 128

Ala Ala Ala Lys Ala Tyr Ser Ala Ala Trp Gly Val Pro Phe Tyr Ala
1               5                   10                  15

Val Asn His Leu Gly Gly His Leu Ala Ala Asp Val Tyr Glu His Gly
            20                  25                  30

Pro Leu Pro Glu Cys Val Ala Leu Val Ser Gly Gly His Thr His
            35                  40                  45

Leu Leu His Val Arg Ser Leu Gly Glu Pro Ile Ile Glu Leu Gly Ser
50                  55                  60

Thr Val Asp Asp Ala Ala Gly Glu Ala Tyr Asp Lys Val Ala Arg Leu
65                  70                  75                  80

-continued

Leu Gly Leu Gly Tyr Pro Gly Gly Lys Ala Leu Asp Leu Ala Arg
                85                  90                  95

Thr Gly Asp Arg Asp Ala Ile Val Phe Pro Arg Gly Met Ser Gly Pro
            100                 105                 110

Ala Asp Asp Arg Tyr Ala Phe Ser Phe Ser Gly Leu Lys Thr Ala Val
        115                 120                 125

Ala Arg Tyr Val Glu Ser His Ala Ala Asp Pro Gly Phe Arg Thr Ala
    130                 135                 140

Asp Ile Ala Ala Gly Phe Gln Glu Ala Val Ala Asp Val Leu Thr Met
145                 150                 155                 160

Lys Ala Val Arg Ala Ala
                165

<210> SEQ ID NO 129
<211> LENGTH: 24
<212> TYPE: PRT
<213> ORGANISM: artificial sequence
<220> FEATURE:
<223> OTHER INFORMATION: polypeptide ot immunogenic fragment of a
      Mycobacterium spp gene

<400> SEQUENCE: 129

Ala Gly Ala Pro Pro Ser Pro Leu Asp Val Pro Ser Asp Pro Gly Leu
1               5                   10                  15

Pro Val Met Gln Gly Gln Val Arg
            20

<210> SEQ ID NO 130
<211> LENGTH: 354
<212> TYPE: PRT
<213> ORGANISM: Neisseria gonorrhoeae

<400> SEQUENCE: 130

Met Leu Val Leu Gly Ile Glu Ser Ser Cys Asp Glu Thr Gly Val Ala
1               5                   10                  15

Leu Tyr Asp Thr Glu Arg Gly Leu Arg Ser His Cys Leu His Thr Gln
            20                  25                  30

Met Ala Met His Ala Glu Tyr Gly Gly Val Val Pro Glu Leu Ala Ser
        35                  40                  45

Arg Asp His Ile Arg Arg Leu Val Pro Leu Thr Glu Gly Cys Leu Ala
    50                  55                  60

Gln Ala Gly Ala Ser Tyr Gly Asp Ile Asp Ala Val Ala Phe Thr Gln
65                  70                  75                  80

Gly Pro Gly Leu Gly Gly Ala Leu Leu Ala Gly Ser Ser Tyr Ala Asn
                85                  90                  95

Ala Leu Ala Leu Ala Leu Asp Lys Pro Val Ile Pro Val His His Leu
            100                 105                 110

Glu Gly His Leu Leu Ser Pro Leu Leu Ala Glu Lys Pro Asp Phe
        115                 120                 125

Pro Phe Val Ala Leu Leu Val Ser Gly Gly His Thr Gln Ile Met Ala
    130                 135                 140

Val Arg Asp Ile Gly Asp Tyr Glu Leu Leu Gly Glu Ser Val Asp Asp
145                 150                 155                 160

Ala Ala Gly Glu Ala Phe Asp Lys Thr Ala Lys Leu Leu Gly Leu Pro
                165                 170                 175

Tyr Pro Gly Gly Ala Lys Leu Ser Glu Leu Ala Glu Ser Gly Arg Pro
            180                 185                 190

Glu Ala Phe Val Phe Pro Arg Pro Met Ile His Ser Asp Asp Leu Gln
            195                 200                 205

Met Ser Phe Ser Gly Leu Lys Thr Ala Val Leu Thr Ala Val Glu Lys
        210                 215                 220

Val Arg Glu Ala Asn Gly Ser Glu Thr Ile Pro Glu Gln Thr Arg Asn
225                 230                 235                 240

Asn Ile Cys Arg Ala Phe Gln Asp Ala Val Glu Val Leu Glu Ala
                245                 250                 255

Lys Val Lys Lys Ala Leu Leu Gln Thr Gly Phe Arg Thr Val Val Val
                260                 265                 270

Ala Gly Gly Val Gly Ala Asn Arg Lys Leu Arg Glu Thr Phe Gly Asn
            275                 280                 285

Met Thr Val Gln Ile Pro Thr Pro Lys Gly Lys Pro Lys His Pro Ser
        290                 295                 300

Glu Lys Val Ser Val Phe Phe Pro Pro Met Ala Tyr Cys Thr Asp Asn
305                 310                 315                 320

Gly Ala Met Ile Ala Phe Ala Gly Ala Met His Leu Gly Lys Gly Arg
                325                 330                 335

Glu Val Gly Ala Phe Asn Val Arg Pro Arg Trp Ser Leu Ser Glu Ile
            340                 345                 350

Val Lys

<210> SEQ ID NO 131
<211> LENGTH: 354
<212> TYPE: PRT
<213> ORGANISM: Neisseria meningitidis

<400> SEQUENCE: 131

Met Leu Val Leu Gly Ile Glu Ser Ser Cys Asp Glu Thr Gly Val Ala
1               5                   10                  15

Leu Tyr Asp Thr Glu Arg Gly Leu Arg Ala His Cys Leu His Thr Gln
            20                  25                  30

Met Ala Met His Ala Glu Tyr Gly Gly Val Val Pro Glu Leu Ala Ser
        35                  40                  45

Arg Asp His Ile Arg Arg Leu Val Pro Leu Thr Glu Gly Cys Leu Ala
50                  55                  60

Gln Ala Gly Ala Ser Tyr Gly Asp Ile Asp Ala Val Ala Phe Thr Gln
65                  70                  75                  80

Gly Pro Gly Leu Gly Gly Ala Leu Leu Ala Gly Ser Ser Tyr Ala Asn
                85                  90                  95

Ala Leu Ala Phe Ala Leu Asp Lys Pro Val Ile Pro Val His His Leu
            100                 105                 110

Glu Gly His Leu Leu Ser Pro Leu Leu Ala Glu Lys Pro Asp Phe
        115                 120                 125

Pro Phe Val Ala Leu Leu Val Ser Gly Gly His Thr Gln Ile Met Ala
        130                 135                 140

Val Lys Gly Ile Gly Asp Tyr Glu Leu Leu Gly Glu Ser Val Asp Asp
145                 150                 155                 160

Ala Ala Gly Glu Ala Phe Asp Lys Thr Ala Lys Leu Leu Gly Leu Pro
                165                 170                 175

Tyr Pro Gly Gly Ala Lys Leu Ser Glu Leu Ala Glu Ser Gly Arg Pro
            180                 185                 190

Glu Ala Phe Val Phe Pro Arg Pro Met Ile His Ser Asp Asp Leu Gln
            195                 200                 205

```
Met Ser Phe Ser Gly Leu Lys Thr Ala Val Leu Thr Ala Val Glu Lys
    210                 215                 220

Val Arg Ala Glu Asn Gly Ala Asp Asp Ile Pro Glu Gln Thr Arg Asn
225                 230                 235                 240

Asp Ile Cys Arg Ala Phe Gln Asp Ala Val Val Asp Val Leu Glu Ala
                245                 250                 255

Lys Val Lys Lys Ala Leu Leu Gln Thr Gly Phe Arg Thr Val Val
                260                 265                 270

Ala Gly Gly Val Gly Ala Asn Arg Lys Leu Arg Glu Thr Phe Gly Asn
                275                 280                 285

Met Thr Val Gln Ile Pro Thr Pro Lys Gly Lys Pro Lys His Pro Ser
    290                 295                 300

Glu Lys Val Ser Val Phe Phe Pro Pro Thr Ala Tyr Cys Thr Asp Asn
305                 310                 315                 320

Gly Ala Met Ile Ala Phe Ala Gly Ala Met His Leu Gly Lys Gly Arg
                325                 330                 335

Glu Val Gly Ala Phe Asn Val Arg Pro Arg Trp Pro Leu Ser Glu Ile
                340                 345                 350

Val Lys
```

<210> SEQ ID NO 132
<211> LENGTH: 341
<212> TYPE: PRT
<213> ORGANISM: Pseudomonas aeruginosa

<400> SEQUENCE: 132

```
Met Arg Val Leu Gly Leu Glu Thr Ser Cys Asp Glu Thr Gly Val Ala
1               5                   10                  15

Leu Tyr Asp Ser Glu Arg Gly Leu Leu Ala Asp Ala Leu Phe Ser Gln
                20                  25                  30

Ile Asp Leu His Arg Val Tyr Gly Gly Val Val Pro Glu Leu Ala Ser
                35                  40                  45

Arg Asp His Val Lys Arg Met Leu Pro Leu Ile Arg Gln Val Leu Asp
            50                  55                  60

Glu Ser Gly Cys Thr Pro Ala Asp Ile Asp Ala Ile Ala Tyr Thr Ala
65                  70                  75                  80

Gly Pro Gly Leu Val Gly Ala Leu Leu Val Gly Ala Ser Cys Ala Gln
                85                  90                  95

Ala Met Ala Phe Ala Trp Gly Val Pro Ala Val Gly Val His His Met
                100                 105                 110

Glu Gly His Leu Leu Ala Pro Met Leu Glu Glu Gln Pro Pro Arg Phe
            115                 120                 125

Pro Phe Val Ala Leu Leu Val Ser Gly Gly His Thr Gln Leu Val Arg
    130                 135                 140

Val Asp Gly Ile Gly Arg Tyr Gln Leu Leu Gly Glu Ser Val Asp Asp
145                 150                 155                 160

Ala Ala Gly Glu Ala Phe Asp Lys Thr Ala Lys Leu Ile Gly Leu Gly
                165                 170                 175

Tyr Pro Gly Gly Pro Glu Ile Ala Arg Leu Ala Glu Arg Gly Thr Pro
                180                 185                 190

Gly Arg Phe Val Phe Pro Arg Pro Met Thr Asp Arg Pro Gly Leu Asp
            195                 200                 205

Phe Ser Phe Ser Gly Leu Lys Thr Phe Thr Leu Asn Thr Trp Gln Arg
    210                 215                 220
```

```
Cys Val Glu Ala Gly Asp Asp Ser Glu Gln Thr Arg Cys Asp Ile Ala
225                 230                 235                 240

Leu Ala Phe Gln Thr Ala Val Val Glu Thr Leu Leu Ile Lys Cys Arg
            245                 250                 255

Arg Ala Leu Lys Gln Thr Gly Leu Lys Asn Leu Val Ile Ala Gly Gly
            260                 265                 270

Val Ser Ala Asn Gln Ala Leu Arg Ser Gly Leu Glu Lys Met Leu Gly
        275                 280                 285

Glu Met Lys Gly Gln Val Phe Tyr Ala Arg Pro Arg Phe Cys Thr Asp
        290                 295                 300

Asn Gly Ala Met Ile Ala Tyr Ala Gly Cys Gln Arg Leu Leu Ala Gly
305                 310                 315                 320

Gln His Asp Gly Pro Ala Ile Ser Val Gln Pro Arg Trp Pro Met Glu
            325                 330                 335

Ser Leu Pro Ala Val
            340

<210> SEQ ID NO 133
<211> LENGTH: 242
<212> TYPE: PRT
<213> ORGANISM: artificial sequence
<220> FEATURE:
<223> OTHER INFORMATION: polypeptide or immunogenic fragment of
      Pseudomonas spp genes

<400> SEQUENCE: 133

Phe Ala Trp Gly Val Pro Ala Val Gly Val His His Met Glu Gly His
1               5                   10                  15

Leu Leu Ala Pro Met Leu Glu Glu Gln Pro Pro Arg Phe Pro Phe Val
            20                  25                  30

Ala Leu Leu Val Ser Gly Gly His Thr Gln Leu Val Arg Val Asp Gly
        35                  40                  45

Ile Gly Arg Tyr Gln Leu Leu Gly Glu Ser Val Asp Asp Ala Ala Gly
    50                  55                  60

Glu Ala Phe Asp Lys Thr Ala Lys Leu Ile Gly Leu Gly Tyr Pro Gly
65                  70                  75                  80

Gly Pro Glu Ile Ala Arg Leu Ala Glu Arg Gly Thr Pro Gly Arg Phe
                85                  90                  95

Val Phe Pro Arg Pro Met Thr Asp Arg Pro Gly Leu Asp Phe Ser Phe
            100                 105                 110

Ser Gly Leu Lys Thr Phe Thr Leu Asn Thr Trp Gln Arg Cys Val Glu
        115                 120                 125

Ala Gly Asp Asp Ser Glu Gln Thr Arg Cys Asp Ile Ala Leu Ala Phe
    130                 135                 140

Gln Thr Ala Val Val Glu Thr Leu Leu Ile Lys Cys Arg Arg Ala Leu
145                 150                 155                 160

Lys Gln Thr Gly Leu Lys Asn Leu Val Ile Ala Gly Gly Val Ser Ala
                165                 170                 175

Asn Gln Ala Leu Arg Ser Gly Leu Glu Lys Met Leu Gly Glu Met Lys
            180                 185                 190

Gly Gln Val Phe Tyr Ala Arg Pro Arg Phe Cys Thr Asp Asn Gly Ala
        195                 200                 205

Met Ile Ala Tyr Ala Gly Cys Gln Arg Leu Leu Ala Gly Gln His Asp
    210                 215                 220

Gly Pro Ala Ile Ser Val Gln Pro Arg Trp Pro Met Glu Ser Leu Pro
```

<210> SEQ ID NO 134
<211> LENGTH: 337
<212> TYPE: PRT
<213> ORGANISM: Shigella flexneri

<400> SEQUENCE: 134

```
Met Arg Val Leu Gly Ile Glu Thr Ser Cys Asp Glu Thr Gly Ile Ala
1               5                   10                  15
Ile Tyr Asp Asp Glu Lys Gly Leu Leu Ala Asn Gln Leu Tyr Ser Gln
            20                  25                  30
Val Lys Leu His Ala Asp Tyr Gly Gly Val Val Pro Glu Leu Ala Ser
        35                  40                  45
Arg Asp His Val Arg Lys Thr Val Pro Leu Ile Gln Ala Ala Leu Lys
    50                  55                  60
Glu Ser Gly Leu Thr Ala Lys Asp Ile Asp Ala Val Ala Tyr Thr Ala
65                  70                  75                  80
Gly Pro Gly Leu Val Gly Ala Leu Leu Val Gly Ala Thr Val Gly Arg
                85                  90                  95
Ser Leu Ala Phe Ala Trp Asn Val Pro Ala Ile Pro Val His His Met
            100                 105                 110
Glu Gly His Leu Leu Ala Pro Met Leu Glu Asp Asn Pro Pro Glu Phe
        115                 120                 125
Pro Phe Val Ala Leu Leu Val Ser Gly Gly His Thr Gln Leu Ile Ser
    130                 135                 140
Val Thr Gly Ile Gly Gln Tyr Glu Leu Leu Gly Glu Ser Ile Asp Asp
145                 150                 155                 160
Ala Ala Gly Glu Ala Phe Asp Lys Thr Ala Lys Leu Leu Gly Leu Asp
                165                 170                 175
Tyr Pro Gly Gly Pro Leu Leu Ser Lys Met Ala Ala Gln Gly Thr Ala
            180                 185                 190
Gly Arg Phe Val Phe Pro Arg Pro Met Thr Asp Arg Pro Gly Leu Asp
        195                 200                 205
Phe Ser Phe Ser Gly Leu Lys Thr Phe Ala Ala Asn Thr Ile Arg Asp
    210                 215                 220
Asn Gly Thr Asp Asp Gln Thr Arg Ala Asp Ile Ala Arg Ala Phe Glu
225                 230                 235                 240
Asp Ala Val Val Asp Thr Leu Met Ile Lys Cys Lys Arg Ala Leu Asp
                245                 250                 255
Gln Thr Gly Phe Lys Arg Leu Val Met Ala Gly Gly Val Ser Ala Asn
            260                 265                 270
Arg Thr Leu Arg Ala Lys Leu Ala Glu Met Met Lys Lys Arg Arg Gly
        275                 280                 285
Glu Val Phe Tyr Ala Arg Pro Glu Phe Cys Thr Asp Asn Gly Ala Met
    290                 295                 300
Ile Ala Tyr Ala Gly Met Val Arg Phe Lys Ala Gly Ala Thr Ala Asp
305                 310                 315                 320
Leu Gly Val Ser Val Arg Pro Arg Trp Pro Leu Ala Glu Leu Pro Ala
                325                 330                 335
Ala
```

<210> SEQ ID NO 135

```
<211> LENGTH: 244
<212> TYPE: PRT
<213> ORGANISM: artificial sequence
<220> FEATURE:
<223> OTHER INFORMATION: polypeptide or immunogenic fragment of Shigella
      spp genes

<400> SEQUENCE: 135

Val Gly Arg Ser Leu Ala Phe Ala Trp Asn Val Pro Ala Ile Pro Val
1               5                   10                  15

His His Met Glu Gly His Leu Leu Ala Pro Met Leu Glu Asp Asn Pro
            20                  25                  30

Pro Glu Phe Pro Phe Val Ala Leu Leu Val Ser Gly Gly His Thr Gln
        35                  40                  45

Leu Ile Ser Val Thr Gly Ile Gly Gln Tyr Glu Leu Leu Gly Glu Ser
    50                  55                  60

Ile Asp Asp Ala Ala Gly Glu Ala Phe Asp Lys Thr Ala Lys Leu Leu
65                  70                  75                  80

Gly Leu Asp Tyr Pro Gly Gly Pro Leu Leu Ser Lys Met Ala Ala Gln
                85                  90                  95

Gly Thr Ala Gly Arg Phe Val Phe Pro Arg Pro Met Thr Asp Arg Pro
            100                 105                 110

Gly Leu Asp Phe Ser Phe Ser Gly Leu Lys Thr Phe Ala Ala Asn Thr
        115                 120                 125

Ile Arg Asp Asn Gly Thr Asp Asp Gln Thr Arg Ala Asp Ile Ala Arg
    130                 135                 140

Ala Phe Glu Asp Ala Val Val Asp Thr Leu Met Ile Lys Cys Lys Arg
145                 150                 155                 160

Ala Leu Asp Gln Thr Gly Phe Lys Arg Leu Val Met Ala Gly Gly Val
                165                 170                 175

Ser Ala Asn Arg Thr Leu Arg Ala Lys Leu Ala Glu Met Met Lys Lys
            180                 185                 190

Arg Arg Gly Glu Val Phe Tyr Ala Arg Pro Glu Phe Cys Thr Asp Asn
        195                 200                 205

Gly Ala Met Ile Ala Tyr Ala Gly Met Val Arg Phe Lys Ala Gly Ala
    210                 215                 220

Thr Ala Asp Leu Gly Val Ser Val Arg Pro Arg Trp Pro Leu Ala Glu
225                 230                 235                 240

Leu Pro Ala Ala

<210> SEQ ID NO 136
<211> LENGTH: 336
<212> TYPE: PRT
<213> ORGANISM: Streptococcus pneumoniae

<400> SEQUENCE: 136

Met Lys Asp Arg Tyr Ile Leu Ala Phe Glu Thr Ser Cys Asp Glu Thr
1               5                   10                  15

Ser Val Ala Val Leu Lys Asn Asp Asp Glu Leu Leu Ser Asn Val Ile
            20                  25                  30

Ala Ser Gln Ile Glu Ser His Lys Arg Phe Gly Gly Val Val Pro Glu
        35                  40                  45

Val Ala Ser Arg His His Val Glu Val Ile Thr Ala Cys Ile Glu Glu
    50                  55                  60

Ala Leu Ala Glu Ala Gly Ile Thr Glu Glu Asp Val Thr Ala Val Ala
65                  70                  75                  80
```

```
Val Thr Tyr Gly Pro Gly Leu Val Gly Ala Leu Leu Val Gly Leu Ser
                85                  90                  95

Ala Ala Lys Ala Phe Ala Trp Ala His Gly Leu Pro Leu Ile Pro Val
            100                 105                 110

Asn His Met Ala Gly His Leu Met Ala Ala Gln Ser Val Glu Pro Leu
            115                 120                 125

Glu Phe Pro Leu Leu Ala Leu Leu Val Ser Gly Gly His Thr Glu Leu
        130                 135                 140

Val Tyr Val Ser Glu Ala Gly Asp Tyr Lys Ile Val Gly Glu Thr Arg
145                 150                 155                 160

Asp Asp Ala Val Gly Glu Ala Tyr Asp Lys Val Gly Arg Val Met Gly
                165                 170                 175

Leu Thr Tyr Pro Ala Gly Arg Glu Ile Asp Glu Leu Ala His Gln Gly
            180                 185                 190

Gln Asp Ile Tyr Asp Phe Pro Arg Ala Met Ile Lys Glu Asp Asn Leu
            195                 200                 205

Glu Phe Ser Phe Ser Gly Leu Lys Ser Ala Phe Ile Asn Leu His His
        210                 215                 220

Asn Ala Glu Gln Lys Gly Glu Ser Leu Ser Thr Glu Asp Leu Cys Ala
225                 230                 235                 240

Ser Phe Gln Ala Ala Val Leu Asp Ile Leu Met Ala Lys Thr Lys Lys
                245                 250                 255

Ala Leu Glu Lys Tyr Pro Val Lys Thr Leu Val Val Ala Gly Gly Val
            260                 265                 270

Ala Ala Asn Lys Gly Leu Arg Glu Arg Leu Ala Ala Glu Val Thr Asp
            275                 280                 285

Val Lys Val Ile Ile Pro Pro Leu Arg Leu Cys Gly Asp Asn Ala Gly
        290                 295                 300

Met Ile Ala Tyr Ala Ser Val Ser Glu Trp Asn Lys Glu Asn Phe Ala
305                 310                 315                 320

Asn Leu Asp Leu Asn Ala Lys Pro Ser Leu Ala Phe Asp Thr Met Glu
                325                 330                 335

<210> SEQ ID NO 137
<211> LENGTH: 240
<212> TYPE: PRT
<213> ORGANISM: artificial sequence
<220> FEATURE:
<223> OTHER INFORMATION: polypeptide or immunogenic fragment of
      Streptococcus spp genes

<400> SEQUENCE: 137

Ala Ala Lys Ala Phe Ala Trp Ala His Gly Leu Pro Leu Ile Pro Val
1               5                   10                  15

Asn His Met Ala Gly His Leu Met Ala Ala Gln Ser Val Glu Pro Leu
            20                  25                  30

Glu Phe Pro Leu Leu Ala Leu Leu Val Ser Gly Gly His Thr Glu Leu
        35                  40                  45

Val Tyr Val Ser Glu Ala Gly Asp Tyr Lys Ile Val Gly Glu Thr Arg
    50                  55                  60

Asp Asp Ala Val Gly Glu Ala Tyr Asp Lys Val Gly Arg Val Met Gly
65                  70                  75                  80

Leu Thr Tyr Pro Ala Gly Arg Glu Ile Asp Glu Leu Ala His Gln Gly
                85                  90                  95

Gln Asp Ile Tyr Asp Phe Pro Arg Ala Met Ile Lys Glu Asp Asn Leu
            100                 105                 110
```

```
Glu Phe Ser Phe Ser Gly Leu Lys Ser Ala Phe Ile Asn Leu His His
            115                 120                 125

Asn Ala Glu Gln Lys Gly Glu Ser Leu Ser Thr Glu Asp Leu Cys Ala
130                 135                 140

Ser Phe Gln Ala Ala Val Leu Asp Ile Leu Met Ala Lys Thr Lys Lys
145                 150                 155                 160

Ala Leu Glu Lys Tyr Pro Val Lys Thr Leu Val Val Ala Gly Gly Val
                165                 170                 175

Ala Ala Asn Lys Gly Leu Arg Glu Arg Leu Ala Ala Glu Val Thr Asp
                180                 185                 190

Val Lys Val Ile Ile Pro Pro Leu Arg Leu Cys Gly Asp Asn Ala Gly
                195                 200                 205

Met Ile Ala Tyr Ala Ser Val Ser Glu Trp Asn Lys Glu Asn Phe Ala
            210                 215                 220

Asn Leu Asp Leu Asn Ala Lys Pro Ser Leu Ala Phe Asp Thr Met Glu
225                 230                 235                 240
```

<210> SEQ ID NO 138
<211> LENGTH: 342
<212> TYPE: PRT
<213> ORGANISM: Yersinia pestis

<400> SEQUENCE: 138

```
Met Met Gly Asn Val Met Arg Val Leu Gly Ile Glu Thr Ser Cys Asp
1               5                   10                  15

Glu Thr Gly Ile Ala Val Tyr Asp Asp Lys Ala Gly Leu Leu Ala Asn
            20                  25                  30

Gln Leu Tyr Ser Gln Val Lys Leu His Ala Asp Tyr Gly Gly Val Val
        35                  40                  45

Pro Glu Leu Ala Ser Arg Asp His Val Arg Lys Thr Val Pro Leu Ile
50                  55                  60

Gln Ala Ala Leu Lys Glu Ala Asn Leu Ser Ala Lys Asp Ile Asp Ala
65                  70                  75                  80

Val Ala Tyr Thr Ala Gly Pro Gly Leu Val Gly Ala Leu Leu Val Gly
                85                  90                  95

Ala Thr Ile Gly Arg Ala Leu Ala Phe Ala Trp Gly Val Pro Ala Val
            100                 105                 110

Pro Val His His Met Glu Gly His Leu Leu Ala Pro Met Leu Glu Glu
            115                 120                 125

Asn Ala Pro Glu Phe Pro Phe Val Ala Leu Leu Val Ser Gly Gly His
130                 135                 140

Thr Gln Leu Ile Ser Val Thr Gly Ile Gly Glu Tyr Leu Leu Leu Gly
145                 150                 155                 160

Glu Ser Val Asp Asp Ala Ala Gly Glu Ala Phe Asp Lys Thr Ala Lys
                165                 170                 175

Leu Leu Gly Leu Asp Tyr Pro Gly Gly Pro Met Leu Ser Arg Met Ala
                180                 185                 190

Gln Gln Gly Thr Val Gly Arg Phe Thr Phe Pro Arg Pro Met Thr Asp
            195                 200                 205

Arg Pro Gly Leu Asp Phe Ser Phe Ser Gly Leu Lys Thr Phe Ala Ala
            210                 215                 220

Asn Thr Ile Arg Ala Asn Gly Asp Asp Gln Thr Arg Ala Asp Ile
225                 230                 235                 240

Ala Arg Ala Phe Glu Asp Ala Val Val Asp Thr Leu Ala Ile Lys Ser
```

```
              245                 250                 255
Lys Arg Ala Leu Asp Gln Thr Gly Phe Lys Arg Leu Val Ile Ala Gly
            260                 265                 270

Gly Val Ser Ala Asn Gln Thr Leu Arg Leu Lys Leu Ala Asp Met Met
        275                 280                 285

Gln Lys Arg Gly Gly Glu Val Phe Tyr Ala Arg Pro Glu Phe Cys Thr
    290                 295                 300

Asp Asn Gly Ala Met Ile Ala Tyr Ala Gly Met Val Arg Leu Arg Ser
305                 310                 315                 320

Asn Leu Asn Ser Glu Leu Ser Val Ser Val Arg Pro Arg Trp Pro Leu
                325                 330                 335

Ser Glu Leu Pro Lys Val
            340

<210> SEQ ID NO 139
<211> LENGTH: 242
<212> TYPE: PRT
<213> ORGANISM: artificial sequence
<220> FEATURE:
<223> OTHER INFORMATION: polypeptide or immunogenic fragment of Yersinia
      spp genes

<400> SEQUENCE: 139

Arg Ala Leu Ala Phe Ala Trp Gly Val Pro Ala Val Pro Val His His
1               5                   10                  15

Met Glu Gly His Leu Leu Ala Pro Met Leu Glu Glu Asn Ala Pro Glu
            20                  25                  30

Phe Pro Phe Val Ala Leu Leu Val Ser Gly Gly His Thr Gln Leu Ile
        35                  40                  45

Ser Val Thr Gly Ile Gly Glu Tyr Leu Leu Leu Gly Glu Ser Val Asp
    50                  55                  60

Asp Ala Ala Gly Glu Ala Phe Asp Lys Thr Ala Lys Leu Leu Gly Leu
65                  70                  75                  80

Asp Tyr Pro Gly Gly Pro Met Leu Ser Arg Met Ala Gln Gln Gly Thr
                85                  90                  95

Val Gly Arg Phe Thr Phe Pro Arg Pro Met Thr Asp Arg Pro Gly Leu
            100                 105                 110

Asp Phe Ser Phe Ser Gly Leu Lys Thr Phe Ala Ala Asn Thr Ile Arg
        115                 120                 125

Ala Asn Gly Asp Asp Gln Thr Arg Ala Asp Ile Ala Arg Ala Phe
130                 135                 140

Glu Asp Ala Val Val Asp Thr Leu Ala Ile Lys Ser Lys Arg Ala Leu
145                 150                 155                 160

Asp Gln Thr Gly Phe Lys Arg Leu Val Ile Ala Gly Gly Val Ser Ala
                165                 170                 175

Asn Gln Thr Leu Arg Leu Lys Leu Ala Asp Met Met Gln Lys Arg Gly
            180                 185                 190

Gly Glu Val Phe Tyr Ala Arg Pro Glu Phe Cys Thr Asp Asn Gly Ala
        195                 200                 205

Met Ile Ala Tyr Ala Gly Met Val Arg Leu Arg Ser Asn Leu Asn Ser
    210                 215                 220

Glu Leu Ser Val Ser Val Arg Pro Arg Trp Pro Leu Ser Glu Leu Pro
225                 230                 235                 240

Lys Val
```

<210> SEQ ID NO 140
<211> LENGTH: 336
<212> TYPE: PRT
<213> ORGANISM: Streptococcus agalactiae

<400> SEQUENCE: 140

```
Met Lys Asp Arg Tyr Ile Leu Ala Val Glu Ser Ser Cys Asp Glu Thr
1               5                   10                  15

Ser Val Ala Ile Leu Lys Asn Asp Lys Glu Leu Leu Ala Asn Ile Ile
            20                  25                  30

Ala Ser Gln Val Glu Ser His Lys Arg Phe Gly Gly Val Val Pro Glu
        35                  40                  45

Val Ala Ser Arg His His Val Glu Val Val Thr Thr Cys Phe Glu Asp
50                  55                  60

Ala Leu Gln Glu Ala Gly Ile Val Ala Ser Asp Leu Asp Ala Val Ala
65                  70                  75                  80

Val Thr Tyr Gly Pro Gly Leu Val Gly Ala Leu Leu Val Gly Met Ala
                85                  90                  95

Ala Ala Lys Ala Phe Ala Trp Ala Asn Lys Leu Pro Leu Ile Pro Ile
            100                 105                 110

Asn His Met Ala Gly His Leu Met Ala Ala Arg Asp Val Lys Glu Leu
        115                 120                 125

Gln Tyr Pro Leu Leu Ala Leu Leu Val Ser Gly Gly His Thr Glu Leu
    130                 135                 140

Val Tyr Val Ser Glu Pro Gly Asp Tyr Lys Ile Val Gly Glu Thr Arg
145                 150                 155                 160

Asp Asp Ala Val Gly Glu Ala Tyr Asp Lys Val Gly Arg Val Met Gly
                165                 170                 175

Leu Thr Tyr Pro Ala Gly Arg Glu Ile Asp Gln Leu Ala His Lys Gly
            180                 185                 190

Gln Asp Thr Tyr His Phe Pro Arg Ala Met Ile Lys Glu Asp His Leu
        195                 200                 205

Glu Phe Ser Phe Ser Gly Leu Lys Ser Ala Phe Ile Asn Leu His His
    210                 215                 220

Asn Ala Glu Gln Lys Gly Glu Ala Leu Val Leu Glu Asp Leu Cys Ala
225                 230                 235                 240

Ser Phe Gln Ala Ala Val Leu Asp Ile Leu Leu Ala Lys Thr Gln Lys
                245                 250                 255

Ala Leu Leu Lys Tyr Pro Val Lys Thr Leu Val Val Ala Gly Gly Val
            260                 265                 270

Ala Ala Asn Gln Gly Leu Arg Glu Arg Leu Ala Thr Asp Ile Ser Pro
        275                 280                 285

Asp Ile Asp Val Val Ile Pro Pro Leu Arg Leu Cys Gly Asp Asn Ala
    290                 295                 300

Gly Met Ile Ala Leu Ala Ala Ala Ile Glu Phe Glu Lys Glu Asn Phe
305                 310                 315                 320

Ala Ser Leu Lys Leu Asn Ala Lys Pro Ser Leu Ala Phe Glu Ser Leu
                325                 330                 335
```

<210> SEQ ID NO 141
<211> LENGTH: 241
<212> TYPE: PRT
<213> ORGANISM: artificial sequence
<220> FEATURE:
<223> OTHER INFORMATION: polypeptide or immunogenic fragment of
    Streptococcus spp genes -continued

```
<400> SEQUENCE: 141

Ala Ala Ala Lys Ala Phe Ala Trp Ala Asn Lys Leu Pro Leu Ile Pro
1               5                   10                  15

Ile Asn His Met Ala Gly His Leu Met Ala Ala Arg Asp Val Lys Glu
            20                  25                  30

Leu Gln Tyr Pro Leu Leu Ala Leu Leu Val Ser Gly His Thr Glu
        35                  40                  45

Leu Val Tyr Val Ser Glu Pro Gly Asp Tyr Lys Ile Val Gly Glu Thr
    50                  55                  60

Arg Asp Asp Ala Val Gly Glu Ala Tyr Asp Lys Val Gly Arg Val Met
65                  70                  75                  80

Gly Leu Thr Tyr Pro Ala Gly Arg Glu Ile Asp Gln Leu Ala His Lys
                85                  90                  95

Gly Gln Asp Thr Tyr His Phe Pro Arg Ala Met Ile Lys Glu Asp His
            100                 105                 110

Leu Glu Phe Ser Phe Ser Gly Leu Lys Ser Ala Phe Ile Asn Leu His
        115                 120                 125

His Asn Ala Glu Gln Lys Gly Glu Ala Leu Val Leu Glu Asp Leu Cys
    130                 135                 140

Ala Ser Phe Gln Ala Ala Val Leu Asp Ile Leu Leu Ala Lys Thr Gln
145                 150                 155                 160

Lys Ala Leu Leu Lys Tyr Pro Val Lys Thr Leu Val Val Ala Gly Gly
                165                 170                 175

Val Ala Ala Asn Gln Gly Leu Arg Glu Arg Leu Ala Thr Asp Ile Ser
            180                 185                 190

Pro Asp Ile Asp Val Val Ile Pro Pro Leu Arg Leu Cys Gly Asp Asn
        195                 200                 205

Ala Gly Met Ile Ala Leu Ala Ala Ile Glu Phe Glu Lys Glu Asn
    210                 215                 220

Phe Ala Ser Leu Lys Leu Asn Ala Lys Pro Ser Leu Ala Phe Glu Ser
225                 230                 235                 240

Leu

<210> SEQ ID NO 142
<211> LENGTH: 342
<212> TYPE: PRT
<213> ORGANISM: Streptococcus pyogenes

<400> SEQUENCE: 142

Met Thr Asp Arg Tyr Ile Leu Ala Val Glu Ser Ser Cys Asp Glu Thr
1               5                   10                  15

Ser Val Ala Ile Leu Lys Asn Glu Ser Thr Leu Leu Ser Asn Val Ile
            20                  25                  30

Ala Ser Gln Val Glu Ser His Lys Arg Phe Gly Gly Val Val Pro Glu
        35                  40                  45

Val Ala Ser Arg His His Val Glu Val Ile Thr Thr Cys Phe Glu Asp
    50                  55                  60

Ala Leu Gln Glu Ala Gly Ile Ser Ala Ser Asp Leu Ser Ala Val Ala
65                  70                  75                  80

Val Thr Tyr Gly Pro Gly Leu Val Gly Ala Leu Leu Val Gly Leu Ala
                85                  90                  95

Ala Ala Lys Ala Phe Ala Trp Ala Asn His Leu Pro Leu Ile Pro Val
            100                 105                 110

Asn His Met Ala Gly His Leu Met Ala Ala Arg Glu Gln Glu Pro Leu
```

```
            115                 120                 125
Val Tyr Pro Leu Ile Ala Leu Leu Val Ser Gly Gly His Thr Glu Leu
    130                 135                 140

Val Tyr Val Pro Glu Pro Gly Asp Tyr His Ile Ile Gly Glu Thr Arg
145                 150                 155                 160

Asp Asp Ala Val Gly Glu Ala Tyr Asp Lys Val Gly Arg Val Met Gly
                165                 170                 175

Leu Thr Tyr Pro Ala Gly Arg Glu Ile Asp Gln Leu Ala His Lys Gly
            180                 185                 190

Gln Asp Thr Tyr His Phe Pro Arg Ala Met Ile Thr Glu Asp His Leu
        195                 200                 205

Glu Phe Ser Phe Ser Gly Leu Lys Ser Ala Phe Ile Asn Leu His His
    210                 215                 220

Asn Ala Lys Gln Lys Gly Asn Glu Leu Ile Leu Glu Asp Leu Cys Ala
225                 230                 235                 240

Ser Phe Gln Ala Ala Val Leu Asp Ile Leu Leu Ala Lys Thr Lys Lys
                245                 250                 255

Ala Leu Ser Arg Tyr Pro Ala Lys Met Leu Val Val Ala Gly Gly Val
            260                 265                 270

Ala Ala Asn Gln Gly Leu Arg Asp Arg Leu Ala Gln Glu Ile Thr His
        275                 280                 285

Ile Glu Val Val Ile Pro Lys Leu Arg Leu Cys Gly Asp Asn Ala Gly
    290                 295                 300

Met Ile Ala Leu Ala Ala Ile Glu Tyr Asp Lys Gln His Phe Ala
305                 310                 315                 320

Asn Met Ser Leu Asn Ala Lys Pro Ser Leu Ala Phe Asp Gln Phe Pro
                325                 330                 335

Asp Ser Phe Val Ile Asn
            340
```

```
<210> SEQ ID NO 143
<211> LENGTH: 247
<212> TYPE: PRT
<213> ORGANISM: artificial sequence
<220> FEATURE:
<223> OTHER INFORMATION: polypeptide or immunogenic fragment of
      Streptococcus spp genes

<400> SEQUENCE: 143
```

```
Ala Ala Ala Lys Ala Phe Ala Trp Ala Asn His Leu Pro Leu Ile Pro
1               5                   10                  15

Val Asn His Met Ala Gly His Leu Met Ala Ala Arg Glu Gln Glu Pro
                20                  25                  30

Leu Val Tyr Pro Leu Ile Ala Leu Leu Val Ser Gly Gly His Thr Glu
            35                  40                  45

Leu Val Tyr Val Pro Glu Pro Gly Asp Tyr His Ile Ile Gly Glu Thr
        50                  55                  60

Arg Asp Asp Ala Val Gly Glu Ala Tyr Asp Lys Val Gly Arg Val Met
65                  70                  75                  80

Gly Leu Thr Tyr Pro Ala Gly Arg Glu Ile Asp Gln Leu Ala His Lys
                85                  90                  95

Gly Gln Asp Thr Tyr His Phe Pro Arg Ala Met Ile Thr Glu Asp His
            100                 105                 110

Leu Glu Phe Ser Phe Ser Gly Leu Lys Ser Ala Phe Ile Asn Leu His
        115                 120                 125
```

His Asn Ala Lys Gln Lys Gly Asn Glu Leu Ile Leu Glu Asp Leu Cys
    130                 135                 140

Ala Ser Phe Gln Ala Ala Val Leu Asp Ile Leu Leu Ala Lys Thr Lys
145                 150                 155                 160

Lys Ala Leu Ser Arg Tyr Pro Ala Lys Met Leu Val Val Ala Gly Gly
                165                 170                 175

Val Ala Ala Asn Gln Gly Leu Arg Asp Arg Leu Ala Gln Glu Ile Thr
            180                 185                 190

His Ile Glu Val Val Ile Pro Lys Leu Arg Leu Cys Gly Asp Asn Ala
        195                 200                 205

Gly Met Ile Ala Leu Ala Ala Ile Glu Tyr Asp Lys Gln His Phe
    210                 215                 220

Ala Asn Met Ser Leu Asn Ala Lys Pro Ser Leu Ala Phe Asp Gln Phe
225                 230                 235                 240

Pro Asp Ser Phe Val Ile Asn
                245

<210> SEQ ID NO 144
<211> LENGTH: 265
<212> TYPE: PRT
<213> ORGANISM: Bacillus anthracis

<400> SEQUENCE: 144

Met Lys Asn Ser Lys Val Ile Lys Leu Gln Asp Arg Val Pro Lys Leu
1               5                   10                  15

Lys Asn Gln Gln Lys Lys Lys Lys Asn Val Asn His Arg Leu Ile
            20                  25                  30

Leu Tyr Ile Ser Ile Leu Phe Leu Leu Val Leu Phe Leu Ile Tyr Phe
        35                  40                  45

Arg Ser Pro Leu Ser Asn Ile Lys Lys Ile Ser Val Phe Gly Asn His
    50                  55                  60

Tyr Met Thr Asp Glu Gln Val Met Lys Glu Ser Gly Val Thr Tyr Asp
65                  70                  75                  80

Thr Ser Tyr Phe Arg Val Thr Ala His Lys Ala Glu Glu Asn Leu Thr
                85                  90                  95

Lys Arg Lys Glu Ile Lys Ala Val Asn Val Lys Lys Arg Phe Pro Asn
            100                 105                 110

Lys Ile Asp Val His Ile Glu Glu Tyr Leu Thr Ile Gly Tyr Ile Asn
        115                 120                 125

Lys Asp Gly Lys Leu Gln Pro Leu Leu Glu Asn Gly Lys Thr Leu Asp
    130                 135                 140

Val Leu Pro Asn Gly Lys Leu Pro Val Ala Ala Pro Ile Phe Glu Pro
145                 150                 155                 160

Phe Lys Glu Glu Lys Met Lys Glu Leu Ile Ala Glu Leu Glu Lys Leu
                165                 170                 175

Thr Pro Thr Ile Leu Arg Ser Ile Ser Glu Ile Arg Tyr Ser Pro Thr
            180                 185                 190

Asn Ala Asn Glu Asp His Leu Thr Leu Tyr Met Asn Glu Gly Tyr Glu
        195                 200                 205

Val Ser Thr Thr Ile Gln Asn Phe Ala Lys Arg Met Glu Thr Tyr Pro
    210                 215                 220

Leu Ile Leu Lys Thr Ile Glu Pro Gly Lys Lys Val Leu Ile Asp Leu
225                 230                 235                 240

Glu Val Gly Ala Tyr Thr Lys Glu Leu Gly Ala Glu Glu Lys Lys Asn
                245                 250                 255

-continued

```
Arg Met Ile Val Phe Asn Thr Leu Ser
            260                 265

<210> SEQ ID NO 145
<211> LENGTH: 220
<212> TYPE: PRT
<213> ORGANISM: Artificial Sequence
<220> FEATURE:
<223> OTHER INFORMATION: polypeptide or immunogenic fragment of Bacillus
      spp genes

<400> SEQUENCE: 145

Ile Tyr Phe Arg Ser Pro Leu Ser Asn Ile Lys Lys Ile Ser Val Phe
1               5                   10                  15

Gly Asn His Tyr Met Thr Asp Glu Gln Val Met Lys Glu Ser Gly Val
            20                  25                  30

Thr Tyr Asp Thr Ser Tyr Phe Arg Val Thr Ala His Lys Ala Glu Glu
        35                  40                  45

Asn Leu Thr Lys Arg Lys Glu Ile Lys Ala Val Asn Val Lys Lys Arg
    50                  55                  60

Phe Pro Asn Lys Ile Asp Val His Ile Glu Glu Tyr Leu Thr Ile Gly
65                  70                  75                  80

Tyr Ile Asn Lys Asp Gly Lys Leu Gln Pro Leu Leu Glu Asn Gly Lys
                85                  90                  95

Thr Leu Asp Val Leu Pro Asn Gly Lys Leu Pro Val Ala Ala Pro Ile
            100                 105                 110

Phe Glu Pro Phe Lys Glu Glu Lys Met Lys Glu Leu Ile Ala Glu Leu
        115                 120                 125

Glu Lys Leu Thr Pro Thr Ile Leu Arg Ser Ile Ser Glu Ile Arg Tyr
    130                 135                 140

Ser Pro Thr Asn Ala Asn Glu Asp His Leu Thr Leu Tyr Met Asn Glu
145                 150                 155                 160

Gly Tyr Glu Val Ser Thr Thr Ile Gln Asn Phe Ala Lys Arg Met Glu
                165                 170                 175

Thr Tyr Pro Leu Ile Leu Lys Thr Ile Glu Pro Gly Lys Lys Val Leu
            180                 185                 190

Ile Asp Leu Glu Val Gly Ala Tyr Thr Lys Glu Leu Gly Ala Glu Glu
        195                 200                 205

Lys Lys Asn Arg Met Ile Val Phe Asn Thr Leu Ser
    210                 215                 220

<210> SEQ ID NO 146
<211> LENGTH: 256
<212> TYPE: PRT
<213> ORGANISM: Clostridium botulinum

<400> SEQUENCE: 146

Met Ser Lys Asp Leu Ile Ser Thr Asp Glu Tyr Ile Lys Ile Lys Lys
1               5                   10                  15

Lys Arg Lys Arg Ile Lys Lys Ile Val Val Leu Phe Ile Phe Leu Ile
            20                  25                  30

Ser Ile Leu Val Thr Leu Cys Leu Lys Ile Pro Tyr Phe Asn Ile Glu
        35                  40                  45

Ser Ile Glu Ile Lys Gly Asn Val Asn Ile Pro Lys Glu Ile Ile Lys
    50                  55                  60

Asp Ser Ser Thr Ile Lys Thr Gly Asn Asn Ile Phe Tyr Thr Asn Lys
65                  70                  75                  80
```

```
Lys Asp Ala Ile Glu Asn Ile Ser Leu Asn Pro Tyr Ile Glu Val
                85                  90                  95

Lys Ile Thr Lys Lys Leu Pro Asn Lys Leu Glu Ile Tyr Val Lys Glu
            100                 105                 110

Arg Glu Ala Leu Phe Tyr Asn Lys Val Asp Lys Asp Phe Phe Ile Ile
            115                 120                 125

Ser Lys Asn Gly Cys Leu Leu Glu Lys Arg Lys Glu Ile Lys Asn Met
130                 135                 140

Lys Leu Ile Asn Leu Gln Gly Phe Glu Phe Asn Glu Ser Lys Ile Gly
145                 150                 155                 160

Ser Ala Leu Lys Ala Lys Asp Glu Arg Gly Val Lys Ile Leu Asn Asp
                165                 170                 175

Phe Gly Val Leu Leu Lys Asn Asn Ala Ser Asp Val Ile Phe Thr Gln
                180                 185                 190

Leu Asp Leu Arg Asn Leu Leu Asp Ile Arg Ile Tyr Ser Asn Gly Ile
                195                 200                 205

Cys Val Lys Ile Gly Thr Ser Asp Gln Ile Glu Lys Lys Leu Asn Thr
210                 215                 220

Ala Ile Asn Ile Leu Lys Arg Asp Glu Leu Lys Lys Ala Lys Lys Gly
225                 230                 235                 240

Tyr Val Asp Val Ser Tyr Glu Gly Asn Pro Val Phe Tyr Ile Glu Lys
                245                 250                 255

<210> SEQ ID NO 147
<211> LENGTH: 218
<212> TYPE: PRT
<213> ORGANISM: artificial sequence
<220> FEATURE:
<223> OTHER INFORMATION: polypeptide or immunogenic fragment of
      Clostridium spp genes

<400> SEQUENCE: 147

Cys Leu Lys Ile Pro Tyr Phe Asn Ile Glu Ser Ile Glu Ile Lys Gly
1               5                   10                  15

Asn Val Asn Ile Pro Lys Glu Ile Ile Lys Asp Ser Ser Thr Ile Lys
                20                  25                  30

Thr Gly Asn Asn Ile Phe Tyr Thr Asn Lys Lys Asp Ala Ile Glu Asn
            35                  40                  45

Ile Ser Leu Asn Pro Tyr Ile Glu Glu Val Lys Ile Thr Lys Lys Leu
50                  55                  60

Pro Asn Lys Leu Glu Ile Tyr Val Lys Glu Arg Glu Ala Leu Phe Tyr
65                  70                  75                  80

Asn Lys Val Asp Lys Asp Phe Phe Ile Ile Ser Lys Asn Gly Cys Leu
                85                  90                  95

Leu Glu Lys Arg Lys Glu Ile Lys Asn Met Lys Leu Ile Asn Leu Gln
            100                 105                 110

Gly Phe Glu Phe Asn Glu Ser Lys Ile Gly Ser Ala Leu Lys Ala Lys
        115                 120                 125

Asp Glu Arg Gly Val Lys Ile Leu Asn Asp Phe Gly Val Leu Leu Lys
    130                 135                 140

Asn Asn Ala Ser Asp Val Ile Phe Thr Gln Leu Asp Leu Arg Asn Leu
145                 150                 155                 160

Leu Asp Ile Arg Ile Tyr Ser Asn Gly Ile Cys Val Lys Ile Gly Thr
                165                 170                 175

Ser Asp Gln Ile Glu Lys Lys Leu Asn Thr Ala Ile Asn Ile Leu Lys
```

```
              180                 185                 190
Arg Asp Glu Leu Lys Lys Ala Lys Lys Gly Tyr Val Asp Val Ser Tyr
            195                 200                 205

Glu Gly Asn Pro Val Phe Tyr Ile Glu Lys
            210                 215

<210> SEQ ID NO 148
<211> LENGTH: 246
<212> TYPE: PRT
<213> ORGANISM: Clostridium difficile

<400> SEQUENCE: 148

Met Lys Lys Arg Arg Lys Leu Asn Thr Asn Asn Val Met Ile Ile Leu
1               5                  10                  15

Val Phe Ile Leu Met Leu Ser Phe Cys Ile Cys Ile Ile Val Lys Ser
             20                  25                  30

Asp Leu Phe Asp Val Lys Lys Ile Asp Val Ile Gly Asn Lys Arg Val
         35                  40                  45

Thr Lys Ser Asn Ile Met Lys Glu Leu Asn Val Asn Leu Asn Glu Asn
     50                  55                  60

Ile Phe Ala Tyr Asn Phe Lys Asp Met Lys Asn Lys Leu Ile Lys Asn
65                  70                  75                  80

Pro Tyr Ile Glu Asn Val Glu Ile Lys Arg Lys Leu Pro Asn Lys Ile
                 85                  90                  95

Ile Ile Ser Leu Lys Glu Lys Glu Ile Phe Ala Val Leu Lys Asp Glu
            100                 105                 110

Asp Asn Tyr Cys Tyr Ile Asp Lys Lys Gly Asn Leu Leu Glu Glu Leu
        115                 120                 125

Arg Gly Ser Asn Glu Ser Lys Lys Asp Leu Ile Val Asp Val Asp Tyr
    130                 135                 140

Ser Ile Asp Asp Asn Lys Ser Ile Lys Phe Leu Asn Tyr Lys Thr Lys
145                 150                 155                 160

Glu Asn Val Phe Lys Thr Leu Asn Tyr Leu Lys Glu Gly Ile Tyr
                165                 170                 175

Arg Lys Ile Asn Tyr Val Asn Leu Lys Lys Glu Ser Asn Ile Glu Met
            180                 185                 190

Leu Thr Arg Ser Asn Ile Lys Ile Leu Leu Ser Asn Asp Asp Asn Leu
        195                 200                 205

Asp Tyr Asn Ile Ser Arg Val Ser Lys Ile Leu Ile Asp Leu Gln Asn
    210                 215                 220

Lys Asn Thr Asn Gly Gly Thr Ile Asn Leu Asn Tyr Gly Lys Leu Ala
225                 230                 235                 240

Val Tyr Ser Pro Glu Gly
                245

<210> SEQ ID NO 149
<211> LENGTH: 219
<212> TYPE: PRT
<213> ORGANISM: artificial sequence
<220> FEATURE:
<223> OTHER INFORMATION: polypeptide or immunogenic fragment of
      Clostridium spp genes

<400> SEQUENCE: 149

Ile Ile Val Lys Ser Asp Leu Phe Asp Val Lys Lys Ile Asp Val Ile
1               5                  10                  15

Gly Asn Lys Arg Val Thr Lys Ser Asn Ile Met Lys Glu Leu Asn Val
```

```
            20                  25                  30
Asn Leu Asn Glu Asn Ile Phe Ala Tyr Asn Phe Lys Asp Met Lys Asn
            35                  40                  45
Lys Leu Ile Lys Asn Pro Tyr Ile Glu Asn Val Glu Ile Lys Arg Lys
         50                  55                  60
Leu Pro Asn Lys Ile Ile Ile Ser Leu Lys Glu Lys Glu Ile Phe Ala
 65                  70                  75                  80
Val Leu Lys Asp Glu Asp Asn Tyr Cys Tyr Ile Asp Lys Lys Gly Asn
                 85                  90                  95
Leu Leu Glu Glu Leu Arg Gly Ser Asn Glu Ser Lys Lys Asp Leu Ile
                100                 105                 110
Val Asp Val Asp Tyr Ser Ile Asp Asp Asn Lys Ser Ile Lys Phe Lys
            115                 120                 125
Asn Tyr Lys Thr Lys Glu Asn Val Phe Lys Thr Leu Asn Tyr Leu Lys
        130                 135                 140
Glu Gly Ile Tyr Arg Lys Ile Asn Tyr Val Asn Leu Lys Lys Glu
145                 150                 155                 160
Ser Asn Ile Glu Met Leu Thr Arg Ser Asn Ile Lys Ile Leu Leu Ser
                165                 170                 175
Asn Asp Asp Asn Leu Asp Tyr Asn Ile Ser Arg Val Ser Lys Ile Leu
                180                 185                 190
Ile Asp Leu Gln Asn Lys Asn Thr Asn Gly Gly Thr Ile Asn Leu Asn
            195                 200                 205
Tyr Gly Lys Leu Ala Val Tyr Ser Pro Glu Gly
        210                 215

<210> SEQ ID NO 150
<211> LENGTH: 374
<212> TYPE: PRT
<213> ORGANISM: Enterococcus faecalis

<400> SEQUENCE: 150

Met Trp Lys Ile Ser Asn Glu Asn Asp Ile Phe Lys Lys Arg Lys Pro
 1               5                  10                  15
Leu Pro Pro Lys Lys Ser Glu Glu Ser Gln Pro Glu Leu Thr Pro Trp
            20                  25                  30
Gln Lys Gln Asn Gln Glu Tyr Leu Lys Lys Gln Ala Glu Glu Ala Ala
            35                  40                  45
Ser Lys Gly Glu Asn Glu Gln Ala Glu Val Thr Ile Thr Leu Gln Glu
         50                  55                  60
Gln Ser Gln Glu Glu Pro Gln Gln His Leu Pro Gln Glu Thr Val Glu
 65                  70                  75                  80
Glu Glu Glu His Phe Ala Asp Arg Leu Pro Asn Val Lys Lys Thr Arg
                 85                  90                  95
Asn Lys Arg Leu Tyr Arg Arg Leu Ala Phe Ile Leu Thr Cys Leu Gly
                100                 105                 110
Thr Ala Ile Leu Val Ala Leu Tyr Phe Val Ser Pro Leu Ser Arg Leu
            115                 120                 125
Ser Glu Val Thr Val Ser Gly Asn Lys Ser Val Glu Ser Gln Ala Ile
        130                 135                 140
Ile Gln Gln Ser Lys Leu Glu Thr Gly Ser Gly Leu Trp Glu Gln Tyr
145                 150                 155                 160
Ser Asn Arg Asn Tyr Phe Ser Ala Asn Ile Gln Lys Lys Phe Pro Ile
                165                 170                 175
```

```
Ile Lys Lys Ala Asn Ile Lys Leu Asn Gly Ile Asn Ser Phe Lys Ile
            180                 185                 190

Asp Ile Gln Glu Tyr Gln Ile Val Ala Leu Ala Thr Lys Gly Gly
        195                 200                 205

Tyr His Pro Ile Leu Glu Asn Gly Lys Thr Leu Ala Glu Thr Thr Lys
    210                 215                 220

Ala Ala Glu Ser Gly Lys Pro Ile Phe Glu Asn Phe Lys Glu Asp Lys
225                 230                 235                 240

Leu Ile Pro Glu Leu Met Ala Ser Tyr Asn Lys Leu Pro Gln Glu Ile
                245                 250                 255

Lys Gln Gly Ile Ser Glu Ile Lys Tyr Ala Pro Ser Lys Thr Asn Lys
            260                 265                 270

Asp Leu Ile Asn Val Tyr Met Asn Asp Gly Asn Arg Val Ile Val Asn
        275                 280                 285

Ile Ser Asp Leu Ser Glu Lys Met Ala Tyr Tyr Ser Gln Val Ala Glu
    290                 295                 300

Gln Met Asp Lys Pro Gly Ile Val Asp Met Glu Val Gly Ile Phe Ser
305                 310                 315                 320

Tyr Pro Tyr Glu Lys Glu Ser Glu Glu Thr Gly Ser Glu Val Ser Glu
                325                 330                 335

Asp Ser Ala Ala Glu Asn Gln Glu Val Val Asp Pro Asn Ala Gly Val
            340                 345                 350

Ala Thr Asp Glu Ala Asn Asn Gly Thr Pro Thr Asn Gly Glu Asn Gln
        355                 360                 365

Glu Val Gln Gln Ala Glu
    370

<210> SEQ ID NO 151
<211> LENGTH: 254
<212> TYPE: PRT
<213> ORGANISM: artificial sequence
<220> FEATURE:
<223> OTHER INFORMATION: polypeptide or immunogenic fragment of
      Enetrococcus spp genes

<400> SEQUENCE: 151

Phe Val Ser Pro Leu Ser Arg Leu Ser Glu Val Thr Val Ser Gly Asn
1               5                   10                  15

Lys Ser Val Glu Ser Gln Ala Ile Ile Gln Gln Ser Lys Leu Glu Thr
            20                  25                  30

Gly Ser Gly Leu Trp Glu Gln Tyr Ser Asn Arg Asn Tyr Phe Ser Ala
        35                  40                  45

Asn Ile Gln Lys Lys Phe Pro Ile Ile Lys Ala Asn Ile Lys Leu
50                  55                  60

Asn Gly Ile Asn Ser Phe Lys Ile Asp Ile Gln Glu Tyr Gln Ile Val
65                  70                  75                  80

Ala Leu Ala Ala Thr Lys Gly Gly Tyr His Pro Ile Leu Glu Asn Gly
                85                  90                  95

Lys Thr Leu Ala Glu Thr Thr Lys Ala Ala Glu Ser Gly Lys Pro Ile
            100                 105                 110

Phe Glu Asn Phe Lys Glu Asp Lys Leu Ile Pro Glu Leu Met Ala Ser
        115                 120                 125

Tyr Asn Lys Leu Pro Gln Glu Ile Lys Gln Gly Ile Ser Glu Ile Lys
    130                 135                 140

Tyr Ala Pro Ser Lys Thr Asn Lys Asp Leu Ile Asn Val Tyr Met Asn
145                 150                 155                 160
```

```
Asp Gly Asn Arg Val Ile Val Asn Ile Ser Asp Leu Ser Glu Lys Met
                165                 170                 175

Ala Tyr Tyr Ser Gln Val Ala Glu Gln Met Asp Lys Pro Gly Ile Val
            180                 185                 190

Asp Met Glu Val Gly Ile Phe Ser Tyr Pro Tyr Glu Lys Glu Ser Glu
        195                 200                 205

Glu Thr Gly Ser Glu Val Ser Glu Asp Ser Ala Ala Glu Asn Gln Glu
    210                 215                 220

Val Val Asp Pro Asn Ala Gly Val Ala Thr Asp Glu Ala Asn Asn Gly
225                 230                 235                 240

Thr Pro Thr Asn Gly Glu Asn Gln Glu Val Gln Gln Ala Glu
                245                 250

<210> SEQ ID NO 152
<211> LENGTH: 399
<212> TYPE: PRT
<213> ORGANISM: Streptococcus pneumoniae

<400> SEQUENCE: 152

Met Ser Lys Asp Lys Asn Glu Asp Lys Glu Thr Leu Glu Leu
1               5                   10                  15

Lys Glu Leu Ser Glu Trp Gln Lys Arg Asn Gln Glu Tyr Leu Lys Lys
            20                  25                  30

Lys Ala Glu Glu Ala Ala Leu Ala Glu Glu Lys Glu Lys Glu Arg
        35                  40                  45

Gln Ala Arg Met Gly Glu Glu Ser Glu Lys Ser Glu Asp Lys Gln Asp
    50                  55                  60

Gln Glu Ser Glu Thr Asp Gln Glu Asp Ser Glu Ser Ala Lys Glu Glu
65                  70                  75                  80

Ser Glu Glu Lys Val Ala Ser Ser Glu Ala Asp Lys Glu Lys Glu Glu
                85                  90                  95

Lys Glu Glu Ser Glu Ser Lys Glu Lys Glu Glu Gln Asp Lys Lys Leu
            100                 105                 110

Ala Lys Lys Ala Thr Lys Glu Lys Pro Ala Lys Ala Lys Ile Pro Gly
        115                 120                 125

Ile His Ile Leu Arg Ala Phe Thr Ile Leu Phe Pro Ser Leu Leu Leu
    130                 135                 140

Leu Ile Val Ser Ala Tyr Leu Leu Ser Pro Tyr Ala Thr Met Lys Asp
145                 150                 155                 160

Ile Arg Val Glu Gly Thr Val Gln Thr Thr Ala Asp Asp Ile Arg Gln
                165                 170                 175

Val Ser Gly Ile Gln Asp Ser Asp Tyr Thr Ile Asn Leu Leu Leu Asp
            180                 185                 190

Lys Ala Lys Tyr Glu Lys Gln Ile Lys Ser Asn Tyr Trp Val Glu Ser
        195                 200                 205

Ala Gln Leu Val Tyr Gln Phe Pro Thr Lys Phe Thr Ile Lys Val Lys
    210                 215                 220

Glu Tyr Asp Ile Val Ala Tyr Tyr Ile Ser Gly Glu Asn His Tyr Pro
225                 230                 235                 240

Ile Leu Ser Ser Gly Gln Leu Glu Thr Ser Ser Val Ser Leu Asn Ser
                245                 250                 255

Leu Pro Glu Thr Tyr Leu Ser Val Leu Phe Asn Asp Ser Glu Gln Ile
            260                 265                 270

Lys Val Phe Val Ser Glu Leu Ala Gln Ile Ser Pro Glu Leu Lys Ala
```

```
                275                 280                 285
Ala Ile Gln Lys Val Glu Leu Ala Pro Ser Lys Val Thr Ser Asp Leu
    290                 295                 300

Ile Arg Leu Thr Met Asn Asp Ser Asp Glu Val Leu Val Pro Leu Ser
305                 310                 315                 320

Glu Met Ser Lys Lys Leu Pro Tyr Tyr Ser Lys Ile Lys Pro Gln Leu
                325                 330                 335

Ser Glu Pro Ser Val Val Asp Met Glu Ala Gly Ile Tyr Ser Tyr Thr
            340                 345                 350

Val Ala Asp Lys Leu Ile Met Glu Ala Glu Lys Ala Lys Gln Glu
        355                 360                 365

Ala Lys Glu Ala Glu Lys Lys Gln Glu Glu Gln Lys Lys Gln Glu
    370                 375                 380

Glu Glu Ser Asn Arg Asn Gln Thr Thr Gln Arg Ser Ser Arg Arg
385                 390                 395

<210> SEQ ID NO 153
<211> LENGTH: 255
<212> TYPE: PRT
<213> ORGANISM: artificial sequence
<220> FEATURE:
<223> OTHER INFORMATION: polypeptide or immunogenic fragment of
      Streptococcus spp genes

<400> SEQUENCE: 153

Leu Ile Val Ser Ala Tyr Leu Leu Ser Pro Tyr Ala Thr Met Lys Asp
1               5                   10                  15

Ile Arg Val Glu Gly Thr Val Gln Thr Thr Ala Asp Asp Ile Arg Gln
            20                  25                  30

Val Ser Gly Ile Gln Asp Ser Asp Tyr Thr Ile Asn Leu Leu Leu Asp
        35                  40                  45

Lys Ala Lys Tyr Glu Lys Gln Ile Lys Ser Asn Tyr Trp Val Glu Ser
    50                  55                  60

Ala Gln Leu Val Tyr Gln Phe Pro Thr Lys Phe Thr Ile Lys Val Lys
65                  70                  75                  80

Glu Tyr Asp Ile Val Ala Tyr Tyr Ile Ser Gly Glu Asn His Tyr Pro
                85                  90                  95

Ile Leu Ser Ser Gly Gln Leu Glu Thr Ser Ser Val Ser Leu Asn Ser
            100                 105                 110

Leu Pro Glu Thr Tyr Leu Ser Val Leu Phe Asn Asp Ser Glu Gln Ile
        115                 120                 125

Lys Val Phe Val Ser Glu Leu Ala Gln Ile Ser Pro Glu Leu Lys Ala
    130                 135                 140

Ala Ile Gln Lys Val Glu Leu Ala Pro Ser Lys Val Thr Ser Asp Leu
145                 150                 155                 160

Ile Arg Leu Thr Met Asn Asp Ser Asp Glu Val Leu Val Pro Leu Ser
                165                 170                 175

Glu Met Ser Lys Lys Leu Pro Tyr Tyr Ser Lys Ile Lys Pro Gln Leu
            180                 185                 190

Ser Glu Pro Ser Val Val Asp Met Glu Ala Gly Ile Tyr Ser Tyr Thr
        195                 200                 205

Val Ala Asp Lys Leu Ile Met Glu Ala Glu Lys Ala Lys Gln Glu
    210                 215                 220

Ala Lys Glu Ala Glu Lys Lys Gln Glu Glu Gln Lys Lys Gln Glu
225                 230                 235                 240
```

```
Glu Glu Ser Asn Arg Asn Gln Thr Thr Gln Arg Ser Arg Arg
            245                 250                 255
```

<210> SEQ ID NO 154
<211> LENGTH: 378
<212> TYPE: PRT
<213> ORGANISM: Streptococcus agalactiae

<400> SEQUENCE: 154

```
Met Pro Lys Lys Ser Asp Thr Pro Glu Lys Glu Val Val Leu
1               5                   10                  15

Thr Glu Trp Gln Lys Arg Asn Leu Glu Phe Leu Lys Arg Lys Glu
            20                  25                  30

Asp Glu Glu Gln Lys Arg Ile Asn Glu Lys Leu Arg Leu Asp Lys
            35                  40                  45

Arg Ser Lys Leu Asn Ile Ser Ser Pro Glu Glu Pro Gln Asn Thr Thr
    50                  55                  60

Lys Ile Lys Lys Leu His Phe Pro Lys Ile Ser Arg Pro Lys Ile Glu
65                  70                  75                  80

Lys Lys Gln Lys Lys Glu Lys Ile Val Asn Ser Leu Ala Lys Thr Asn
                85                  90                  95

Arg Ile Arg Thr Ala Pro Ile Phe Val Val Ala Phe Leu Val Ile Leu
                100                 105                 110

Val Ser Val Phe Leu Leu Thr Pro Phe Ser Lys Gln Lys Thr Ile Thr
                115                 120                 125

Val Ser Gly Asn Gln His Thr Pro Asp Asp Ile Leu Ile Glu Lys Thr
            130                 135                 140

Asn Ile Gln Lys Asn Asp Tyr Phe Phe Ser Leu Ile Phe Lys His Lys
145                 150                 155                 160

Ala Ile Glu Gln Arg Leu Ala Ala Glu Asp Val Trp Val Lys Thr Ala
                165                 170                 175

Gln Met Thr Tyr Gln Phe Pro Asn Lys Phe His Ile Gln Val Gln Glu
            180                 185                 190

Asn Lys Ile Ile Ala Tyr Ala His Thr Lys Gln Gly Tyr Gln Pro Val
        195                 200                 205

Leu Glu Thr Gly Lys Lys Ala Asp Pro Val Asn Ser Ser Glu Leu Pro
    210                 215                 220

Lys His Phe Leu Thr Ile Asn Leu Asp Lys Glu Asp Ser Ile Lys Leu
225                 230                 235                 240

Leu Ile Lys Asp Leu Lys Ala Leu Asp Pro Asp Leu Ile Ser Glu Ile
                245                 250                 255

Gln Val Ile Ser Leu Ala Asp Ser Lys Thr Thr Pro Asp Leu Leu Leu
            260                 265                 270

Leu Asp Met His Asp Gly Asn Ser Ile Arg Ile Pro Leu Ser Lys Phe
        275                 280                 285

Lys Glu Arg Leu Pro Phe Tyr Lys Gln Ile Lys Lys Asn Leu Lys Glu
    290                 295                 300

Pro Ser Ile Val Asp Met Glu Val Gly Val Tyr Thr Thr Thr Asn Thr
305                 310                 315                 320

Ile Glu Ser Thr Pro Val Lys Ala Glu Asp Thr Lys Asn Lys Ser Thr
                325                 330                 335

Asp Lys Thr Gln Thr Gln Asn Gly Gln Val Ala Glu Asn Ser Gln Gly
            340                 345                 350

Gln Thr Asn Asn Ser Asn Thr Asn Gln Gln Gly Gln Gln Ile Ala Thr
        355                 360                 365
```

```
Glu Gln Ala Pro Asn Pro Gln Asn Val Asn
    370                 375

<210> SEQ ID NO 155
<211> LENGTH: 262
<212> TYPE: PRT
<213> ORGANISM: artificial sequence
<220> FEATURE:
<223> OTHER INFORMATION: polypeptide or immunogenic fragment of
      Streptococcus spp genes

<400> SEQUENCE: 155

Leu Leu Thr Pro Phe Ser Lys Gln Lys Thr Ile Thr Val Ser Gly Asn
1               5                   10                  15

Gln His Thr Pro Asp Asp Ile Leu Ile Glu Lys Thr Asn Ile Gln Lys
            20                  25                  30

Asn Asp Tyr Phe Phe Ser Leu Ile Phe Lys His Lys Ala Ile Glu Gln
        35                  40                  45

Arg Leu Ala Ala Glu Asp Val Trp Val Lys Thr Ala Gln Met Thr Tyr
    50                  55                  60

Gln Phe Pro Asn Lys Phe His Ile Gln Val Gln Glu Asn Lys Ile Ile
65                  70                  75                  80

Ala Tyr Ala His Thr Lys Gln Gly Tyr Gln Pro Val Leu Glu Thr Gly
                85                  90                  95

Lys Lys Ala Asp Pro Val Asn Ser Ser Glu Leu Pro Lys His Phe Leu
            100                 105                 110

Thr Ile Asn Leu Asp Lys Glu Asp Ser Ile Lys Leu Leu Ile Lys Asp
        115                 120                 125

Leu Lys Ala Leu Asp Pro Asp Leu Ile Ser Glu Ile Gln Val Ile Ser
    130                 135                 140

Leu Ala Asp Ser Lys Thr Thr Pro Asp Leu Leu Leu Leu Asp Met His
145                 150                 155                 160

Asp Gly Asn Ser Ile Arg Ile Pro Leu Ser Lys Phe Lys Glu Arg Leu
                165                 170                 175

Pro Phe Tyr Lys Gln Ile Lys Lys Asn Leu Lys Glu Pro Ser Ile Val
            180                 185                 190

Asp Met Glu Val Gly Val Tyr Thr Thr Thr Asn Thr Ile Glu Ser Thr
        195                 200                 205

Pro Val Lys Ala Glu Asp Thr Lys Asn Lys Ser Thr Asp Lys Thr Gln
    210                 215                 220

Thr Gln Asn Gly Gln Val Ala Glu Asn Ser Gln Gly Gln Thr Asn Asn
225                 230                 235                 240

Ser Asn Thr Asn Gln Gln Gly Gln Gln Ile Ala Thr Glu Gln Ala Pro
                245                 250                 255

Asn Pro Gln Asn Val Asn
            260

<210> SEQ ID NO 156
<211> LENGTH: 382
<212> TYPE: PRT
<213> ORGANISM: Streptococcus pyogenes

<400> SEQUENCE: 156

Met Ala Lys Asp Lys Glu Lys Gln Ser Asp Asp Lys Leu Val Leu Thr
1               5                   10                  15

Glu Trp Gln Lys Arg Asn Ile Glu Phe Leu Lys Lys Lys Gln Gln
            20                  25                  30
```

```
Ala Glu Glu Glu Lys Lys Leu Lys Glu Lys Leu Leu Ser Asp Lys Lys
         35                  40                  45

Ala Gln Gln Gln Ala Gln Asn Ala Ser Glu Ala Val Glu Leu Lys Thr
     50                  55                  60

Asp Glu Lys Thr Asp Ser Gln Glu Ile Glu Ser Glu Thr Thr Ser Lys
 65                  70                  75                  80

Pro Lys Lys Thr Lys Lys Val Arg Gln Pro Lys Glu Lys Ser Ala Thr
                 85                  90                  95

Gln Ile Ala Phe Gln Lys Ser Leu Pro Val Leu Leu Gly Ala Leu Leu
             100                 105                 110

Leu Met Ala Val Ser Ile Phe Met Ile Thr Pro Tyr Ser Lys Lys Lys
         115                 120                 125

Glu Phe Ser Val Arg Gly Asn His Gln Thr Asn Leu Asp Glu Leu Ile
     130                 135                 140

Lys Ala Ser Lys Val Lys Ala Ser Asp Tyr Trp Leu Thr Leu Leu Ile
145                 150                 155                 160

Ser Pro Gly Gln Tyr Glu Arg Pro Ile Leu Arg Thr Ile Pro Trp Val
                165                 170                 175

Lys Ser Val His Leu Ser Tyr Gln Phe Pro Asn His Phe Leu Phe Asn
             180                 185                 190

Val Ile Glu Phe Glu Ile Ile Ala Tyr Ala Gln Val Glu Asn Gly Phe
         195                 200                 205

Gln Pro Ile Leu Glu Asn Gly Lys Arg Val Asp Lys Val Arg Ala Ser
     210                 215                 220

Glu Leu Pro Lys Ser Phe Leu Ile Leu Asn Leu Lys Asp Glu Lys Ala
225                 230                 235                 240

Ile Gln Gln Leu Val Lys Gln Leu Thr Thr Leu Pro Lys Lys Leu Val
                245                 250                 255

Lys Asn Ile Lys Ser Val Ser Leu Ala Asn Ser Lys Thr Thr Ala Asp
             260                 265                 270

Leu Leu Leu Ile Glu Met His Asp Gly Asn Val Val Arg Val Pro Gln
         275                 280                 285

Ser Gln Leu Thr Leu Lys Leu Pro Tyr Tyr Gln Lys Leu Lys Lys Asn
     290                 295                 300

Leu Glu Asn Asp Ser Ile Val Asp Met Glu Val Gly Ile Tyr Thr Thr
305                 310                 315                 320

Thr Gln Glu Ile Glu Asn Gln Pro Glu Val Pro Leu Thr Pro Glu Gln
                325                 330                 335

Asn Ala Ala Asp Lys Glu Gly Asp Lys Pro Gly Glu His Gln Glu Gln
             340                 345                 350

Thr Asp Asn Asp Ser Glu Thr Pro Ala Asn Gln Ser Ser Pro Gln Gln
         355                 360                 365

Ala Pro Pro Ser Pro Glu Thr Val Leu Glu Gln Ala His Gly
     370                 375                 380

<210> SEQ ID NO 157
<211> LENGTH: 265
<212> TYPE: PRT
<213> ORGANISM: artificial sequence
<220> FEATURE:
<223> OTHER INFORMATION: polypeptide or immunogenic fragment of
      Streptococcus spp genes

<400> SEQUENCE: 157

Ile Phe Met Ile Thr Pro Tyr Ser Lys Lys Lys Glu Phe Ser Val Arg
```

```
1               5                  10                 15
Gly Asn His Gln Thr Asn Leu Asp Glu Leu Ile Lys Ala Ser Lys Val
            20                  25                  30

Lys Ala Ser Asp Tyr Trp Leu Thr Leu Ile Ser Pro Gly Gln Tyr
            35                  40                  45

Glu Arg Pro Ile Leu Arg Thr Ile Pro Trp Val Lys Ser Val His Leu
50                  55                  60

Ser Tyr Gln Phe Pro Asn His Phe Leu Phe Asn Val Ile Glu Phe Glu
65                  70                  75                  80

Ile Ile Ala Tyr Ala Gln Val Glu Asn Gly Phe Gln Pro Ile Leu Glu
            85                  90                  95

Asn Gly Lys Arg Val Asp Lys Val Arg Ala Ser Glu Leu Pro Lys Ser
            100                 105                 110

Phe Leu Ile Leu Asn Leu Lys Asp Glu Lys Ala Ile Gln Gln Leu Val
            115                 120                 125

Lys Gln Leu Thr Thr Leu Pro Lys Lys Leu Val Lys Asn Ile Lys Ser
            130                 135                 140

Val Ser Leu Ala Asn Ser Lys Thr Thr Ala Asp Leu Leu Leu Ile Glu
145                 150                 155                 160

Met His Asp Gly Asn Val Val Arg Val Pro Gln Ser Gln Leu Thr Leu
                165                 170                 175

Lys Leu Pro Tyr Tyr Gln Lys Leu Lys Lys Asn Leu Glu Asn Asp Ser
            180                 185                 190

Ile Val Asp Met Glu Val Gly Ile Tyr Thr Thr Thr Gln Glu Ile Glu
            195                 200                 205

Asn Gln Pro Glu Val Pro Leu Thr Pro Glu Gln Asn Ala Ala Asp Lys
            210                 215                 220

Glu Gly Asp Lys Pro Gly Glu His Gln Glu Gln Thr Asp Asn Asp Ser
225                 230                 235                 240

Glu Thr Pro Ala Asn Gln Ser Ser Pro Gln Gln Ala Pro Pro Ser Pro
            245                 250                 255

Glu Thr Val Leu Glu Gln Ala His Gly
            260                 265

<210> SEQ ID NO 158
<211> LENGTH: 119
<212> TYPE: PRT
<213> ORGANISM: Bacillus anthracis

<400> SEQUENCE: 158

Met Arg Glu Leu Arg Gln Arg Thr Ile Glu Lys Gln Ser Pro Asn Pro
1               5                   10                  15

Val Lys Glu His Ile Ile Gln Thr Asp Glu Asn Arg Lys Arg Leu Tyr
            20                  25                  30

Arg Arg Leu Ala Val Phe Leu Val Phe Ala Phe Thr Ile Ile Ala Ser
            35                  40                  45

Ile Ser Val Thr Phe Tyr Gln Gln Asn Ser Ser Ile Lys Ala Lys Glu
50                  55                  60

Ala Lys Val Lys Asp Met Lys Lys Glu Leu Asp Ser Leu Thr Asn Lys
65                  70                  75                  80

Glu Lys Ser Leu Lys Asp Glu Val Gln Lys Leu Asn Asp Glu Glu Tyr
            85                  90                  95

Val Leu Lys Ile Ala Arg Arg Asp Tyr Phe Phe Ser Gly Lys Gly Glu
            100                 105                 110
```

```
Ile Ile Phe Pro Val Ser Lys
            115

<210> SEQ ID NO 159
<211> LENGTH: 68
<212> TYPE: PRT
<213> ORGANISM: artificial sequence
<220> FEATURE:
<223> OTHER INFORMATION: polypeptide or immunogenic fragment of Bacillus
      spp genes

<400> SEQUENCE: 159

Thr Phe Tyr Gln Gln Asn Ser Ser Ile Lys Ala Lys Glu Ala Lys Val
1               5                   10                  15

Lys Asp Met Lys Lys Glu Leu Asp Ser Leu Thr Asn Lys Glu Lys Ser
            20                  25                  30

Leu Lys Asp Glu Val Gln Lys Leu Asn Asp Glu Glu Tyr Val Leu Lys
        35                  40                  45

Ile Ala Arg Arg Asp Tyr Phe Phe Ser Gly Lys Gly Glu Ile Ile Phe
    50                  55                  60

Pro Val Ser Lys
65

<210> SEQ ID NO 160
<211> LENGTH: 89
<212> TYPE: PRT
<213> ORGANISM: Clostridium botulinum A

<400> SEQUENCE: 160

Met Lys Lys Ile Asn Val Lys Lys Leu Ile Phe Phe Leu Ala Ile Val
1               5                   10                  15

Tyr Ser Thr Val Ile Phe Ile Asn Gln Gln Ile Thr Met His Lys Ile
            20                  25                  30

Arg Asp Gln Ile Ser Glu Lys Lys Ile Glu Leu Lys Glu Val Lys Glu
        35                  40                  45

Lys Asn Gln Lys Leu Gln Asp Glu Val Lys Leu Ser Lys Ser Lys Asp
    50                  55                  60

Tyr Ile Glu Lys Leu Ala Arg Glu Arg Leu Arg Leu Ile Lys Lys Gly
65                  70                  75                  80

Glu Thr Pro Val Ile Asn Asn Thr Gln
                85

<210> SEQ ID NO 161
<211> LENGTH: 63
<212> TYPE: PRT
<213> ORGANISM: artificial sequence
<220> FEATURE:
<223> OTHER INFORMATION: polypeptide or immunogenic fragment of
      Clostridium spp genes

<400> SEQUENCE: 161

Ile Thr Met His Lys Ile Arg Asp Gln Ile Ser Glu Lys Lys Ile Glu
1               5                   10                  15

Leu Lys Glu Val Lys Glu Lys Asn Gln Lys Leu Gln Asp Glu Val Lys
            20                  25                  30

Leu Ser Lys Ser Lys Asp Tyr Ile Glu Lys Leu Ala Arg Glu Arg Leu
        35                  40                  45

Arg Leu Ile Lys Lys Gly Glu Thr Pro Val Ile Asn Asn Thr Gln
    50                  55                  60
```

```
<210> SEQ ID NO 162
<211> LENGTH: 159
<212> TYPE: PRT
<213> ORGANISM: Enterococcus faecalis

<400> SEQUENCE: 162

Met Gly Lys Asn Glu Lys Ser Ser Lys Val Ala Ala Leu Glu Asn
1               5                   10                  15

Asp Tyr Thr Lys Glu Gln Tyr Val Glu Phe Gln Lys Gln Lys Gln
            20                  25                  30

Leu Ile Phe Arg Arg Arg Leu Ala Ala Ile Phe Leu Val Ala Phe
        35                  40                  45

Ile Ile Phe Ala Phe Ser Gly Ile Gln Leu Met Lys Asp Tyr His Arg
    50                  55                  60

Leu Gly Ala Phe Lys Gln Glu Arg Ala Asp Ala Ile Ala Glu Ser Val
65                  70                  75                  80

Ala Val Asp Lys Lys Val Lys Asp Leu Lys Lys Asp Val Ala Leu Leu
                85                  90                  95

Lys Asp Asp Asp Tyr Val Ala Lys Leu Ala Arg Ser Arg Phe Leu Leu
                100                 105                 110

Ser Lys Glu Gly Glu Gln Ile Tyr Pro Thr Pro Glu Gln Met Lys Lys
            115                 120                 125

Thr Gln Thr Ser Gly Ala Glu Glu Ser Lys Ser Ser Ser Glu Lys Asn
130                 135                 140

Ser Gln Ser Gln Ser Ser Thr Glu Thr Thr Lys Ser Ser Ala Glu
145                 150                 155

<210> SEQ ID NO 163
<211> LENGTH: 103
<212> TYPE: PRT
<213> ORGANISM: artificial sequence
<220> FEATURE:
<223> OTHER INFORMATION: polypeptide or immunogenic fragment of
      Enetrococcus spp genes

<400> SEQUENCE: 163

Gln Leu Met Lys Asp Tyr His Arg Leu Gly Ala Phe Lys Gln Glu Arg
1               5                   10                  15

Ala Asp Ala Ile Ala Glu Ser Val Ala Val Asp Lys Lys Val Lys Asp
            20                  25                  30

Leu Lys Lys Asp Val Ala Leu Leu Lys Asp Asp Asp Tyr Val Ala Lys
        35                  40                  45

Leu Ala Arg Ser Arg Phe Leu Leu Ser Lys Glu Gly Glu Gln Ile Tyr
    50                  55                  60

Pro Thr Pro Glu Gln Met Lys Lys Thr Gln Thr Ser Gly Ala Glu Glu
65                  70                  75                  80

Ser Lys Ser Ser Ser Glu Lys Asn Ser Gln Ser Gln Ser Ser Thr Glu
                85                  90                  95

Thr Thr Lys Ser Ser Ala Glu
            100

<210> SEQ ID NO 164
<211> LENGTH: 123
<212> TYPE: PRT
<213> ORGANISM: Streptococcus agalactiae

<400> SEQUENCE: 164

Met Ser Lys Pro Asn Val Val Gln Leu Asn Asn Gln Tyr Ile Asn Asp
1               5                   10                  15
```

```
Glu Asn Leu Lys Lys Arg Tyr Glu Ala Glu Leu Arg Arg Lys Asn
             20                  25                  30

Arg Leu Met Gly Trp Val Leu Ile Phe Val Met Leu Leu Phe Ile Leu
         35                  40                  45

Pro Thr Tyr Asn Leu Val Lys Ser Tyr Arg Thr Leu Gln Glu Arg Arg
     50                  55                  60

Gln Glu Val Val Lys Leu Thr Lys Asp Tyr Gln Thr Leu Thr Asn Arg
 65                  70                  75                  80

Thr Glu Asn Gln Lys Leu Leu Ala Lys Gln Leu Lys Asn Pro Asp Tyr
                 85                  90                  95

Val Gln Lys Tyr Ala Arg Ala Lys Tyr Tyr Phe Ser Lys Thr Gly Glu
            100                 105                 110

Met Ile Tyr Pro Leu Pro Asp Leu Leu Pro Lys
            115                 120
```

<210> SEQ ID NO 165
<211> LENGTH: 72
<212> TYPE: PRT
<213> ORGANISM: artificial sequence
<220> FEATURE:
<223> OTHER INFORMATION: polypeptide or immunogenic fragment of
      Streptococcus spp genes

<400> SEQUENCE: 165

```
Asn Leu Val Lys Ser Tyr Arg Thr Leu Gln Glu Arg Arg Gln Glu Val
 1               5                  10                  15

Val Lys Leu Thr Lys Asp Tyr Gln Thr Leu Thr Asn Arg Thr Glu Asn
             20                  25                  30

Gln Lys Leu Leu Ala Lys Gln Leu Lys Asn Pro Asp Tyr Val Gln Lys
         35                  40                  45

Tyr Ala Arg Ala Lys Tyr Tyr Phe Ser Lys Thr Gly Glu Met Ile Tyr
     50                  55                  60

Pro Leu Pro Asp Leu Leu Pro Lys
 65                  70
```

<210> SEQ ID NO 166
<211> LENGTH: 123
<212> TYPE: PRT
<213> ORGANISM: Streptococcus pyogenes M1

<400> SEQUENCE: 166

```
Met Lys Lys Pro Ser Ile Val Gln Leu Asn Asn His Tyr Ile Lys Lys
 1               5                  10                  15

Glu Asn Leu Lys Lys Lys Phe Glu Glu Glu Ser Gln Lys Arg Asn
             20                  25                  30

Arg Phe Met Gly Trp Ile Leu Val Ser Met Met Phe Leu Phe Ile Leu
         35                  40                  45

Pro Thr Tyr Asn Leu Val Lys Ser Tyr Val Asp Phe Glu Lys Gln Asn
     50                  55                  60

Gln Gln Val Val Lys Leu Lys Lys Glu Tyr Asn Glu Leu Ser Glu Ser
 65                  70                  75                  80

Thr Lys Lys Glu Lys Gln Leu Ala Glu Arg Leu Lys Asp Asp Asn Phe
                 85                  90                  95

Val Lys Lys Tyr Ala Arg Ala Lys Tyr Tyr Leu Ser Arg Glu Gly Glu
            100                 105                 110

Met Ile Tyr Pro Ile Pro Gly Leu Leu Pro Lys
            115                 120
```

<210> SEQ ID NO 167
<211> LENGTH: 69
<212> TYPE: PRT
<213> ORGANISM: artificial sequence
<220> FEATURE:
<223> OTHER INFORMATION: polypeptide or immunogenic fragment of
      Streptococcus spp genes

<400> SEQUENCE: 167

Asn Leu Val Lys Ser Tyr Val Asp Phe Glu Lys Gln Asn Gln Gln Val
1               5                   10                  15

Val Lys Leu Lys Lys Glu Tyr Asn Glu Leu Ser Glu Ser Thr Lys Lys
            20                  25                  30

Glu Lys Gln Leu Ala Glu Arg Leu Lys Asp Asp Asn Phe Val Lys Lys
        35                  40                  45

Tyr Ala Arg Ala Lys Tyr Tyr Leu Ser Arg Glu Gly Glu Met Ile Tyr
    50                  55                  60

Pro Ile Pro Gly Leu
65

<210> SEQ ID NO 168
<211> LENGTH: 120
<212> TYPE: PRT
<213> ORGANISM: Bacillus anthracis

<400> SEQUENCE: 168

Met Ser Asn Leu Ala Val Lys Tyr Lys Gln Gln Ala Gln Glu Glu Val
1               5                   10                  15

Gln Ile Gln Thr Pro Pro Gln Met Val Gln Pro Lys Ala Lys Ala
            20                  25                  30

Lys Ile Thr Arg Ile Glu Lys Leu Leu Tyr Val Ala Phe Ile Gly Phe
        35                  40                  45

Leu Leu Tyr Ala Cys Val Ala Phe Ile Gly Asn Lys Ala Gly Leu Tyr
    50                  55                  60

Gln Val Asn Val Glu Ala Ala Thr Ile Glu Gly Lys Ile Val Gln Gln
65                  70                  75                  80

Gln Lys Glu Asn Gln Glu Leu Gln Ala Glu Val Glu Lys Leu Ser Arg
                85                  90                  95

Tyr Glu Arg Ile Ala Glu Val Ala Lys Lys His Gly Leu Glu Ile Asn
                100                 105                 110

Ala Asn Asn Val Lys Gly Leu Lys
        115                 120

<210> SEQ ID NO 169
<211> LENGTH: 65
<212> TYPE: PRT
<213> ORGANISM: artificial sequence
<220> FEATURE:
<223> OTHER INFORMATION: polypeptide or immunogenic fragment of Bacillus
      spp genes

<400> SEQUENCE: 169

Phe Ile Gly Asn Lys Ala Gly Leu Tyr Gln Val Asn Val Glu Ala Ala
1               5                   10                  15

Thr Ile Glu Gln Lys Ile Val Gln Gln Gln Lys Glu Asn Gln Glu Leu
            20                  25                  30

Gln Ala Glu Val Glu Lys Leu Ser Arg Tyr Glu Arg Ile Ala Glu Val
        35                  40                  45

Ala Lys Lys His Gly Leu Glu Ile Asn Ala Asn Asn Val Lys Gly Leu
         50                  55                  60

Lys
65

<210> SEQ ID NO 170
<211> LENGTH: 135
<212> TYPE: PRT
<213> ORGANISM: Enterococcus faecalis

<400> SEQUENCE: 170

Met Ala Glu Leu Lys Lys Val Asn Asp Phe His Tyr Glu Ala Pro Glu
1               5                  10                  15

Met Asp Gln Pro Thr Val Ala Thr Glu Gln Asp Arg Lys Met Gln Glu
            20                  25                  30

Glu Thr Leu Pro Val Pro Thr Ile Leu Pro Lys Lys Leu Lys Asn
        35                  40                  45

Val Ser Leu Leu Glu Lys Leu Ile Gly Val Val Leu Val Cys Ala Thr
    50                  55                  60

Ile Gly Ile Ala Ile Ala Thr Ile Gln Val Arg Thr Thr Ile Val Gln
65                  70                  75                  80

Thr Met Asn Asp Ile Thr Glu Thr Gln Ala Val Ile Lys Glu Lys Glu
                85                  90                  95

Asp Asn Ala Leu Lys Leu Glu Gln Glu Arg Ser Glu Leu Ser Lys Ser
            100                 105                 110

Asp Arg Ile Lys Asp Val Ala Lys Lys Gln Gly Leu Glu Asn Asn Gly
        115                 120                 125

Asp Asn Val Arg Thr Val Lys
    130                 135

<210> SEQ ID NO 171
<211> LENGTH: 67
<212> TYPE: PRT
<213> ORGANISM: artificial sequence
<220> FEATURE:
<223> OTHER INFORMATION: polypeptide or immunogenic fragment of
      Enetrococcus spp genes

<400> SEQUENCE: 171

Ile Ala Thr Ile Gln Val Arg Thr Thr Ile Val Gln Thr Met Asn Asp
1               5                  10                  15

Ile Thr Glu Thr Gln Ala Val Ile Lys Glu Lys Glu Asp Asn Ala Leu
            20                  25                  30

Lys Leu Glu Gln Glu Arg Ser Glu Leu Ser Lys Ser Asp Arg Ile Lys
        35                  40                  45

Asp Val Ala Lys Lys Gln Gly Leu Glu Asn Asn Gly Asp Asn Val Arg
    50                  55                  60

Thr Val Lys
65

<210> SEQ ID NO 172
<211> LENGTH: 108
<212> TYPE: PRT
<213> ORGANISM: Streptococcus agalactiae

<400> SEQUENCE: 172

Met Thr Asn Glu Lys Arg Thr Glu Ala Val Thr Gln Thr Leu Gln Arg
1               5                  10                  15

His Ile Lys Thr Phe Ser Arg Ile Glu Lys Ala Phe Tyr Gly Ala Ile

```
                    20                  25                  30
Val Ile Thr Ala Ile Ile Met Ala Val Gly Ile Ile Tyr Leu Gln Ser
                35                  40                  45

Asn Ser Leu Gln Val Lys Gln Glu Val Asn Gln Leu Asn Ser Lys Ile
        50                  55                  60

Asn Asp Lys Gln Thr Glu Phe Asp Asn Ala Lys Gln Glu Val Asn Glu
65                  70                  75                  80

Leu Ser Asn Arg Asp Arg Ile Thr Lys Ile Ala Lys Asp Ala Gly Leu
                85                  90                  95

Thr Ile Gln Asn Asp Asn Ile Tyr Arg Lys Val Asp
            100                 105
```

<210> SEQ ID NO 173
<211> LENGTH: 67
<212> TYPE: PRT
<213> ORGANISM: artificial sequence
<220> FEATURE:
<223> OTHER INFORMATION: polypeptide or immunogenic fragment of
      Streptococcus spp genes

<400> SEQUENCE: 173

```
Gly Ile Ile Tyr Leu Gln Ser Asn Ser Leu Gln Val Lys Gln Glu Val
1               5                   10                  15

Asn Gln Leu Asn Ser Lys Ile Asn Asp Lys Gln Thr Glu Phe Asp Asn
            20                  25                  30

Ala Lys Gln Glu Val Asn Glu Leu Ser Asn Arg Asp Arg Ile Thr Lys
        35                  40                  45

Ile Ala Lys Asp Ala Gly Leu Thr Ile Gln Asn Asp Asn Ile Tyr Arg
    50                  55                  60

Lys Val Asp
65
```

<210> SEQ ID NO 174
<211> LENGTH: 105
<212> TYPE: PRT
<213> ORGANISM: Streptococcus pneumoniae

<400> SEQUENCE: 174

```
Met Ala Glu Arg Met Glu Lys Thr Gly Gln Ile Leu Gln Met Gln Leu
1               5                   10                  15

Lys Arg Phe Ser Arg Val Glu Lys Ala Phe Tyr Phe Ser Ile Ala Val
            20                  25                  30

Thr Thr Leu Ile Val Ala Ile Ser Ile Ile Phe Met Gln Thr Lys Leu
        35                  40                  45

Leu Gln Val Gln Asn Asp Leu Thr Lys Ile Asn Ala Gln Ile Glu Glu
    50                  55                  60

Lys Lys Thr Glu Leu Asp Asp Ala Lys Gln Glu Val Asn Glu Leu Leu
65                  70                  75                  80

Arg Ala Glu Arg Leu Lys Glu Ile Ala Asn Ser His Asp Leu Gln Leu
                85                  90                  95

Asn Asn Glu Asn Ile Arg Ile Ala Glu
            100                 105
```

<210> SEQ ID NO 175
<211> LENGTH: 63
<212> TYPE: PRT
<213> ORGANISM: artificial sequence
<220> FEATURE:
<223> OTHER INFORMATION: polypeptide or immunogenic fragment of Streptococcus spp genes

<400> SEQUENCE: 175

Phe Met Gln Thr Lys Leu Leu Gln Val Gln Asn Asp Leu Thr Lys Ile
1               5                   10                  15

Asn Ala Gln Ile Glu Glu Lys Lys Thr Glu Leu Asp Asp Ala Lys Gln
            20                  25                  30

Glu Val Asn Glu Leu Leu Arg Ala Glu Arg Leu Lys Glu Ile Ala Asn
        35                  40                  45

Ser His Asp Leu Gln Leu Asn Asn Glu Asn Ile Arg Ile Ala Glu
    50                  55                  60

<210> SEQ ID NO 176
<211> LENGTH: 117
<212> TYPE: PRT
<213> ORGANISM: Streptococcus pyogenes

<400> SEQUENCE: 176

Met Leu Pro Lys Lys Phe Gly Asn Lys Pro Met Thr Asn Glu Lys Arg
1               5                   10                  15

Thr Gln Ala Val Thr Asn Ala Leu Gln Lys Arg Ile Lys Thr Phe Ser
            20                  25                  30

Arg Ile Glu Lys Ala Phe Tyr Thr Ala Ile Ile Val Thr Ala Ile Thr
        35                  40                  45

Met Ala Val Ser Ile Ile Tyr Leu Gln Ser Arg Lys Leu Gln Leu Gln
    50                  55                  60

Gln Glu Ile Thr Ser Leu Asn Ser His Ile Ser Asp Gln Lys Leu Glu
65                  70                  75                  80

Leu Asn Asn Ala Lys Gln Glu Val Asn Glu Leu Ser Arg Arg Asp Arg
                85                  90                  95

Ile Ile Asp Ile Ala Gly Lys Ala Gly Leu Ser Asn Arg Asn Asn Asn
            100                 105                 110

Ile Lys Lys Val Glu
        115

<210> SEQ ID NO 177
<211> LENGTH: 64
<212> TYPE: PRT
<213> ORGANISM: artificial sequence
<220> FEATURE:
<223> OTHER INFORMATION: polypeptide or immunogenic fragment of
      Streptococcus spp genes

<400> SEQUENCE: 177

Ile Tyr Leu Gln Ser Arg Lys Leu Gln Leu Gln Gln Glu Ile Thr Ser
1               5                   10                  15

Leu Asn Ser His Ile Ser Asp Gln Lys Leu Glu Leu Asn Asn Ala Lys
            20                  25                  30

Gln Glu Val Asn Glu Leu Ser Arg Arg Asp Arg Ile Ile Asp Ile Ala
        35                  40                  45

Gly Lys Ala Gly Leu Ser Asn Arg Asn Asn Asn Ile Lys Lys Val Glu
    50                  55                  60

BACTERIAL VACCINE

REFERENCE TO RELATED APPLICATIONS

This application is a US national phase entry of International Patent Application No. PCT/GB2013/050910, filed Apr. 9, 2013, which claims priority to GB Patent Application No. 1206366.5, filed Apr. 11, 2012.

FIELD OF THE INVENTION

The disclosure relates to a composition comprising one, two, or more immunogenic bacterial polypeptides and a vaccine composition, typically a multivalent vaccine, comprising the immunogenic bacterial polypeptides in the prevention or treatment of bacterial infections in humans and animals.

BACKGROUND TO THE INVENTION

Vaccines protect against a wide variety of infectious diseases. Many modern vaccines are therefore made from protective antigens of the pathogen, which are isolated by molecular cloning and purified. These vaccines are known as 'subunit vaccines'. The development of subunit vaccines has been the focus of considerable research in recent years. The emergence of new pathogens and the growth of antibiotic resistance have created a need to develop new vaccines and to identify further candidate molecules useful in the development of subunit vaccines. Likewise the discovery of novel vaccine antigens from genomic and proteomic studies is enabling the development of new subunit vaccine candidates, particularly against bacterial pathogens. However, although subunit vaccines tend to avoid the side effects of killed or attenuated pathogen vaccines, their 'pure' status means that subunit vaccines do not always have adequate immunogenicity to confer protection.

An approach to improve the efficacy of vaccine compositions is to provide multivalent vaccines comprising dominant antigens that provoke both a B cell and T cell response thereby mounting a more rigorous immune response in the subject receiving the vaccine. A typical multivalent vaccine might be a whole cell vaccine comprising multiple antigenic molecules. For example the *Bacillus* Calmette Guerin ["BCG"] vaccine includes an attenuated *Mycobacterium bovis* strain that provokes protective immunity in humans. For many pathogens chemical or heat inactivation while it may give rise to vaccine immunogens that confer protective immunity also gives rise to side effects such as fever and injection site reactions. In the case of bacteria, inactivated organisms tend to be so toxic that side effects have limited the application of such crude vaccine immunogens and therefore vaccine development has lagged behind drug-development. Moreover, effective vaccine development using whole cell inactivated organisms suffers from problems of epitope masking, immunodominance, low antigen concentration and antigen redundancy.

There is therefore a continuing need to identify antigens that are protective and can be used in multivalent vaccines of bacterial pathogens. The combinations may be used in combination with non-protein immunogenic molecules such as polysaccharide antigens and anti-bacterial agents to provide a treatment regimen for control of bacterial infection. It is also within the scope of this disclosure to modify the treatment regimen to immunize subjects with a series of temporally separated administrations as an alternative to the administration of a single vaccine comprising multiple antigens.

This disclosure therefore relates to immunogenic compositions and vaccines, typically multivalent vaccines but also monovalent vaccines and their use in the prophylaxis and treatment of bacterial infections. We disclose polypeptides that are typically membrane spanning proteins that include an extracellular domain. For example DivIB is an integral membrane protein comprising an intracellular domain, an intermembrane domain and an extracellular domain. The related gene DivIC is also an integral membrane protein the extracellular domain. This disclosure also relates to antigens encoded by the genes PheP, YdiE and FtsL each of which has an extramembranous domain. Typically, it would be desirable to develop vaccines against Gram positive bacterial pathogens which include, by example: *Bacillus anthracis, Clostridium botulinum, Clostridium difficile, Enterococcus faecalis, Mycobacterium tuberculosis, Staphylococcus* spp, *Streptococcus* group A, *Streptococcus* group B, *Streptococcus pneumonia*. Moreover the development of vaccines against Gram negative bacterial pathogens such as, *Helicobacter pylori, Neisseria gonorrhoea, Neisseria meningitidis* type B, *Shigella flexneri, Escherichia coli, Haemophilus influenzae, Chlamydia trachomatis, Pseudomonas aeruginosa, Yersinia pestis, Burkholderia mallei* or *B. pseudomallei* would also be desirable.

STATEMENTS OF INVENTION

According to an aspect of the invention there is provided an immunogenic composition comprising two or more different polypeptides wherein said polypeptides are encoded by different *Bacillus* spp genes selected from the group consisting of:

i) a polypeptide, or immunogenic fragment thereof, comprising or consisting of the amino acid sequence as represented in SEQ ID NO: 1, 2, 3, 4, 5, 6 or 7; or ii) a polypeptide, or immunogenic fragment thereof, comprising or consisting of the amino acid sequence as represented in SEQ ID NO: 112; or i) a polypeptide, or immunogenic fragment thereof, comprising or consisting of the amino acid sequence as represented in SEQ ID NO: 144 or 145; or ii) a polypeptide, or immunogenic fragment thereof, comprising or consisting of the amino acid sequence as represented in SEQ ID NO: 158 or 159; or iii) a polypeptide, or immunogenic fragment thereof, comprising or consisting of the amino acid sequence as represented in SEQ ID NO: 168 or 169; or iv) a modified polypeptide wherein said polypeptide is a polypeptide variant of the amino acid sequences presented in SEQ ID NO: 1, 2, 3, 4, 5, 6, 7, 112, 144, 145, 158, 159, 168 or 169, wherein said sequences are modified by addition, deletion or substitution of one or more amino acid residues which modified polypeptides have retained or enhanced immunogenicity when compared to the polypeptide as represented in SEQ ID NO: 1, 2, 3, 4, 5, 6, 7, 112, 144, 145, 158, 159, 168 or 169.

A modified polypeptide or variant polypeptide may differ in amino acid sequence by one or more substitutions, additions, deletions, truncations that may be present in any combination. Among preferred variants are those that vary from a reference polypeptide by conservative amino acid substitutions. Such substitutions are those that substitute a given amino acid by another amino acid of like characteristics. The following non-limiting list of amino acids are considered conservative replacements (similar): a) alanine, serine, and threonine; b) glutamic acid and aspartic acid; c) asparagine and glutamine d) arginine and lysine; e) isoleucine, leucine, methionine and valine and f) phenylalanine, tyrosine and tryptophan. Most highly preferred are variants that retain or enhance the immunogenecity and/or activity as the reference polypeptide from which it varies.

In one embodiment, the variant polypeptides have at least 80-89% sequence identity, more preferably at least 90% identity, even more preferably at least 95% identity, still more preferably at least 97% identity, and most preferably at least 99% identity with the full length amino acid sequences illustrated herein.

According to an aspect of the invention there is provided an immunogenic composition comprising two or more different polypeptides wherein said polypeptides are encoded by different *Bukholderia* spp genes selected from the group consisting of:
  i) a polypeptide, or immunogenic fragment thereof, comprising or consisting of the amino acid sequence as represented in SEQ ID NO: 8, 9, 10, 11, 12, 13 or 14; or
  ii) a polypeptide, or immunogenic fragment thereof, comprising or consisting of the amino acid sequence as represented in SEQ ID NO: 113 or 114; or
  iii) a modified polypeptide wherein said polypeptide is a polypeptide variant of the amino acid sequences presented in SEQ ID NO: 8, 9, 10, 11, 12, 13, 14 or 113 wherein said sequences are modified by addition, deletion or substitution of one or more amino acid residues which modified polypeptides have retained or enhanced immunogenicity when compared to the polypeptide as represented in SEQ ID NO: 8, 9, 10, 11, 12, 13, 14, 113 or 114.

According to an aspect of the invention there is provided an immunogenic composition comprising two or more different polypeptides wherein said polypeptides are encoded by different *Bukholderia* spp genes selected from the group consisting of:
  i) a polypeptide, or immunogenic fragment thereof, comprising or consisting of the amino acid sequence as represented in SEQ ID NO: 15, 16, 17, 18, 19, 20 or 21; or
  iii) a polypeptide, or immunogenic fragment thereof, comprising or consisting of the amino acid sequence as represented in SEQ ID NO: 115 or 116; or
  iv) a modified polypeptide wherein said polypeptide is a polypeptide variant of the amino acid sequences presented in SEQ ID NO: 15, 16, 17, 18, 19, 20, 21, 115 or 116; wherein said sequences are modified by addition, deletion or substitution of one or more amino acid residues which modified polypeptides have retained or enhanced immunogenicity when compared to the polypeptide as represented in SEQ ID NO: 15, 16, 17, 18, 19, 20, 21, 115 or 116.

According to an aspect of the invention there is provided an immunogenic composition comprising two or more different polypeptides wherein said polypeptides are encoded by different *Clostridium* spp genes selected from the group consisting of:
  i) a polypeptide, or immunogenic fragment thereof, comprising or consisting of the amino acid sequence as represented in SEQ ID NO: 22, 23, 24, 25, 26, 27 or 28; or
  ii) a polypeptide, or immunogenic fragment thereof, comprising or consisting of the amino acid sequence as represented in SEQ ID NO: 118; or
  iii) a polypeptide, or immunogenic fragment thereof, comprising or consisting of the amino acid sequence as represented in SEQ ID NO:146 or 147; or
  iv) a polypeptide, or immunogenic fragment thereof, comprising or consisting of the amino acid sequence as represented in SEQ ID NO:160 or 161; or
  v) a modified polypeptide wherein said polypeptide is a polypeptide variant of the amino acid sequences presented in SEQ ID NO: 22, 23, 24, 25, 26, 27, 28, 118, 146, 147, 160 or 161 wherein said sequences are modified by addition, deletion or substitution of one or more amino acid residues which modified polypeptides have retained or enhanced immunogenicity when compared to the polypeptide as represented in SEQ ID NO: 22, 23, 24, 25, 26, 27, 28, 118, 146, 147, 160 or 161.

According to an aspect of the invention there is provided an immunogenic composition comprising two or more different polypeptides wherein said polypeptides are encoded by different *Clostridium* spp genes selected from the group consisting of
  i) a polypeptide, or immunogenic fragment thereof, comprising or consisting of the amino acid sequence as represented in SEQ ID NO: 29, 30, 31, 32, 33, 34 or 35; or
  ii) a polypeptide, or immunogenic fragment thereof, comprising or consisting of the amino acid sequence as represented in SEQ ID NO: 119; or
  iii) a polypeptide, or immunogenic fragment thereof, comprising or consisting of the amino acid sequence as represented in SEQ ID NO:148 or 149; or
  iv) a modified polypeptide wherein said polypeptide is a polypeptide variant of the amino acid sequences presented in SEQ ID NO: 29, 30, 31, 32, 33, 34, 35, 119, 148 or 149; wherein said sequences are modified by addition, deletion or substitution of one or more amino acid residues which modified polypeptides have retained or enhanced immunogenicity when compared to the polypeptide as represented in SEQ ID NO: 29, 30, 31, 32, 33, 34, 35, 119, 148 or 149.

According to an aspect of the invention there is provided an immunogenic composition comprising two or more different polypeptides wherein said polypeptides are encoded by different *Enterococcus* spp genes selected from the group consisting of
  i) a polypeptide, or immunogenic fragment thereof, comprising or consisting of the amino acid sequence as represented in SEQ ID NO: 36, 37, 38, 39, 40, 41 or 42;
  ii) a polypeptide, or immunogenic fragment thereof, comprising or consisting of the amino acid sequence as represented in SEQ ID NO: 120 or 121; or
  iii) a polypeptide, or immunogenic fragment thereof, comprising or consisting of the amino acid sequence as represented in SEQ ID NO: 150 or 151; or
  iv) a polypeptide, or immunogenic fragment thereof, comprising or consisting of the amino acid sequence as represented in SEQ ID NO:162 or 163; or
  v) a polypeptide, or immunogenic fragment thereof, comprising or consisting of the amino acid sequence as represented in SEQ ID NO:170 or 171; or
  vi) a modified polypeptide wherein said polypeptide is a polypeptide variant of the amino acid sequences presented in SEQ ID NO: 36, 37, 38, 39, 40, 41, 42, 120, 121, 150, 151, 162, 163, 170 or 171; wherein said sequences are modified by addition, deletion or substitution of one or more amino acid residues which modified polypeptides have retained or enhanced immunogenicity when compared to the polypeptide as represented in SEQ ID NO: 36, 37, 38, 39, 40, 41, 42, 120, 121, 150, 151, 162, 163, 170 or 171.

According to an aspect of the invention there is provided an immunogenic composition comprising two or more different polypeptides wherein said polypeptides are encoded by different *Escherchia* spp genes selected from the group consisting of:
  i) a polypeptide, or immunogenic fragment thereof, comprising or consisting of the amino acid sequence as represented in SEQ ID NO: 43, 44, 45, 46, 47, 48 or 49; or
  ii) a polypeptide, or immunogenic fragment thereof, comprising or consisting of the amino acid sequence as represented in SEQ ID NO: 122 or 123; or 25; or
  iii) a modified polypeptide wherein said polypeptide is a polypeptide variant of the amino acid sequences presented in SEQ ID NO: 43, 44, 45, 46, 47, 48, 49, 122 or 123; wherein said sequences are modified by addition, deletion or substitution of one or more amino acid residues which modified polypeptides have retained or enhanced immunogenicity when compared to the polypeptide as represented in SEQ ID NO: 43, 44, 45, 46, 47, 48, 49, 122 or 123.

According to an aspect of the invention there is provided an immunogenic composition comprising two or more different polypeptides wherein said polypeptides are encoded by different *Haemophilus* spp genes selected from the group consisting of:
  i) a polypeptide, or immunogenic fragment thereof, comprising or consisting of the amino acid sequence as represented in SEQ ID NO: 50, 51, 52, 53, 54, 55 or 56; or
  ii) a polypeptide, or immunogenic fragment thereof, comprising or consisting of the amino acid sequence as represented in SEQ ID NO: 124 or 125; or
  iii) a modified polypeptide wherein said polypeptide is a polypeptide variant of the amino acid sequences presented in SEQ ID NO: 50, 51, 52, 53, 54, 55, 56, 124 or 125; wherein said sequences are modified by addition, deletion or substitution of one or more amino acid residues which modified polypeptides have retained or enhanced immunogenicity when compared to the polypeptide as represented in SEQ ID NO: 50, 51, 52, 53, 54, 55, 56, 124 or 125.

According to an aspect of the invention there is provided an immunogenic composition comprising two or more different polypeptides wherein said polypeptides are encoded by different *Heliobacter* spp genes selected from the group consisting of
  i) a polypeptide, or immunogenic fragment thereof, comprising or consisting of the amino acid sequence as represented in SEQ ID NO: 57, 58, 59, 60, 61, 62 or 63; or
  ii) a polypeptide, or immunogenic fragment thereof, comprising or consisting of the amino acid sequence as represented in SEQ ID NO: 126; or
  iv) a modified polypeptide wherein said polypeptide is a polypeptide variant of the amino acid sequences presented in SEQ ID NO: 57, 58, 59, 60, 61, 62, 63 or 126; wherein said sequences are modified by addition, deletion or substitution of one or more amino acid residues which modified polypeptides have retained or enhanced immunogenicity when compared to the polypeptide as represented in SEQ ID NO: 57, 58, 59, 60, 61, 62, 63 or 126.

According to an aspect of the invention there is provided an immunogenic composition comprising two or more different polypeptides wherein said polypeptides are encoded by different *Mycobacterium* spp genes selected from the group consisting of:
  i) a polypeptide, or immunogenic fragment thereof, comprising or consisting of the amino acid sequence as represented in SEQ ID NO: 64, 65, 66, 67, 68, 69 or 70; or
  ii) a polypeptide, or immunogenic fragment thereof, comprising or consisting of the amino acid sequence as represented in SEQ ID NO: 127 or 128; or
  iii) a modified polypeptide wherein said polypeptide is a polypeptide variant of the amino acid sequences presented in SEQ ID NO: 64, 65, 66, 67, 68, 69, 70, 127 or 128; wherein said sequences are modified by addition, deletion or substitution of one or more amino acid residues which modified polypeptides have retained or enhanced immunogenicity when compared to the polypeptide as represented in SEQ ID NO: 64, 65, 66, 67, 68, 69, 70, 127 or 128.

According to an aspect of the invention there is provided an immunogenic composition comprising two or more different polypeptides wherein said polypeptides are encoded by different *Shigella* spp genes selected from the group consisting of
  i) a polypeptide, or immunogenic fragment thereof, comprising or consisting of the amino acid sequence as represented in SEQ ID NO: 78, 79, 80, 81, 82, 83 or 84; or
  ii) a polypeptide, or immunogenic fragment thereof, comprising or consisting of the amino acid sequence as represented in SEQ ID NO: 134 or 135; or
  iii) a modified polypeptide wherein said polypeptide is a polypeptide variant of the amino acid sequences presented in SEQ ID NO: 78, 79, 80, 81, 82, 83, 84, 134 or 135; wherein said sequences are modified by addition, deletion or substitution of one or more amino acid residues which modified polypeptides have retained or enhanced immunogenicity when compared to the polypeptide as represented in SEQ ID NO: 78, 79, 80, 81, 82, 83, 84, 134 or 135.

According to an aspect of the invention there is provided an immunogenic composition comprising two or more different polypeptides wherein said polypeptides are encoded by different *Streptococcus* spp genes selected from the group consisting of
  i) a polypeptide, or immunogenic fragment thereof, comprising or consisting of the amino acid sequence as represented in SEQ ID NO: 85, 86, 87, 88, 89 or 90; or
  ii) a polypeptide, or immunogenic fragment thereof, comprising or consisting of the amino acid sequence as represented in SEQ ID NO 136 or 137; or
  iii) a polypeptide, or immunogenic fragment thereof, comprising or consisting of the amino acid sequence as represented in SEQ ID NO 152 or 153; or
  iv) a polypeptide, or immunogenic fragment thereof, comprising or consisting of the amino acid sequence as represented in SEQ ID NO 174 ore 175; or
  v) a modified polypeptide wherein said polypeptide is a polypeptide variant of the amino acid sequences presented in SEQ ID NO: 85, 86, 87, 88, 89, 90, 136, 137, 152, 153, 174 or 175; wherein said sequences are modified by addition, deletion or substitution of one or more amino acid residues which modified polypeptides have retained or enhanced immunogenicity when compared to the polypeptide as represented in SEQ ID NO 85, 86, 87, 88, 89, 90, 136, 137, 152, 153, 174 or 175.

According to an aspect of the invention there is provided an immunogenic composition comprising two or more different polypeptides wherein said polypeptides are encoded by different *Yersinia* spp genes selected from the group consisting of
  i) a polypeptide, or immunogenic fragment thereof, comprising or consisting of the amino acid sequence as represented in SEQ ID NO: 91, 92, 93, 94, 95, 96 or 97; or
  ii) a polypeptide, or immunogenic fragment thereof, comprising or consisting of the amino acid sequence as represented in SEQ ID NO: 138 or 139; or
  iii) a modified polypeptide wherein said polypeptide is a polypeptide variant of the amino acid sequences presented in SEQ ID NO: 91, 92, 93, 94, 95, 96, 97, 138 or 139 wherein said sequences are modified by addition, deletion or substitution of one or more amino acid residues which modified polypeptides have retained or enhanced immunogenicity when compared to the polypeptide as represented in SEQ ID NO: 91, 92, 93, 94, 95, 96, 97, 138 or 139.

According to an aspect of the invention there is provided an immunogenic composition comprising two or more different polypeptides wherein said polypeptides are encoded by different Streptococcus spp genes selected from the group consisting of:
  i) a polypeptide, or immunogenic fragment thereof, comprising or consisting of the amino acid sequence as represented in SEQ ID NO: 98, 99, 100, 101, 102, 103, or 104; or
  ii) a polypeptide, or immunogenic fragment thereof, comprising or consisting of the amino acid sequence as represented in SEQ ID NO: 140 or 141; or
  iii) a polypeptide, or immunogenic fragment thereof, comprising or consisting of the amino acid sequence as represented in SEQ ID NO: 154 or 155; or
  iv) a polypeptide, or immunogenic fragment thereof, comprising or consisting of the amino acid sequence as represented in SEQ ID NO: 164 or 165; or
  v) a polypeptide, or immunogenic fragment thereof, comprising or consisting of the amino acid sequence as represented in SEQ ID NO 172 or 173; or
  vi) a modified polypeptide wherein said polypeptide is a polypeptide variant of the amino acid sequences presented in SEQ ID NO: 98, 99, 100, 101, 102, 103, 104, 140, 141, 154, 155, 164, 165, 172 or 173 wherein said sequences are modified by addition, deletion or substitution of one or more amino acid residues which modified polypeptides have retained or enhanced immunogenicity when compared to the polypeptide as represented in SEQ ID NO: 98, 99, 100, 101, 102, 103, 104, 140, 141, 154, 155, 164, 165, 172 or 173.

According to an aspect of the invention there is provided an immunogenic composition comprising two or more different polypeptides wherein said polypeptides are encoded by different Streptococcus spp genes selected from the group consisting of:
  i) a polypeptide, or immunogenic fragment thereof, comprising or consisting of the amino acid sequence as represented in SEQ ID NO: 105, 106, 107, 108, 109, 110 or 111; or
  ii) a polypeptide, or immunogenic fragment thereof, comprising or consisting of the amino acid sequence as represented in SEQ ID NO: 142 or 143; or
  iii) a polypeptide, or immunogenic fragment thereof, comprising or consisting of the amino acid sequence as represented in SEQ ID NO: 156 or 157; or
  iv) a polypeptide, or immunogenic fragment thereof, comprising or consisting of the amino acid sequence as represented in SEQ ID NO: 166 or 167; or
  v) a polypeptide, or immunogenic fragment thereof, comprising or consisting of the amino acid sequence as represented in SEQ ID NO 176 or 177; or
  vi) a modified polypeptide wherein said polypeptide is a polypeptide variant of the amino acid sequences presented in SEQ ID NO: 105, 106, 107, 108, 109, 110, 111, 142, 143 156, 157, 166, 167, 176, 177, wherein said sequences are modified by addition, deletion or substitution of one or more amino acid residues which modified polypeptides have retained or enhanced immunogenicity when compared to the polypeptide as represented in SEQ ID NO: 105, 106, 107, 108, 109, 110, 111, 142, 143 156, 157, 166, 167, 176, 177.

According to an aspect of the invention there is provided an immunogenic composition comprising at least one Pseudomonas spp polypeptide selected from the group consisting of:
  i) a polypeptide, or immunogenic fragment thereof, comprising or consisting of the amino acid sequence as represented in SEQ ID NO: 71; or
  ii) a polypeptide, or immunogenic fragment thereof, comprising or consisting of the amino acid sequence as represented in SEQ ID NO: 72, 73, 74, 75, 76 or 77; or
  iii) a modified polypeptide wherein said polypeptide is a polypeptide variant of the amino acid sequence presented in SEQ ID NO: 71, 72, 73, 74, 75, 76 or 77, wherein said sequence is modified by addition, deletion or substitution of one or more amino acid residues which modified polypeptides have retained or enhanced immunogenicity when compared to the polypeptide as represented in SEQ ID NO: 71, 72, 73, 74, 75, 76 or 77.

According to an aspect of the invention there is provided an immunogenic composition comprising at least one Chlamydia spp polypeptide selected from the group consisting of:
  i) a polypeptide, or immunogenic fragment thereof, comprising or consisting of the amino acid sequence as represented in SEQ ID NO: 117; or
  ii) a modified polypeptide wherein said polypeptide is a polypeptide variant of the amino acid sequence presented in SEQ ID NO: 117, wherein said sequence is modified by addition, deletion or substitution of one or more amino acid residues which modified polypeptides have retained or enhanced immunogenicity when compared to the polypeptide as represented in SEQ ID NO 117.

According to an aspect of the invention there is provided an immunogenic composition comprising at least one Neisseria spp polypeptide selected from the group consisting of:
  i) a polypeptide, or immunogenic fragment thereof, comprising or consisting of the amino acid sequence as represented in SEQ ID NO: 130; or
  iii) a modified polypeptide wherein said polypeptide is a polypeptide variant of the amino acid sequence presented in SEQ ID NO: 130, wherein said sequence is modified by addition, deletion or substitution of one or more amino acid residues which modified polypeptides have retained or enhanced immunogenicity when compared to the polypeptide as represented in SEQ ID NO 130.

According to an aspect of the invention there is provided an immunogenic composition comprising least one Neisseria spp polypeptide selected from the group consisting of:
  i) a polypeptide, or immunogenic fragment thereof, comprising or consisting of the amino acid sequence as represented in SEQ ID NO: 131; or
  ii) a modified polypeptide wherein said polypeptide is a polypeptide variant of the amino acid sequence presented in SEQ ID NO: 131, wherein said sequence is modified by addition, deletion or substitution of one or more amino acid residues which modified polypeptides have retained or enhanced immunogenicity when compared to the polypeptide as represented in SEQ ID NO 131.

According to an aspect of the invention there is provided an immunogenic composition comprising at least one Pseudomonas spp polypeptide selected from the group consisting of:
  i) a polypeptide, or immunogenic fragment thereof, comprising or consisting of the amino acid sequence as represented in SEQ ID NO: 132 or 133; or ii) a modified polypeptide wherein said polypeptide is a polypeptide variant of the amino acid sequence presented in SEQ ID NO: 132 or 133, wherein said sequence is modified by addition, deletion or substitution of one or more amino acid residues which modified polypeptides have retained or enhanced immunogenicity when compared to the polypeptide as represented in SEQ ID NO 132 or 133.

In a preferred embodiment of the invention said immunogenic composition comprises or consists essentially of 2, 3, 4 or 5 antigenic polypeptides.

In a preferred embodiment of the invention said composition is a vaccine composition and includes at least one carrier and/or adjuvant.

Adjuvants (immune potentiators or immunomodulators) have been used for decades to improve the immune response to vaccine antigens. The incorporation of adjuvants into vaccine formulations is aimed at enhancing, accelerating and prolonging the specific immune response to vaccine antigens. Advantages of adjuvants include the enhancement of the immunogenicity of weaker antigens, the reduction of the antigen amount needed for a successful immunisation, the reduction of the frequency of booster immunisations needed and an improved immune response in elderly and immunocompromised vaccinees. Selectively, adjuvants can also be employed to optimise a desired immune response, e.g. with respect to immunoglobulin classes and induction of cytotoxic or helper T lymphocyte responses. In addition, certain adjuvants can be used to promote antibody responses at mucosal surfaces. Aluminium hydroxide and aluminium or calcium phosphate has been used routinely in human vaccines.

Adjuvants can be classified according to their source, mechanism of action and physical or chemical properties. The most commonly described adjuvant classes are gel-type, microbial, oil-emulsion and emulsifier-based, particulate, synthetic and cytokines. More than one adjuvant may be present in the final vaccine product according to the invention. They may be combined together with a single antigen or all antigens present in the vaccine, or each adjuvant may be combined with one particular antigen. The origin and nature of the adjuvants currently being used or developed is highly diverse. For example, aluminium based adjuvants consist of simple inorganic compounds and PLG is a polymeric carbohydrate. MDP is derived from bacterial cell walls; saponins are of plant origin, squalene is derived from shark liver and recombinant endogenous immunomodulators are derived from recombinant bacterial, yeast or mammalian cells. There are several adjuvants licensed for veterinary vaccines, such as mineral oil emulsions that are too reactive for human use. Similarly, complete Freund's adjuvant, although being one of the most powerful adjuvants known, is not suitable for human use.

A carrier is an immunogenic molecule which, when bound to a second molecule augments immune responses to the latter. The term carrier is construed in the following manner. A carrier is an immunogenic molecule which, when bound to a second molecule augments immune responses to the latter. Some antigens are not intrinsically immunogenic yet may be capable of generating antibody responses when associated with a foreign protein molecule such as keyhole-limpet haemocyanin or tetanus toxoid. Such antigens contain B-cell epitopes but no T cell epitopes. The protein moiety of such a conjugate (the "carrier" protein) provides T-cell epitopes which stimulate helper T-cells that in turn stimulate antigen-specific B-cells to differentiate into plasma cells and produce antibody against the antigen.

The vaccine compositions of the invention can be administered by any conventional route, including injection, intranasal spray by inhalation of for example an aerosol or nasal drops. The administration may be, for example, intravenous, intraperitoneal, intramuscular, intracavity, subcutaneous, or intradermally. The vaccine compositions of the invention are administered in effective amounts. An "effective amount" is that amount of a vaccine composition that alone or together with further doses, produces the desired response. In the case of treating a particular bacterial disease the desired response is providing protection when challenged by an infective agent.

In a preferred embodiment of the invention said vaccine composition is adapted for administration as a nasal spray.

In a preferred embodiment of the invention said vaccine composition is provided in an inhaler and delivered as an aerosol.

The amounts of vaccine will depend, of course, on the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used sufficient to provoke immunity; that is, the highest safe dose according to sound medical judgment. It will be understood by those of ordinary skill in the art, however, that a patient may insist upon a lower dose or tolerable dose for medical reasons, psychological reasons or for virtually any other reasons.

The doses of vaccine administered to a subject can be chosen in accordance with different parameters, in particular in accordance with the mode of administration used and the state of the subject. In the event that a response in a subject is insufficient at the initial doses applied, higher doses (or effectively higher doses by a different, more localized delivery route) may be employed to the extent that patient tolerance permits. In general, doses of vaccine are formulated and administered in effective immunizing doses according to any standard procedure in the art. Other protocols for the administration of the vaccine compositions will be known to one of ordinary skill in the art, in which the dose amount, schedule of injections, sites of injections, mode of administration and the like vary from the foregoing. Administration of the vaccine compositions to mammals other than humans, (e.g. for testing purposes or veterinary therapeutic purposes), is carried out under substantially the same conditions as described above. A subject, as used herein, is a mammal, preferably a human, and including a non-human primate, cow, horse, pig, sheep or goat.

In a preferred embodiment of the invention there is provided a vaccine composition according to the invention that includes at least one additional anti-bacterial agent.

In a preferred embodiment of the invention said agent is a second different vaccine and/or immunogenic agent (for example a bacterial polypeptide and/or polysaccharide antigen).

According to a further aspect of the invention there is provided a vaccine according to the invention for use in the protection or treatment of a subject animal to a microbial infection or condition that results from microbial infection.

In a preferred embodiment of the invention a bacterial pathogen that causes said microbial infection or condition is selected from the group consisting of: *Bacillus anthracis, Clostridium botulinum, Clostridium difficile, Enterococcus* faecalis, *Mycobacterium tuberculosis*, *Streptococcus* group A, *Streptococcus* group B, *Streptococcus pneumonia*.

In an alternative preferred embodiment of the invention a bacterial pathogen that causes said microbial infection or condition is selected from the group consisting of: *Helicobacter pylori*, *Neisseria gonorrhoea*, *Neisseria meningitidis* type B, *Shigella flexneri*, *Escherichia coli*, *Haemophilus influenzae*, *Chlamydia trachomatis*, *Pseudomonas aeruginosa*, *Yersinia pestis*, *Burkholderia mallei* or *B. pseudomallei*.

In a preferred embodiment of the invention said subject is a human.

In an alternative preferred embodiment of the invention said subject is a non-human animal, preferably a livestock animal, for example cattle.

Throughout the description and claims of this specification, the words "comprise" and "contain" and variations of the words, for example "comprising" and "comprises", means "including but not limited to", and is not intended to (and does not) exclude other moieties, additives, components, integers or steps Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

An embodiment of the invention will now be described by example only and with reference to the following materials, methods and the sequences in Table 1.

BRIEF DESCRIPTION OF THE DRAWINGS

FIG. 1 shows the sequences of SEQ ID NOS.: 1-111.
FIG. 2 shows the sequences of SEQ ID NOS.: 112-143.
FIG. 3 shows the sequences of SEQ ID NOS.: 144-157.
FIG. 4 shows the sequences of SEQ ID NOS.: 158-177.

MATERIALS AND METHODS

Construction of Plasmids for the Overexpression in *E. coli* of the Extramembranous Fragments of the Proteins The PheP selected peptides were synthesized and conjugated through a cysteine at its C terminal to the carrier protein KLH to undertake as a chimeric protein used in vaccinations. The extramembranous fragments of YdiE, DivlB, DivlC and FtsL were PCR amplified using oligonucleotide pairs indicated according to the following PCR reaction conditions: 1 initial denaturation cycle of 94° C. for 4 min; 30 amplification cycles of denaturation 94° C. for 30 seconds, annealing 45° C. for 30 seconds, and extension at 30 72° C. for up to 2.5 minutes; finally, ongoing amplification rounds were allow to complete at 72° C. for 4 min.

The restrictions sites were engineered within the oligonucleotides. The amplified fragments were digested with the corresponding restriction enzymes (NcoI for the 5' end, and XhoI for the 3' end) and cloned into the equivalent sites of the pET-21d(+) expression vector from Novagen (Cat. No. 69743-3) and resulting in the overexpression plasmids generating a T7-tagged (partial, at the N-terminal) and 6xHis-tagged (at the C-terminal end) form of the extramembranous fragments. The over expression plasmids were transferred into *E. coli* BL21 for over expression of the recombinant protein fragment.

The cloning of the PCR amplified fragment indicated above into the recipient pET21d(+) recipient plasmid vector at the NcoI and XhoI sites entailed the addition of hinge amino acids between the T7-tag and the extramembranous fragment, and between the latter and the His-tag.

Over Expression of Polypeptide Sequences

SEQ IDs were over expressed from plasmids pGL597, pGL601, pALB26, and pALB27 in *E. coli* BL21 strain using Brain Heart Infusion Broth (CMO225, Oxoid, United Kingdom) in the presence of 100 ^g/ml ampicillin and the Plac promoter gratuitous inducer IPTG (Isopropyl p-D-1-thiogalactopyranoside, 1 mM) for 4 to 6 hours at 37° C. and vigorous shaking. Following harvesting of the cells by centrifugation (5,000×g for 15 minutes at 4° C.) and subsequent lysis with 1 mg/ml lysozyme in phosphate buffer (Buffer A; 0.1 M pH7.2) containing 0.5M NaCl) for one hour and subsequent sonication (3 cycles of 10 second pulses in sonicating water bath) the soluble and insoluble forms of the proteins of interest were separated by centrifugation at 13,000×g for 10 minutes. The precipitate was then resuspended in Buffer A containing 8M urea by freeze/thawing (3 cycles of freezing at –80° C. for 10 minutes and subsequent thawing to room temperature) and sonication (3 cycles of 10 second pulses in sonicating water bath), and subsequent centrifugation for 25 minutes at 18,000×g). The over expressed proteins of interest in the supernatant and the solubilised pellet were purified by initial specific binding (through their His-tag) to a nickel (NiSO4)-bound Sepharose chromatography column (Ni— Sepharose) and elution with an imidazole solution run through the column in the following stepwise manner: 5% for 5 minutes, 30% for 60 minutes, 35% for 60 minutes, 50% for 100 minutes and 55% for 100 minutes. Fractions from this stepwise elution were analysed in acrylamide denaturing gels with a 4% acrylamide/bis-acrilamide stacking layer and a 12% acrylamide/bis-acrylamide separating layer. The fractions containing the over expressed proteins of interest were pooled and dyalized against sterile phosphate buffer (8 g NaCl, 0.2 g KCl, 1.44 g Na2HPO, 0.24 g $KH_2PO_4$, per liter of distilled $H_2O$, pH 7.4).

All the proteins of interest were successfully over expressed from the indicated strains and under the indicated conditions. They were also subsequently extracted from the total cellular protein content of the over expressing *E. coli* strains with more than 95% purity. Examples of the purification obtained for each of the proteins are indicated below.

Vaccination: Generic Protocol for Polyvalent Vaccines

Combination (or polyvalent) vaccines including variations of the antigens (conjugated selected PheP peptide, YdiE, DivlB, DivlC and FtsL) will follow an identical protocol with the following modifications. The vaccine priming and boost mixtures will contain rather than a single component 2 or more of the components. The total volume of mixed vaccine used for priming and boosting injections will fluctuate in a range of 50-100 microliters per animal. Similarly the total amount in each of those injections may vary between 50-100 micrograms. The amount of each antigen to contribute to the total amount of vaccine in the priming or boosting mix will vary between 20% to 80% of the total.

Vaccination: Generic Protocol for Monovalent Vaccines

The generic protocol followed for the vaccinations is as follows. Each animal was primed with 100 microliters of a solution made up of a mixture 50 micrograms of recombinant antigen in 50 microliters endotoxin-free PBS (Phosphate Buffer Saline pH 7.4) and 50 microliters of Complete Freund's adjuvant. Two weeks later the animals were boosted 25 with 100 microliters of a solution made up of a mixture 50 micrograms of recombinant protein in 50 microliters of endotoxin-free PBS and 50 microliters of Incomplete Freund's adjuvant. A week later the animals received an identical boost. In each experiment, a control group of 10 animals were treated following an identical protocol except for the fact that instead of the recombinant protein component the mixture contained commercially available KLH protein (Keyhole limpet hemocyanin). Priming and boost injections were performed intradermally in the scruff of the neck of the animals.

| Bacterial Species | PheP FL | PheP ECD | GCP FL | GCP ECD | Div1B FL | DIV1B ECD | Div1C FL | Div1C ECD | FtsL FL | FtsL ECD |
|---|---|---|---|---|---|---|---|---|---|---|
| Bacillus Anthracis | 1 | 2, 3, 4, 5, 6, 7 | 112 | | 144 | 145 | 158 | 159 | 168 | 169 |
| Burkholderia Mallei | 8 | 9, 10, 11, 12, 13, 14 | 113 | 114 | | | | | | |
| Burkholderia pseudomallei | 15 | 16, 17, 18, 19, 20, 21 | 115 | 116 | | | | | | |
| Chlamydia trachomatis | | | 117 | | | | | | | |
| Clostridium Botulinum | 22 | 23, 24, 25, 26, 27, 28 | 118 | | 146 | 147 | 160 | 161 | | |
| Clostridium Difficile | 29 | 30, 31, 32, 33, 34, 35 | 119 | | 148 | 149 | | | | |
| Enterococcus Faecalis | 36 | 37, 38, 39, 40, 41, 42 | 120 | 121 | 150 | 151 | 162 | 163 | 170 | 171 |
| Escherichia Coli | 43 | 44, 45, 46, 47, 48, 49 | 122 | 123 | | | | | | |
| Haemophilus influenza | 50 | 51, 52, 53, 54, 55, 56 | 124 | 125 | | | | | | |
| Helicobacter Pylori | 57 | 58, 59, 60, 61, 62, 63 | 126 | | | | | | | |
| Mycobacterium tuberculosis | 64 | 65, 66, 67, 68, 69, 70 | 127 | 128 | | | | | | |
| Pseudomonas Aeruginosa | 71 | 72, 73, 74, 75, 76, 77 | | | | | | | | |
| Neisseria gonorrhoeae | | | 130 | | | | | | | |
| Neisseria meningitidis | | | 131 | | | | | | | |
| Pseudomonas aeruginosa | | | 132 | 133 | | | | | | |
| Shigella flexneri | 78 | 79, 80, 81, 82, 83, 84 | 134 | 135 | | | | | | |
| Streptococcus pneumonia | 85 | 86, 87, 88, 89, 90 | 136 | 137 | 152 | 153 | | | 174 | 175 |
| Yersinia pestis | 91 | 92, 93, 94, 95, 96, 97 | 138 | 139 | | | | | | |
| Streptococcus agalactiae | 98 | 99, 100, 101, 102, 103, 104 | 140 | 141 | 154 | 155 | 164 | 165 | 172 | 173 |
| Streptococcus pyogenes | 105 | 106, 107, 108, 109, 110, 111 | 142 | 143 | 156 | 157 | 166 | 167 | 176 | 177 |

Table 1 discloses SEQ ID NOs corresponding to antigenic polypeptides [FL = full length sequence; ECD = extracellular domain

The invention claimed is:

1. An immunogenic composition, comprising an effective amount of an adjuvant and two or more different isolated polypeptides selected from:
   i) a polypeptide comprising or consisting of the amino acid sequence as represented in SEQ ID NO: 119 or 149;
   ii) an immunogenic polypeptide variant having at least 90% identity to the amino acid sequence represented in SEQ ID NO:119 or 149, which immunogenic polypeptide variants have retained immunogenicity as compared to the polypeptide having the amino acid sequence represented in SEQ ID NO: 119 or 149 respectively; and
   iii) any combination of isolated polypeptides from (i) and/or (ii).

2. The immunogenic composition according to claim 1, wherein the immunogenic composition consists essentially of 3, 4 or 5 different polypeptides.

3. The immunogenic composition according to claim 1, wherein the composition further comprises at least one carrier.

4. The immunogenic composition according to claim 3, wherein the composition further comprises at least one additional anti-bacterial agent.

5. A method to immunize a subject from a *Clostridium difficile* infection comprising administering an effective amount of an immunogenic composition according to claim 1 to the subject.

6. An immunogenic composition, comprising (a) an effective amount of an adjuvant, (b) a first polypeptide comprising or consisting of the amino acid sequence as represented in SEQ ID NO: 119, and (c) a second polypeptide comprising or consisting of the amino acid sequence as represented in SEQ ID NO: 149.

7. An immunogenic composition of claim 6, wherein the first polypeptide consists of the amino acid sequence as represented in SEQ ID NO: 119, and the second polypeptide consists of the amino acid sequence as represented in SEQ ID NO: 149.

8. The immunogenic composition according to claim 6, wherein the immunogenic composition consists essentially of 3, 4, or 5 different polypeptides.

9. The immunogenic composition according to claim 1, wherein the adjuvant is a gel-type adjuvant.

10. The immunogenic composition according to claim 1, wherein the adjuvant is an aluminium based adjuvant.

11. The immunogenic composition according to claim 10, wherein the aluminium based adjuvant is aluminium hydroxide.

12. The immunogenic composition according to claim 10, wherein the aluminium based adjuvant is aluminium phosphate.

13. The immunogenic composition according to claim 6, wherein the adjuvant is a gel-type adjuvant.

14. The immunogenic composition according to claim 6, wherein the adjuvant is an aluminium based adjuvant.

15. The immunogenic composition according to claim 14, wherein the aluminium based adjuvant is aluminium hydroxide.

16. The immunogenic composition according to claim 14, wherein the aluminium based adjuvant is aluminium phosphate.

17. The immunogenic composition according to claim 1, wherein the immunogenic polypeptide variant has at least 95% identity to the amino acid sequence represented in SEQ ID NO: 119 or 149.

18. The immunogenic composition according to claim 1, wherein the immunogenic polypeptide variant has 99% identity to the amino acid sequence represented in SEQ ID NO: 119 or 149.

19. The method according to claim 5, wherein the immunogenic composition consists essentially of 3, 4, or 5 different polypeptides.

20. The method according to claim 5, wherein the two or more different isolated polypeptides of the immunogenic composition comprise a first polypeptide comprising or consisting of the amino acid sequence as represented in SEQ ID NO: 119, and a second polypeptide comprising or consisting of the amino acid sequence as represented in SEQ ID NO: 149.

* * * * *